(12) United States Patent
Forsell

(10) Patent No.: US 10,653,544 B2
(45) Date of Patent: May 19, 2020

(54) RESTRICTION DEVICE

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 40 days.

(21) Appl. No.: 14/852,672

(22) Filed: Sep. 14, 2015

(65) Prior Publication Data

US 2016/0074196 A1    Mar. 17, 2016

Related U.S. Application Data

(63) Continuation of application No. PCT/EP2014/055112, filed on Mar. 14, 2014.

(30) Foreign Application Priority Data

Mar. 15, 2013    (SE) ...................... 1350319

(51) Int. Cl.
*A61F 5/00* (2006.01)
*A61F 2/00* (2006.01)
(Continued)

(52) U.S. Cl.
CPC ............ *A61F 5/0059* (2013.01); *A61F 2/004* (2013.01); *A61F 5/003* (2013.01); *A61F 5/0033* (2013.01); *A61F 5/0053* (2013.01); *A61F 5/0056* (2013.01); *A61F 6/202* (2013.01); *A61F 2005/0016* (2013.01); *A61F 2250/0002* (2013.01); *A61F 2250/0003* (2013.01); *A61F 2250/0013* (2013.01); *A61M 1/106* (2013.01); *A61M 1/1055* (2014.02);
(Continued)

(58) Field of Classification Search
CPC .......... A61F 5/005–0066; A61F 2/0027; A61F 2/0033; A61F 2/004; A61F 6/202; A61F 2250/0003; A61F 2250/0013; A61B 17/12
See application file for complete search history.

(56) References Cited

U.S. PATENT DOCUMENTS

| 2004/0122527 A1* | 6/2004 | Imran ....................... A61F 2/04 623/23.67 |
| 2006/0211913 A1* | 9/2006 | Dlugos ................... A61F 2/004 600/37 |

(Continued)

FOREIGN PATENT DOCUMENTS

| DE | 10023634 A1 | 10/2002 |
| WO | 2009046996 A1 | 4/2009 |

(Continued)

*Primary Examiner* — Thaddeus B Cox

(57) ABSTRACT

A hydraulic implantable restriction device for restricting a luminary organ of a patient. The hydraulic implantable restriction device comprises: a first hydraulic restriction element adapted to restrict a first portion of the luminary organ, and a second hydraulic restriction element adapted to restrict a second portion of the luminary organ, and a control unit adapted to control the first and second restriction elements for automatically switching between restricting the first and second portion of the luminary organ, for creating a less damaging restriction. The control unit is adapted to automatically switch between restricting the first and second portion of the luminary organ on the basis of at least one of: a lapsed time being between 10 minutes and 6 months, and the patient using the function of the restricted luminary organ.

29 Claims, 26 Drawing Sheets

(51) Int. Cl.
*A61F 6/20* (2006.01)
*A61M 1/10* (2006.01)
*A61M 1/12* (2006.01)

(52) U.S. Cl.
CPC ......... *A61M 1/1056* (2014.02); *A61M 1/1058* (2014.02); *A61M 1/1067* (2013.01); *A61M 1/1086* (2013.01); *A61M 1/12* (2013.01); *A61M 2205/0283* (2013.01); *A61M 2205/33* (2013.01); *A61M 2205/3303* (2013.01)

(56) References Cited

U.S. PATENT DOCUMENTS

| | | | |
|---|---|---|---|
| 2009/0240100 A1 | 9/2009 | Forsell | |
| 2011/0066254 A1* | 3/2011 | Forsell | A61M 1/1068 623/23.64 |
| 2011/0201875 A1* | 8/2011 | Stroumpoulis | A61F 5/005 600/37 |
| 2012/0157759 A1 | 7/2012 | Wirbisky | |
| 2014/0371855 A1* | 12/2014 | Clement | A61F 2/0036 623/14.13 |

FOREIGN PATENT DOCUMENTS

| | | | | |
|---|---|---|---|---|
| WO | WO 2011006900 A1 * | 1/2011 | | A61F 2/12 |
| WO | 2013091730 A1 | 6/2013 | | |

* cited by examiner

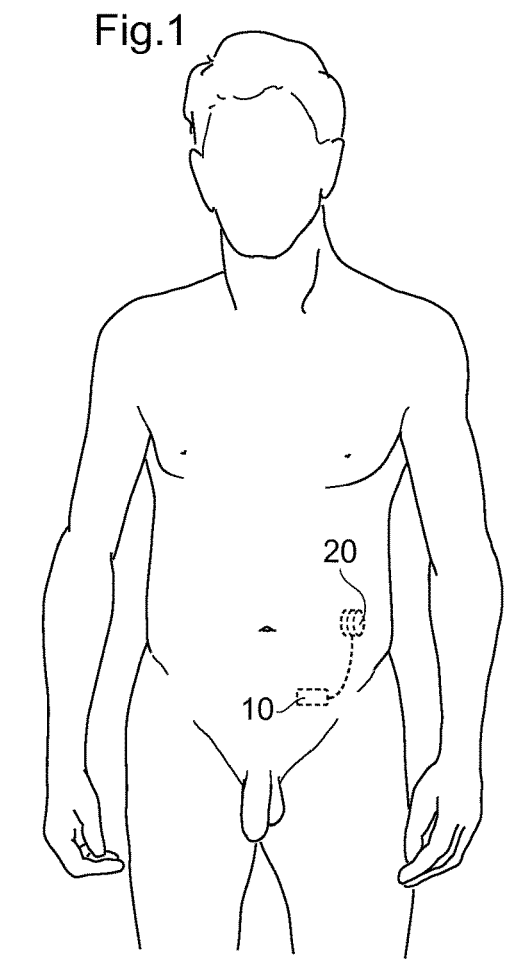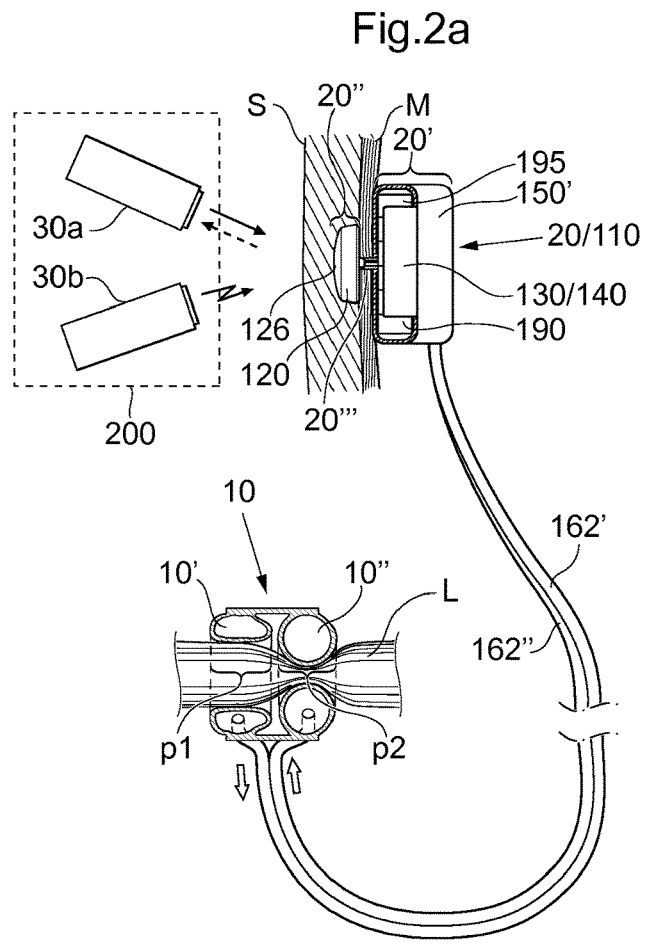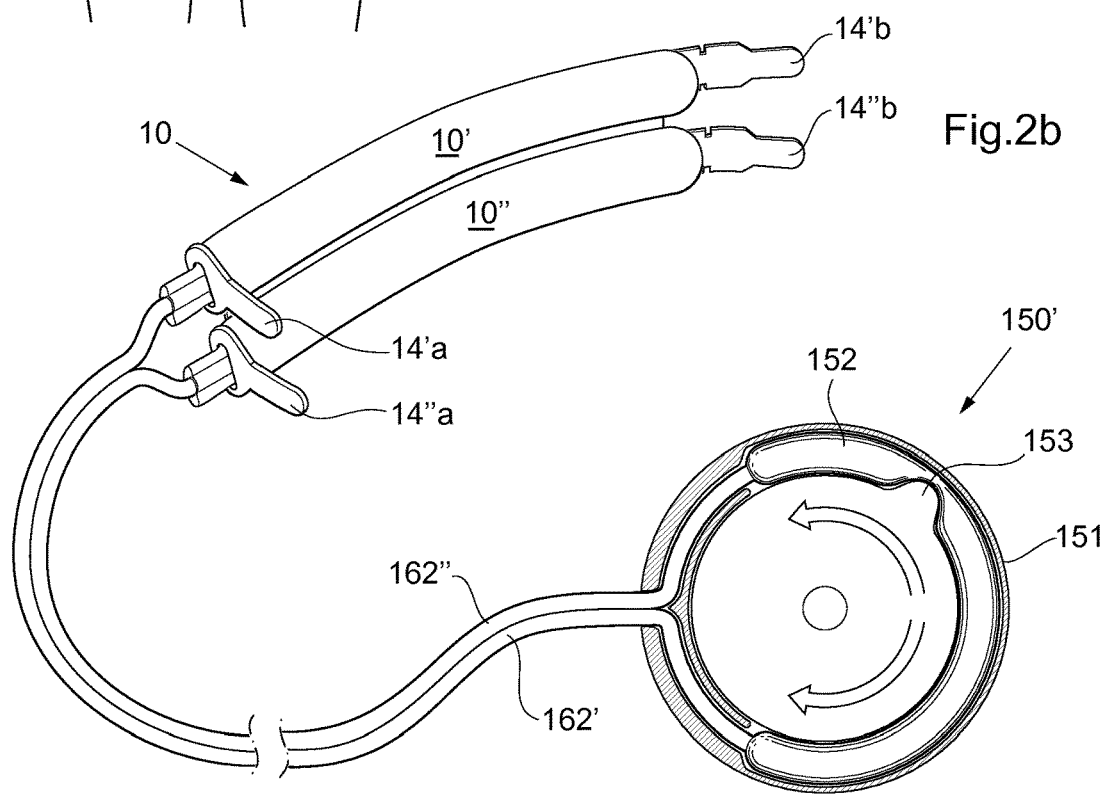

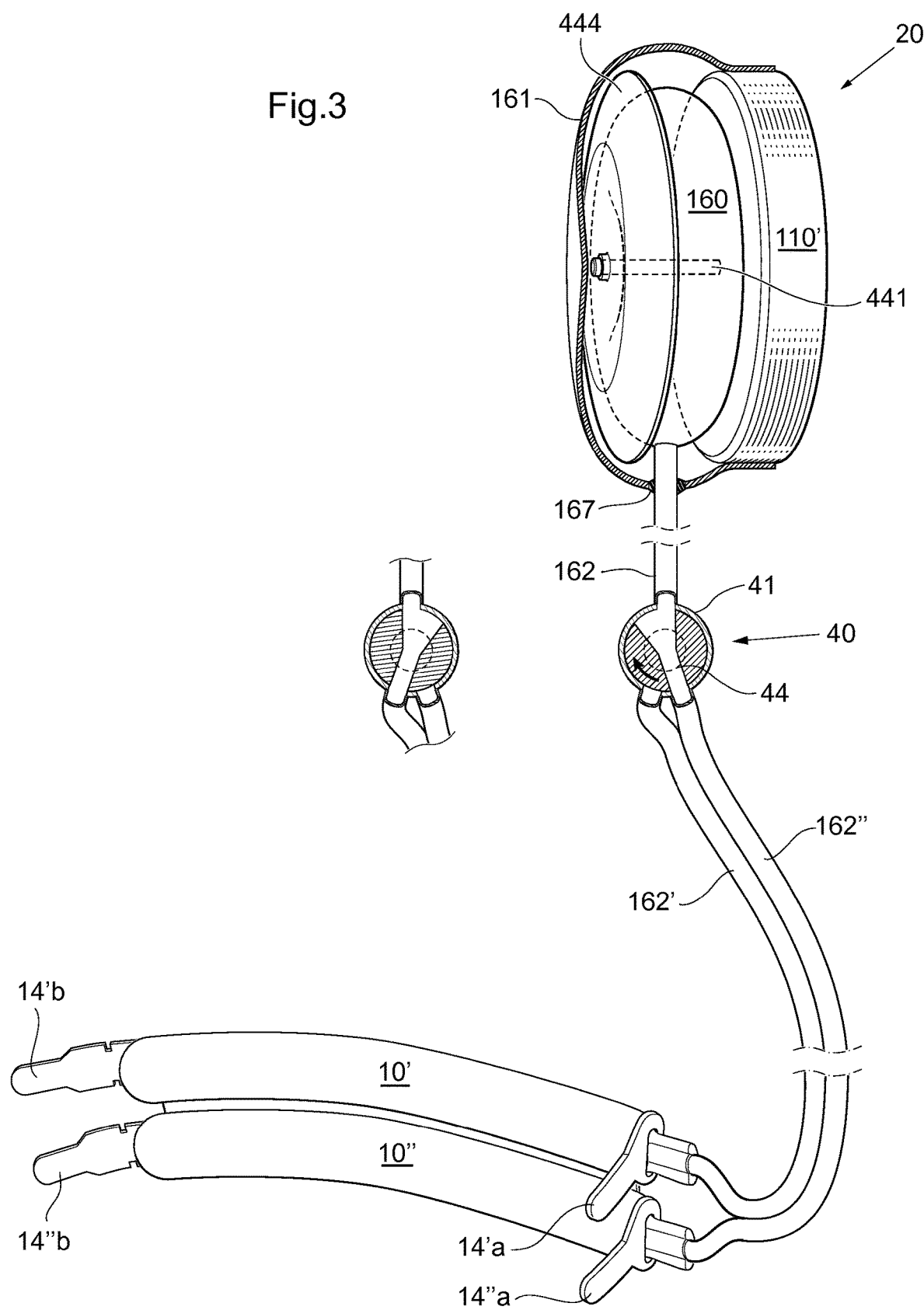

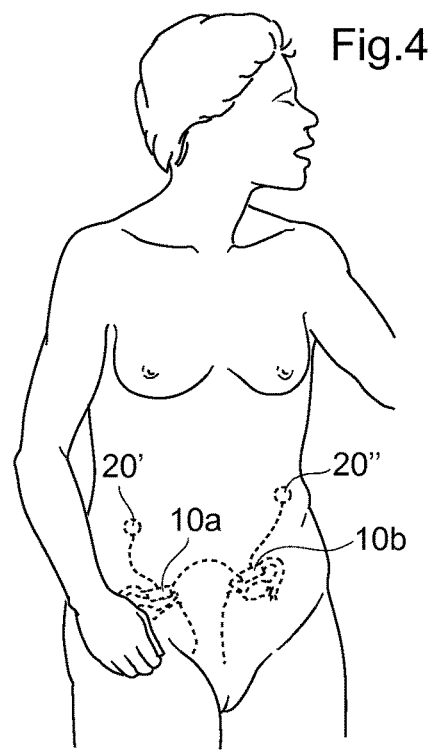
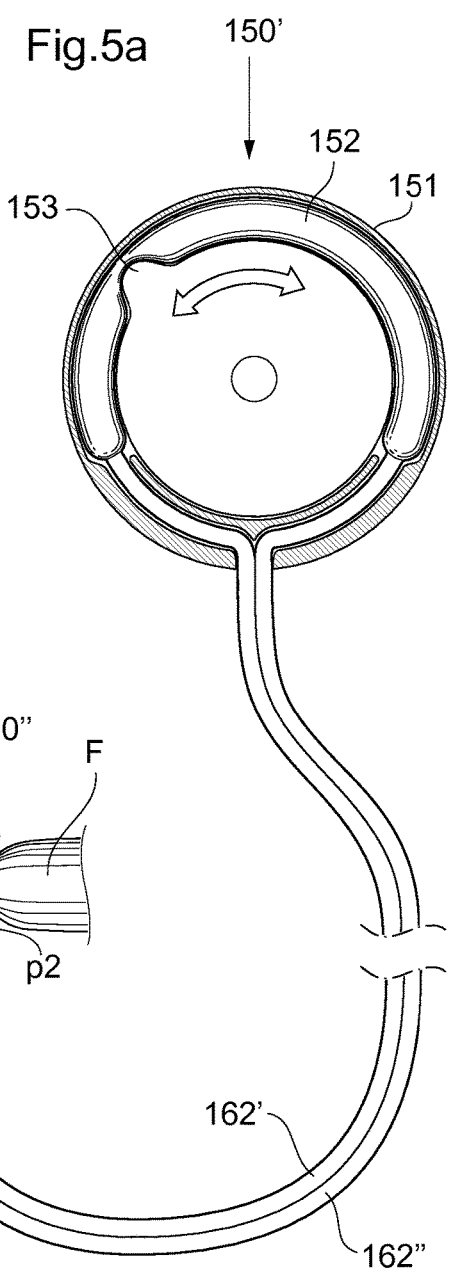
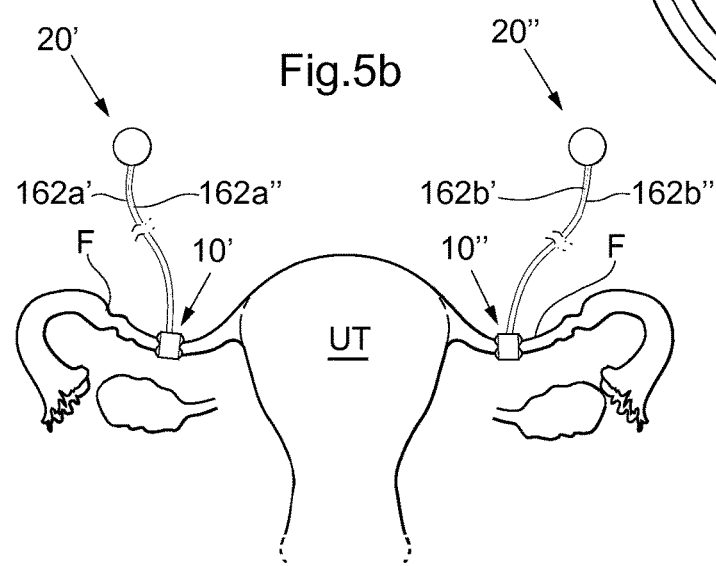

Fig.12
Fig.13a
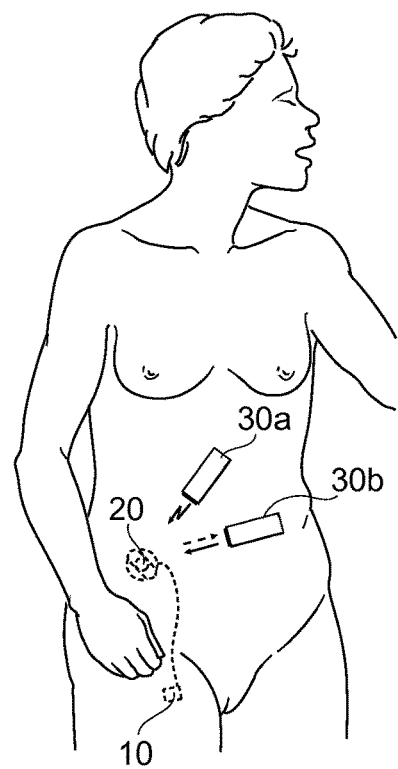
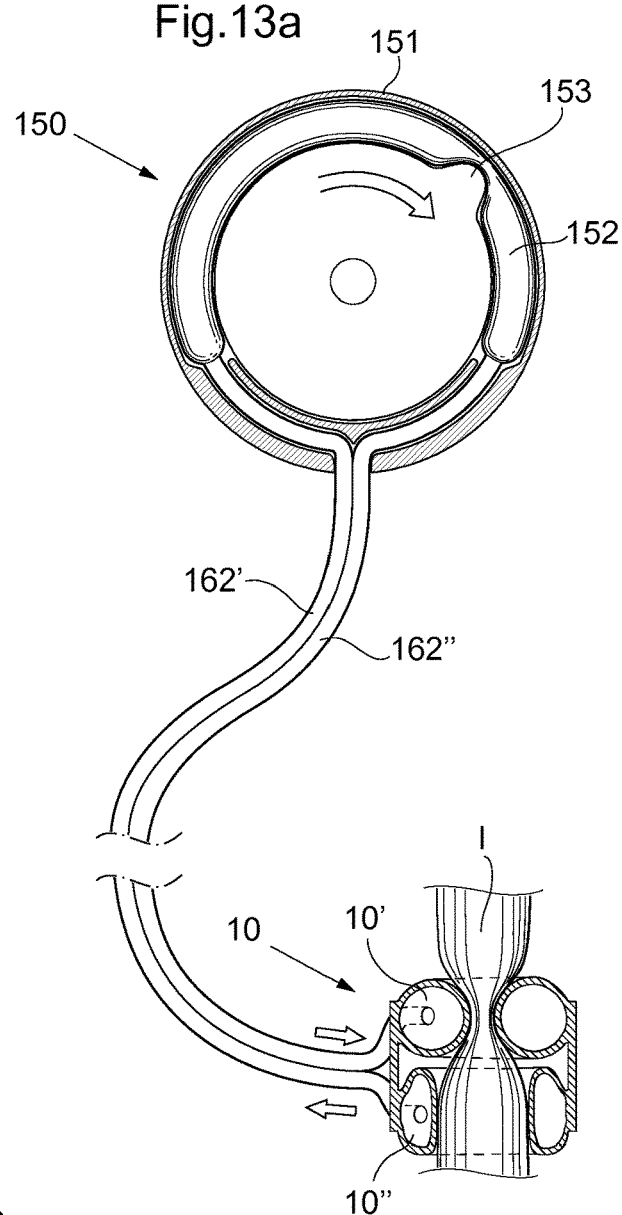
Fig.13b
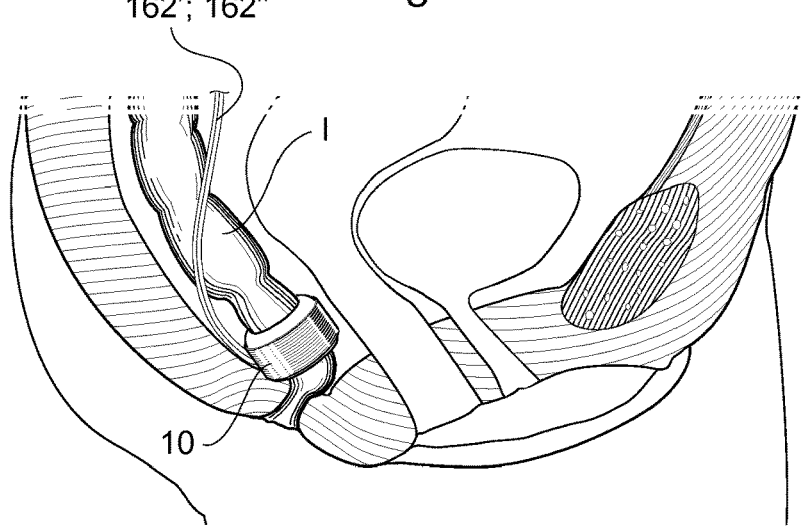

Fig.22
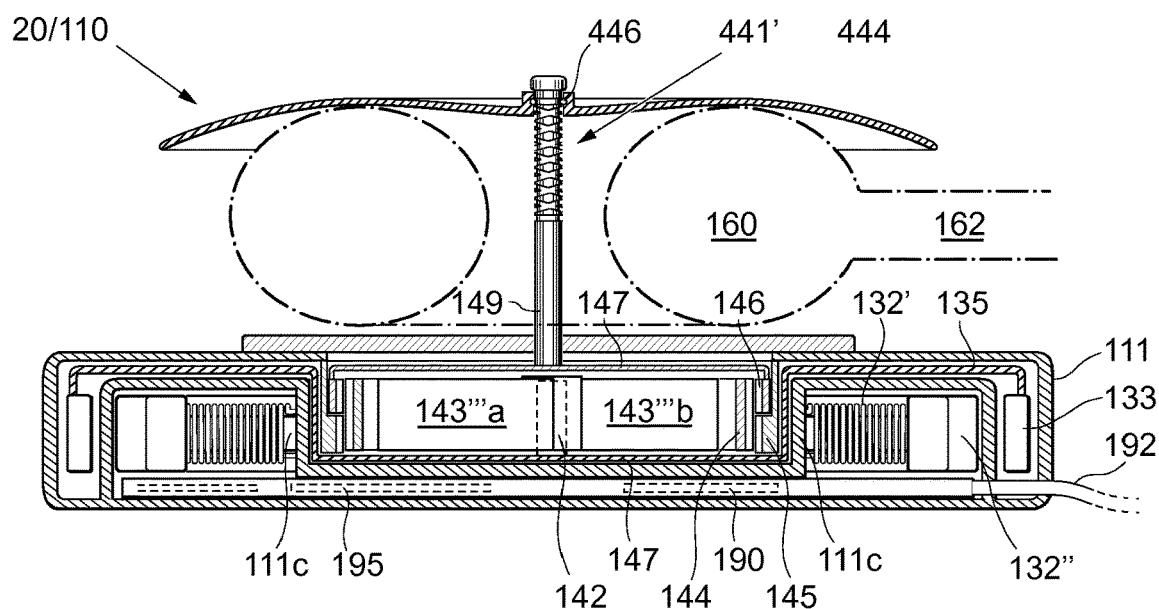
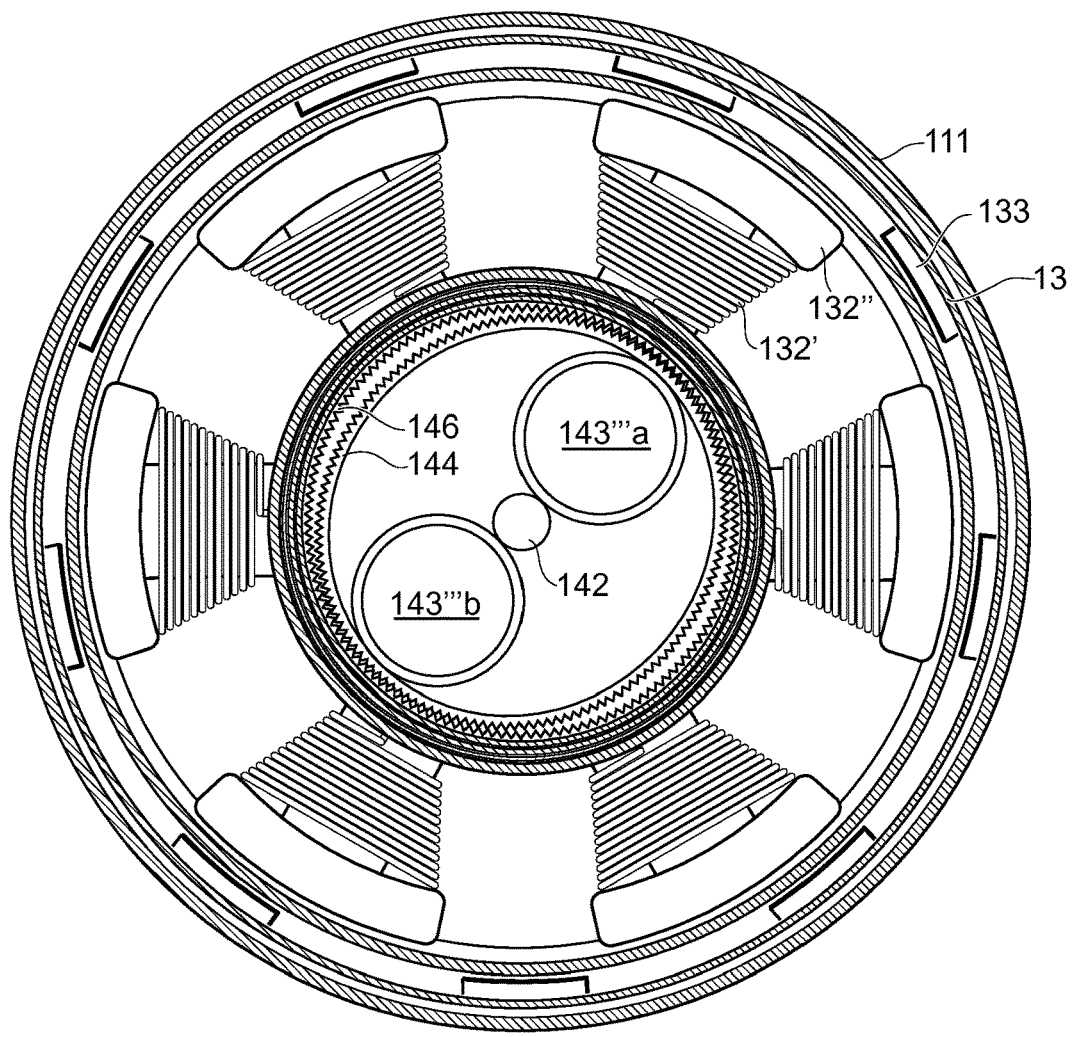

Fig.23
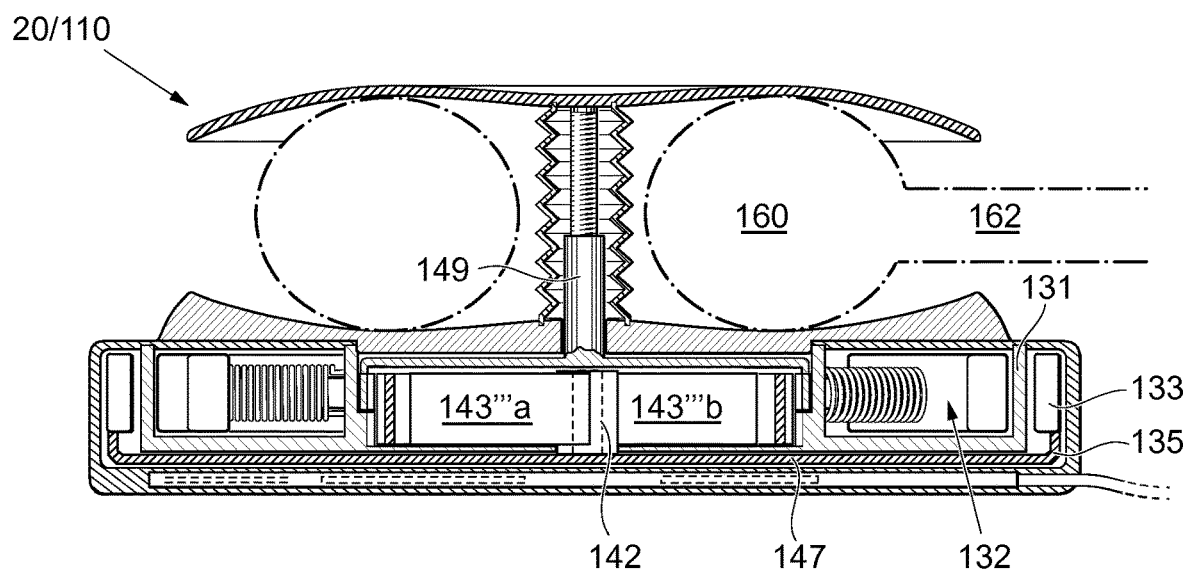
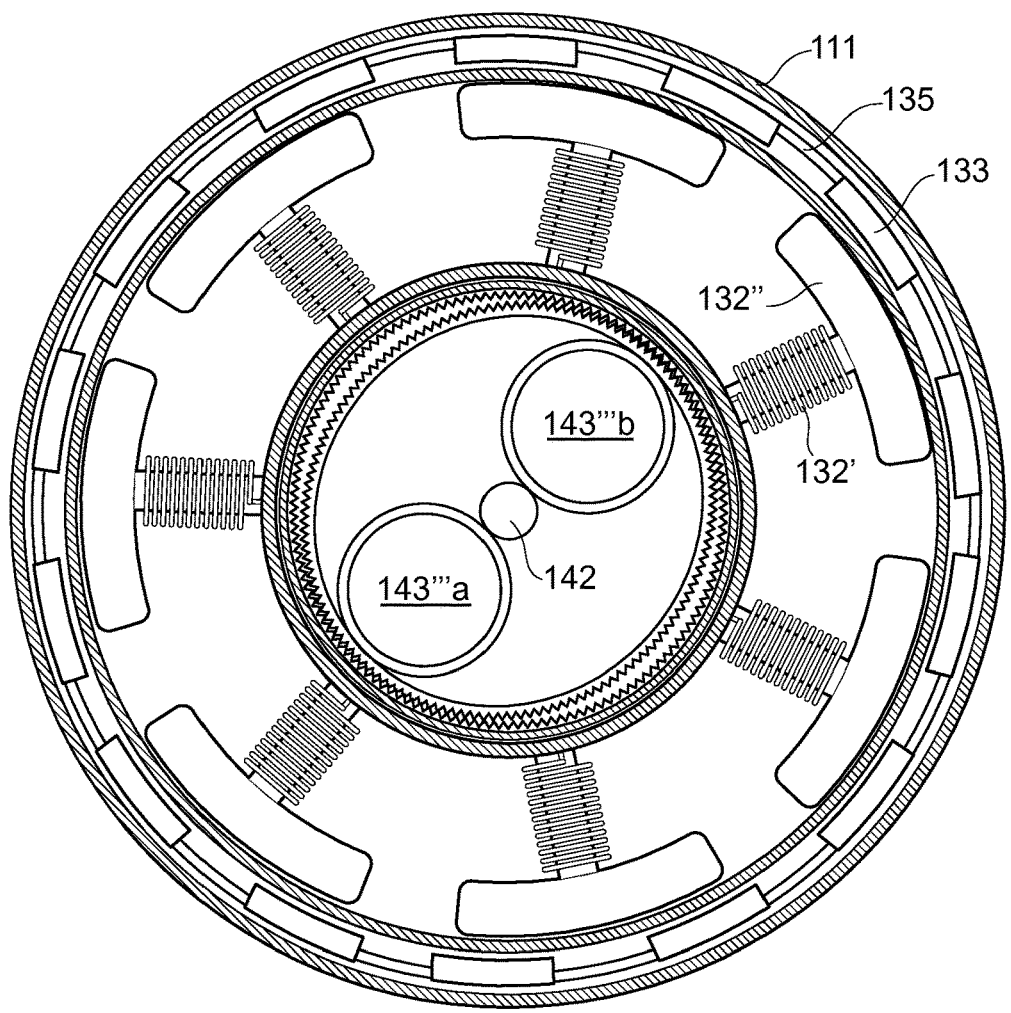

Fig.24
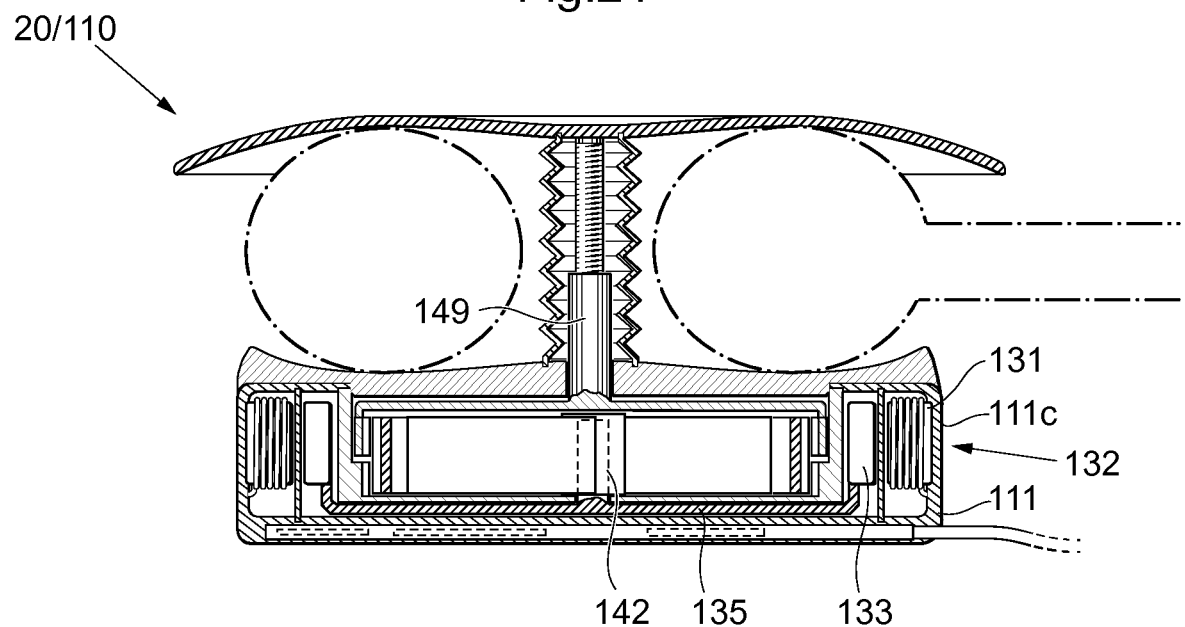
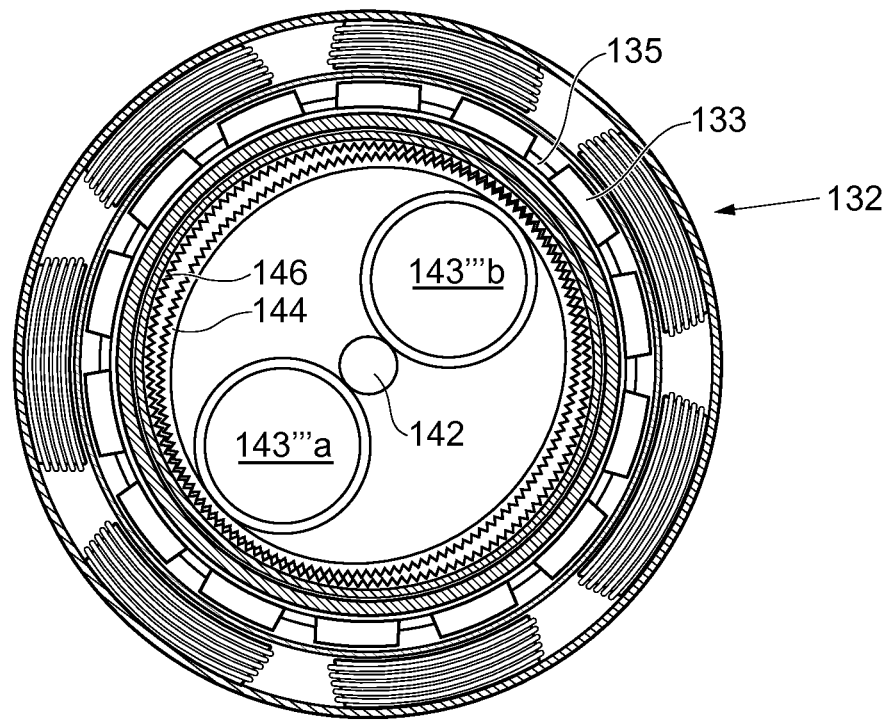

Fig.25
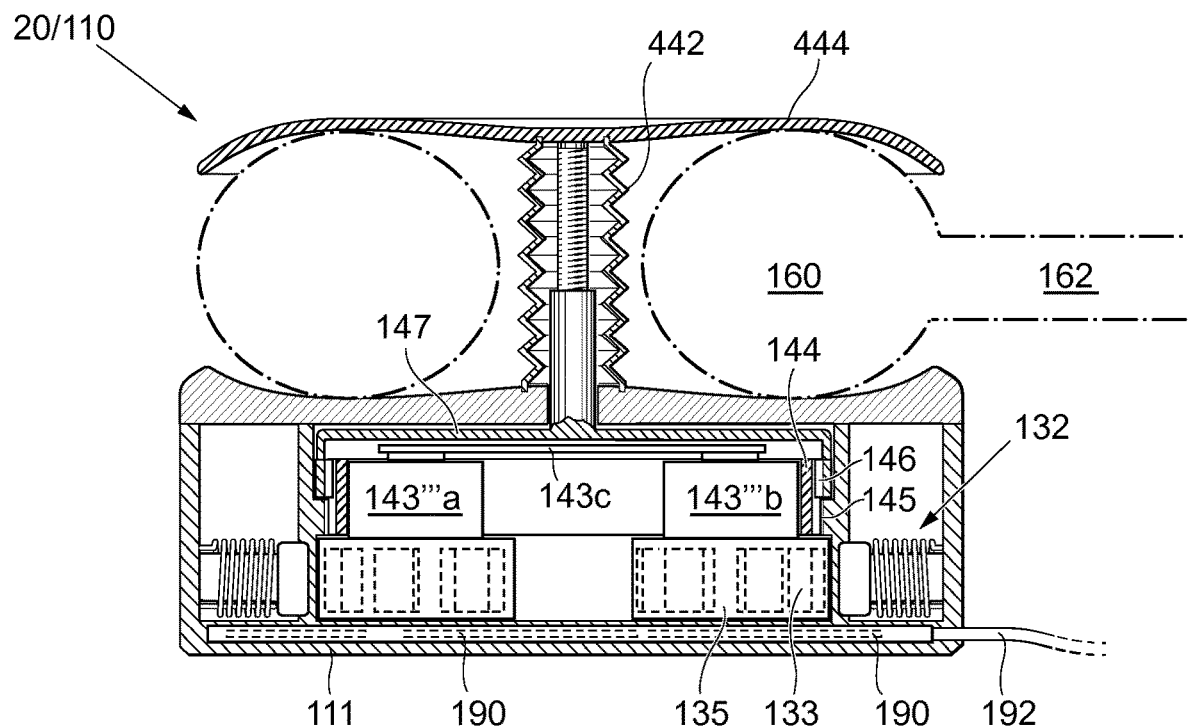
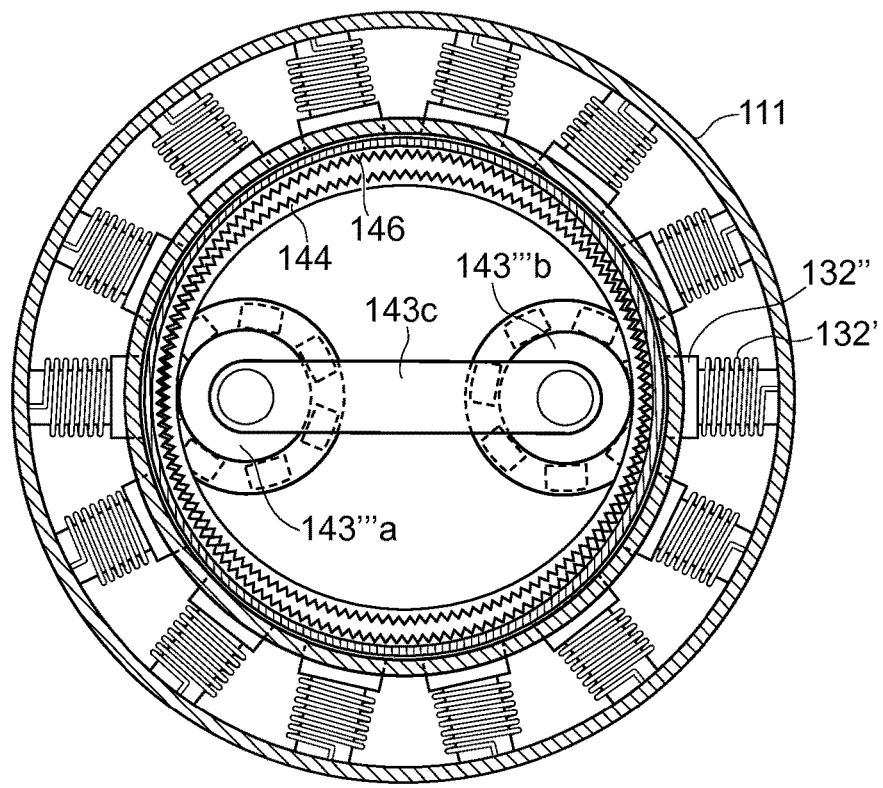

Fig.29
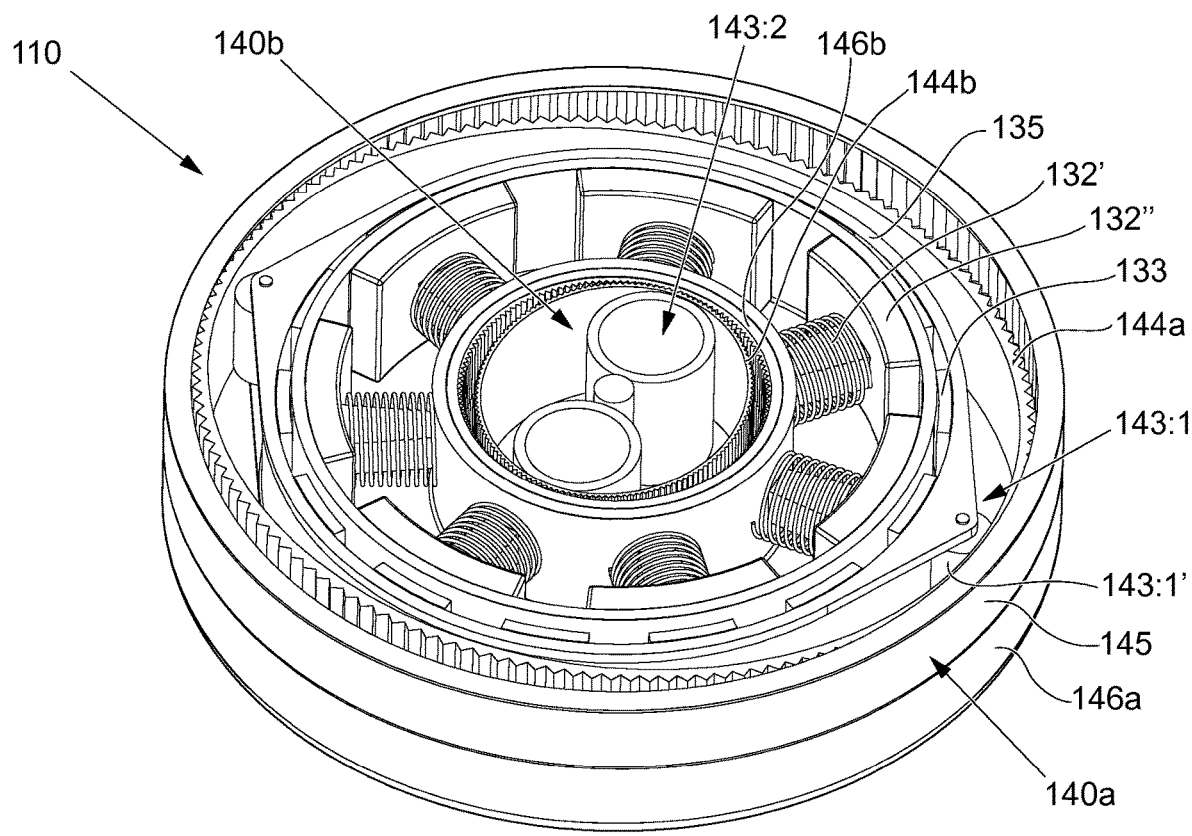
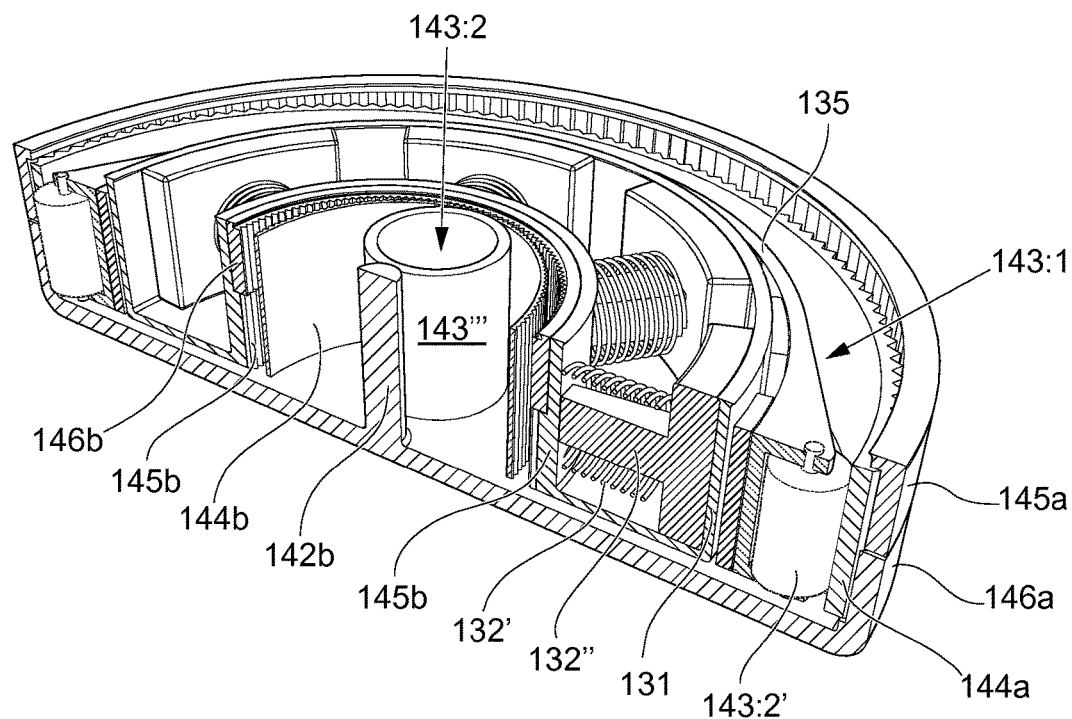

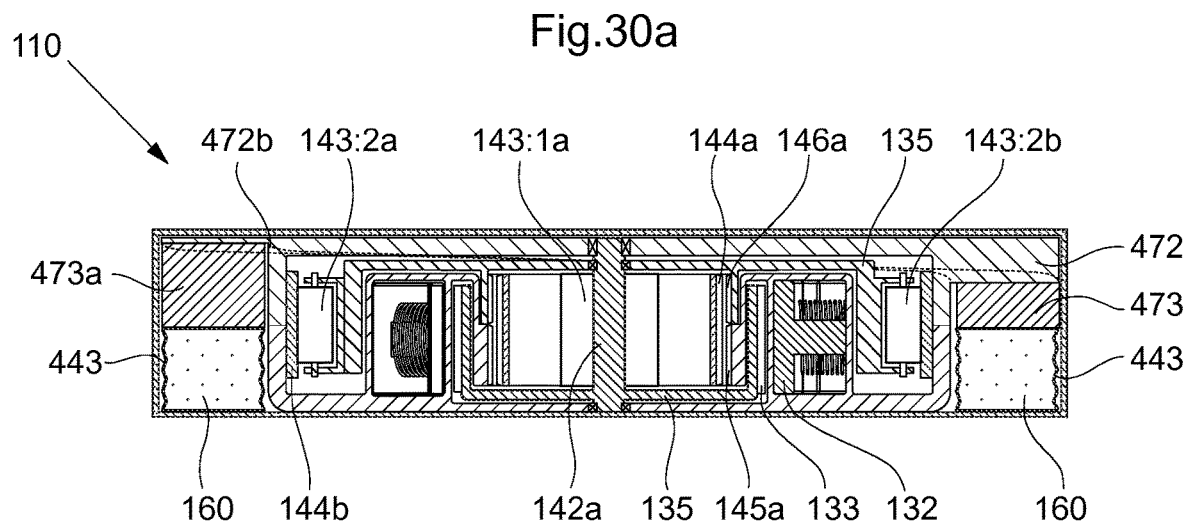
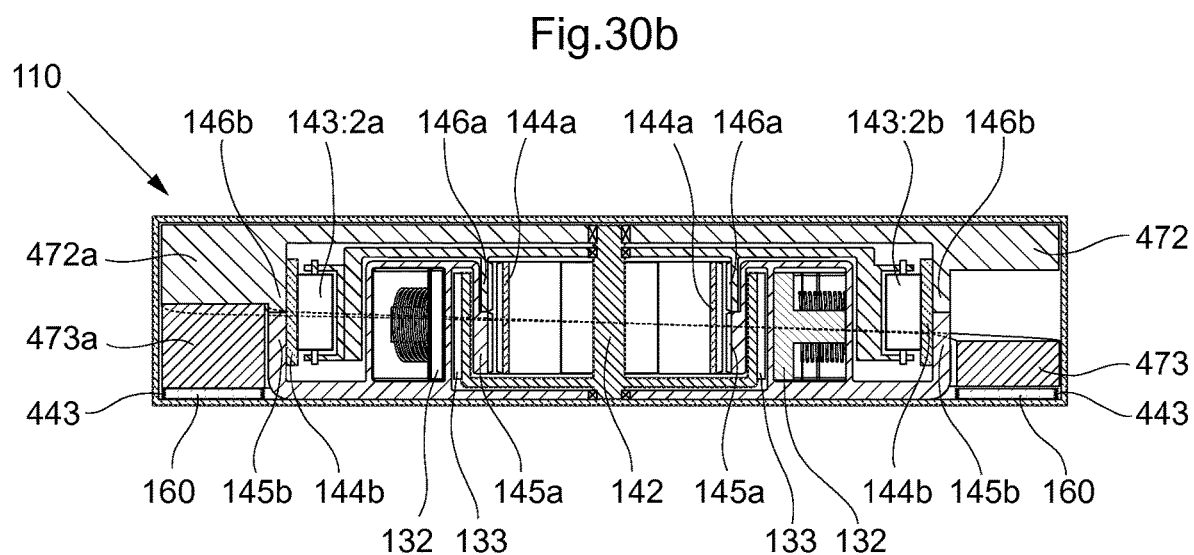

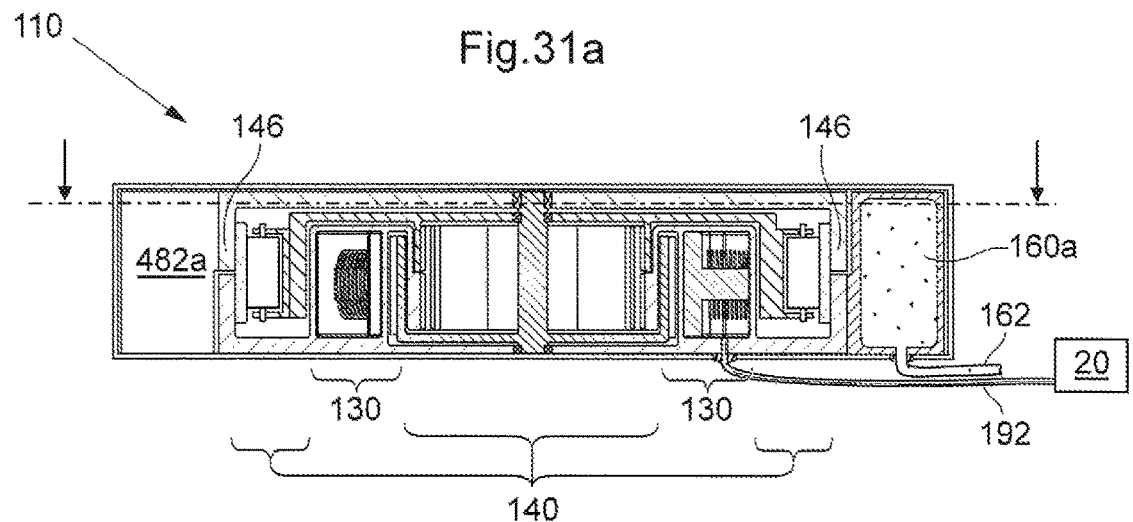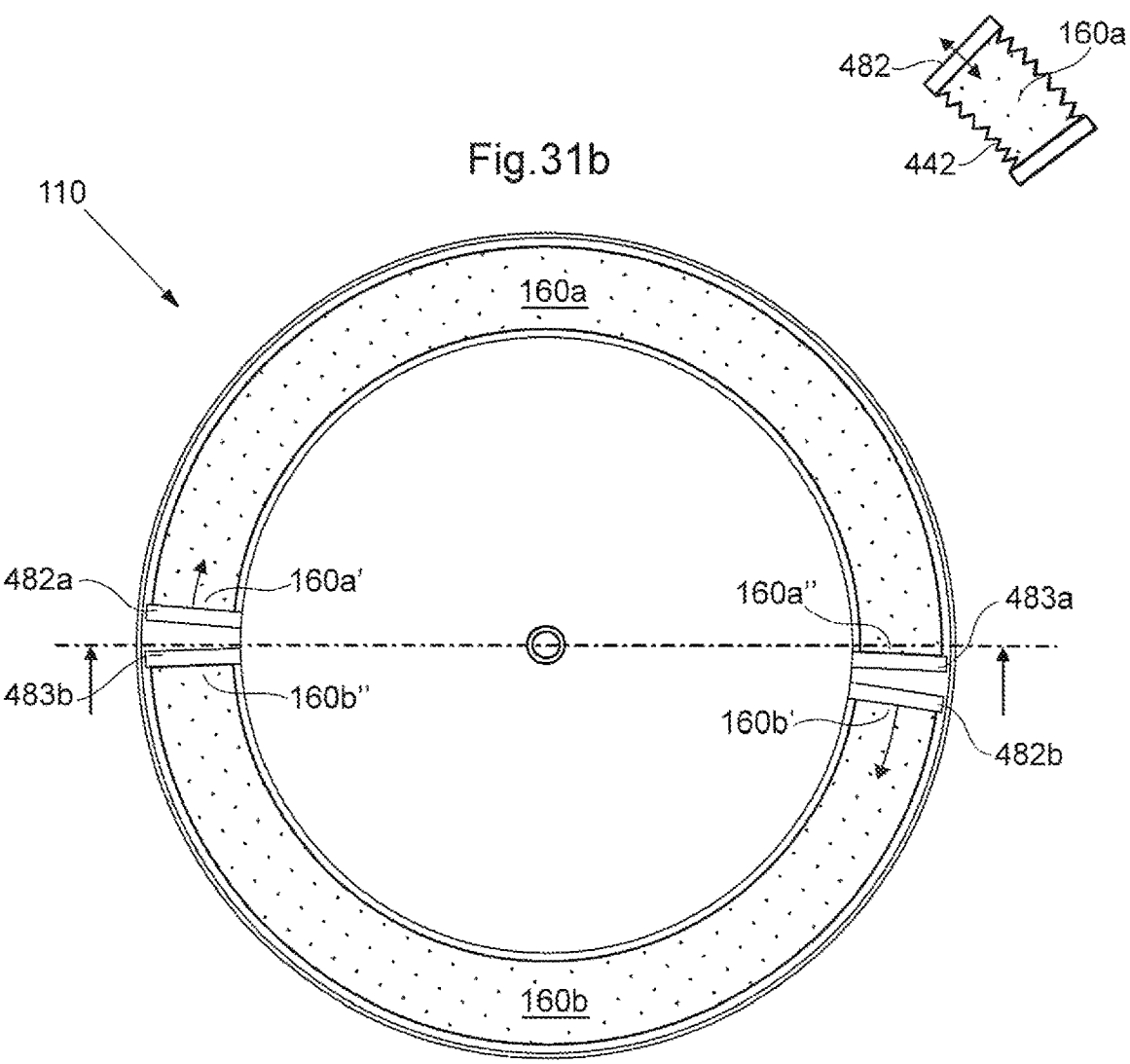

RESTRICTION DEVICE

This application is a continuation of PCT/EP2014/055112 filed 14 Mar. 2014, which claims priority from SE 1350319-8 filed Mar. 15, 2013, the entire contents of each of which are hereby incorporated by reference.

TECHNICAL FIELD

The present invention relates to medical implants. More specifically the invention relates to medical implants for restricting luminary organs.

BACKGROUND

Restricting a luminary organ of a patient may be damaging to the restricted organ, it would therefore be advantageous to have a restriction device adapted to restrict a luminary organ of the patient in a less damaging way than the devices of the prior art.

SUMMARY

A hydraulic implantable restriction device for restricting a luminary organ of a patient is provided. The hydraulic implantable restriction device comprises a first hydraulic restriction element adapted to restrict a first portion of the luminary organ, and a second hydraulic restriction element adapted to restrict a second portion of the luminary organ. The hydraulic implant further comprises a control unit adapted to control the first and second restriction elements for automatically switching between restricting the first and second portion of the luminary organ, for creating a less damaging restriction. The control unit may be adapted to automatically switch between restricting the first and second portion of the luminary organ on the basis of at least one of: a lapsed time being between 10 minutes and 6 months, and the patient using the function of the restricted luminary organ.

According to some embodiments, the implantable restriction device, may be adapted to restrict a luminary organ of the patient selected from a list consisting of: an intestine of the patient, a blood vessel of the patient, the urethra of the patient, the vas deference of the patient, the stomach of the patient, the esophagus of the patient, the anal sphincter, the cardia sphincter, the urinary sphincter and/or the oviducts of the patient.

The control signal may be a control signal generated on the basis of a sensor input, or may be a control signal transmitted from outside of the body of the patient.

The implantable hydraulic restriction device may further comprise an implantable fluid reservoir and a first fluid conduit connecting the fluid reservoir to the first restriction element, and a second fluid conduit connecting the fluid reservoir to the second restriction element. The implantable fluid reservoir may comprise at least one moveable wall portion for changing the volume of the implantable fluid reservoir and thereby moving fluid from the implantable fluid reservoir to the first and second restriction elements.

The implantable hydraulic restriction device may further comprise a hydraulic pump for pumping fluid from the implantable reservoir to at least one of the first and second restriction element. The hydraulic pump may be a hydraulic pump selected from: at least one reservoir acting as a pump by a wall of the reservoir moving, at least one reservoir acting as a pump by changing volume, at least one non-valve pump, at least one valve pump, at least one peristaltic pump, at least one membrane pump, at least one gear pump, and at least one bellows pump.

In one embodiment, the implantable hydraulic restriction device comprises an implantable valve member for directing fluid from the implantable reservoir to the first or second restriction element.

The implantable hydraulic restriction device may further comprise at least one motor for operating at least one of a movable wall portion and/or an implantable pump and/or an implantable valve member. The motor may be an electrical motor selected from: an alternating current (AC) electrical motor, a direct current (DC) electrical motor, a linear electrical motor, an axial electrical motor, a piezo-electric motor, a three-phase motor, a more than one-phase motor, a bimetal motor, and a memory metal motor.

According to one embodiment, the implantable hydraulic restriction device further comprises a gear system placed between the motor and at least one of a movable wall portion, an implantable pump, and an implantable valve member.

According to one embodiment, the gear system comprises an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear. The operable element may comprise at least one of; a planetary gear and a structure or wheel at least partly using friction to interconnect with the first gear.

According to one embodiment, the implantable hydraulic restriction device further comprises a threaded member arranged to move the wall portion of the reservoir. The threaded member may be connected to at least one of a motor of any of the embodiments herein, and a gear system of any of the embodiments herein. Such that a rotating force can be transferred to a reciprocating force for moving a wall portion.

The implantable hydraulic restriction device may further comprise an injection port for supplying fluid to the reservoir.

According to one embodiment, the implantable hydraulic restriction device further comprises a servo connected between the motor and at least one of the: a movable wall portion, an implantable pump, and an implantable valve member.

According to one embodiment, at least one of the first and second restriction elements is elongated and adapted to form a closed loop around the portion of the luminary organ.

The hydraulic pump in any of the embodiments herein may be a peristaltic hydraulic pump. The hydraulic peristaltic pump may comprise a hollow member for fluid transportation, and an operable compression member adapted to engage and compress the hollow member, and the compression member is in direct or indirect connection with the motor such that motor operates the compression member such that fluid is transported in the hollow member.

According to one embodiment, the hollow member of the peristaltic pump forms a loop or part of a loop adapted to at least partially encircle at least one of the gear system and the motor in at least partially the same axial plane. The motor is adapted to propel the compressing member such that the compression member compresses the hollow member towards the outer periphery of the loop or part of loop.

According to one embodiment, the movement of the movable wall portion of the fluid reservoir by the threaded member in a first direction moves fluid from the fluid reservoir to the first hydraulic restriction element. Movement of the movable wall portion of the fluid reservoir by the threaded member in a second direction moves fluid from the fluid reservoir to the second hydraulic restriction element.

The implantable hydraulic restriction device may further comprise an implantable energizing unit for providing energy to any energy consuming components of the device to be implanted in the patient.

According to one embodiment, the implantable hydraulic restriction device further comprises a wireless energy receiver, adapted to receive wireless energy from a wireless energy transmission device transmitting wireless energy from outside the patient's body to any energy consuming implantable component and/or the implantable energizing unit.

The implantable hydraulic restriction device may further comprise a wireless energy transmission for wireless transfer of energy from outside the patient's body to any energy consuming implantable component of the device and/or an implantable energizing unit.

The implantable hydraulic restriction device may further comprise a first implantable fluid reservoir and a first fluid conduit connecting the fluid reservoir to the first restriction element, and a second implantable fluid reservoir, a second fluid conduit connecting the second fluid reservoir to the second restriction element. According to one embodiment, the second fluid reservoir comprises a dividing part of the first reservoir.

According to one embodiment of the implantable hydraulic restriction device at the implantable first reservoir comprises at least one moveable wall portion for changing the volume of the implantable first fluid reservoir and thereby moving fluid from the implantable first fluid reservoir to the first elements. According to one embodiment of the implantable hydraulic restriction device, the implantable second reservoir comprises at least one moveable wall portion for changing the volume of the implantable second fluid reservoir and thereby moving fluid from the implantable second fluid reservoir to the second elements.

The at least one moveable wall portion may be adapted to change the volume of both the first and second fluid reservoirs for changing the volume to; increase the volume of the implantable first fluid reservoir, when the volume of the implantable second fluid reservoir is decreasing, and increase the volume of the implantable first fluid reservoir, when the volume of the implantable second fluid reservoir is decreasing, thereby moving fluid.

The implantable hydraulic restriction device may further comprise a hydraulic pump for pumping fluid from the first implantable reservoir to the first restriction element and/or a hydraulic pump for pumping fluid from the second implantable reservoir to the second restriction element, and/or a hydraulic pump for pumping fluid between the first and second implantable reservoir.

According to one embodiment, the implantable first and second fluid reservoirs are divided by at least one moveable piston for changing the volume of the implantable fluid reservoirs and thereby increasing fluid in the first fluid reservoir simultaneously with decreasing fluid in the second fluid reservoir and vice versa.

The control signal in any of the embodiments herein may be a control signal coming from outside the body to control the device, consisting of at least one of; a signal that overrides the automatic switching, an automatic executed signal, or a programming signal to program the terms for the automatic switching.

The control signal in any of the embodiments herein may be a control signal generated inside the body, to control the device, comprising at least one of; a signal that overrides the automatic switching, an automatic executed signal, a measured parameter, a calculated parameter, a functional parameter of the device, a physiological or physical parameter of the patient, and an input from any sensor.

A hydraulic implantable restriction device for restricting a luminary organ of a patient is provided. The hydraulic implantable restriction device comprises a first hydraulic restriction element adapted to restrict a first portion of the luminary organ, and a second hydraulic restriction element adapted to restrict a second portion of the luminary organ, and a control unit adapted to control the first and second restriction elements for automatically switching between restricting the first and second portion of the luminary organ, for creating a less damaging restriction. The control unit is adapted to automatically switch between restricting the first and second portion of the luminary organ on the basis of the receipt of a control signal.

According to one embodiment the control signal is a control signal coming from outside the body, consisting of at least one of; a signal that overrides the automatic switching, an automatic executed signal, or a programming signal for programming the terms for the automatic switching.

According to one embodiment, the control signal consists of a signal generated inside the body, comprising at least one of; a signal that overrides the automatic switching, an automatic executed signal, a measured parameter, a calculated parameter, a functional parameter of the device, a physiological or physical parameter of the patient, and an input from any sensor.

The implantable hydraulic restriction device may be adapted to restrict a luminary organ of the patient selected from a list consisting of: an intestine of the patient, a blood vessel of the patient, the urethra of the patient, the vas deference of the patient, the stomach of the patient, the esophagus of the patient, the anal sphincter, the cardia sphincter, the urinary sphincter and/or the oviducts of the patient.

According to one embodiment of the implantable hydraulic restriction device, the receipt of a control signal comprises the receipt of a control signal generated on the basis of a sensor input.

According to one embodiment, the control signal is transmitted from outside of the body of the patient.

The implantable hydraulic restriction device may further comprise an implantable fluid reservoir and a first fluid conduit connecting the fluid reservoir to the first restriction element, and a second fluid conduit connecting the fluid reservoir to the second restriction element.

The implantable fluid reservoir in any of the embodiments herein may comprise at least one moveable wall portion for changing the volume of the implantable fluid reservoir and thereby move fluid from the implantable fluid reservoir to the first and second restriction elements.

According to one embodiment, the implantable hydraulic restriction device further comprises a hydraulic pump for pumping fluid from the implantable reservoir to at least one of the first and second restriction element.

The hydraulic pump may be a hydraulic pump selected from: at least one reservoir acting as a pump by a wall of the reservoir moving, at least one reservoir acting as a pump by changing volume, at least one non-valve pump, at least one valve pump, at least one peristaltic pump, at least one membrane pump, at least one gear pump, and at least one bellows pump.

According to one embodiment, the implantable hydraulic restriction device further comprises an implantable valve member for directing fluid from the implantable reservoir to the first or second restriction element.

According to one embodiment, the implantable hydraulic restriction device further comprises at least one motor for operating at least one of: a movable wall portion, an implantable pump, and an implantable valve member.

According to one embodiment, the motor comprises an electrical motor selected from: an alternating current (AC) electrical motor, a direct current (DC) electrical motor, a linear electrical motor, an axial electrical motor, a piezo-electric motor, a three-phase motor, a more than one-phase motor, a bimetal motor, and a memory metal motor.

According to one embodiment, the implantable hydraulic restriction device further comprises a gear system placed between the motor and at least one of: a movable wall portion, an implantable pump, and an implantable valve member.

The gear system of the implantable hydraulic restriction device, in any of the embodiments herein may comprise: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged. The operation of the operable element advances the positions and thereby causes relative rotation between the first gear and the second gear. The operable element may comprise at least one of; a planetary gear and a structure or wheel at least partly using friction to interconnect with the first gear.

According to one embodiment, the implantable hydraulic restriction device further comprises a threaded member arranged to move the wall portion of the reservoir. The threaded member may be connected to a motor and/or a gear system for transferring a rotating force to a reciprocating force for moving the wall portion.

The implantable hydraulic restriction device may further comprise an injection port for supplying fluid to the reservoir.

According to one embodiment, the implantable hydraulic restriction device further comprises a servo connected between the motor and at least one of the: a movable wall portion, an implantable pump, and an implantable valve member.

According to one embodiment, at least one of the first and second restriction elements is elongated and adapted to form a closed loop around the portion of the luminary organ.

The hydraulic pump in any of the embodiments may be a peristaltic hydraulic pump comprising a hollow member for fluid transportation, and an operable compression member adapted to engage and compress the hollow member. The compression member is in direct or indirect connection with the motor such that motor operates the compression member such that fluid is transported in the hollow member.

The hollow member may form a loop or part of a loop adapted to at least partially encircle at least one of the gear system and the motor in at least partially the same axial plane. The motor may be adapted to propel the compressing member such that the compression member compresses the hollow member towards the outer periphery of the loop or part of loop.

According to one embodiment, the movement of the movable wall portion of the fluid reservoir by the threaded member in a first direction moves fluid from the fluid reservoir to the first hydraulic restriction element, and the movement of the movable wall portion of the fluid reservoir by the threaded member in a second direction moves fluid from the fluid reservoir to the second hydraulic restriction element.

The implantable hydraulic restriction device may further comprise an implantable energizing unit for providing energy to any energy consuming components of the device to be implanted in the patient.

According to one embodiment, the implantable hydraulic restriction device further comprises a wireless energy receiver adapted to receive wireless energy from a wireless energy transmission device transmitting wireless energy from outside the patient's body to any energy consuming implantable component of the device and/or the implantable energizing unit.

According to one embodiment, the implantable hydraulic restriction device comprises a wireless energy transmission for wireless transfer of energy from outside the patient's body to any energy consuming implantable component of the device and/or to the implantable energizing unit.

The implantable hydraulic restriction device may further comprise a first implantable fluid reservoir and a first fluid conduit connecting the fluid reservoir to the first restriction element, and a second implantable fluid reservoir, a second fluid conduit connecting the second fluid reservoir to the second restriction element. The second fluid reservoir may comprise a dividing part of the first reservoir.

According to one embodiment, the implantable first reservoir comprises at least one moveable wall portion for changing the volume of the implantable first fluid reservoir and thereby moving fluid from the implantable first fluid reservoir to the first elements.

According to one embodiment, the implantable second reservoir comprises at least one moveable wall portion for changing the volume of the implantable second fluid reservoir and thereby moving fluid from the implantable second fluid reservoir to the second elements.

The at least one moveable wall portion may be adapted to change the volume of both the first and second fluid reservoirs for changing the volume to; increase the volume of the implantable first fluid reservoir, when the volume of the implantable second fluid reservoir is decreasing, and increase the volume of the implantable first fluid reservoir, when the volume of the implantable second fluid reservoir is decreasing, thereby moving fluid.

According to one embodiment. the implantable hydraulic restriction device further comprises at least one of; a hydraulic pump, for pumping fluid from the first implantable reservoir to the first restriction element, a hydraulic pump, for pumping fluid from the second implantable reservoir to the second restriction element, and a hydraulic pump, for pumping fluid between the first and second implantable reservoir.

According to one embodiment, the implantable first and second fluid reservoirs may be divided by at least one moveable piston for changing the volume of the implantable fluid reservoirs and thereby increasing fluid in the first fluid reservoir simultaneously with decreasing fluid in the second fluid reservoir and vice versa.

The energizing the restriction device the device could further comprise a wireless energy receiver receiving energy by at least one wireless energy signal, such as a wave signal, e.g. a sound wave signals, ultrasound wave signals, electromagnetic wave signals, infrared light signals, visible light signals, ultra violet light signals, laser light signals, micro wave signals, radio wave signals, x-ray radiation signals and a gamma radiation signals. The wireless energy signal could further comprise an electric or magnetic field, or a combined electric and magnetic field.

According to yet another embodiment the device comprises an energizing unit adapted to power the device, which could comprise an internal energy source which in turn could be adapted to receive energy from an external energy source transmitting energy in a wireless mode. The internal energy source could further comprise an accumulator, at least one voltage level guard and/or at least one constant current guard. The device could further comprise an energy-transforming device adapted to transform energy from a first form into a second form.

Some of the embodiments of the present invention relates to an anal incontinence treatment apparatus for treatment of a patient, who suffers from anal incontinence, or a treatment apparatus for stoma patients comprising an adjustable restriction device implantable in the patient for engaging a portion of; the anus, colon or rectum of the patient to restrict a faecal passageway therein or an intestinal stoma, the large or small intestine, and an operable adjustment device implantable in the patient for adjusting the restriction device to change the restriction of the faecal passageway or the intestinal stoma. The restriction device as being referred to in the whole document have the definition as follows: The restriction device: is a device comprising two restriction devices that automatically switch the restriction between themselves.

What is referred to as presenting anal incontinence will in every applicable way also apply to the intestinal stoma. Even other type of stoma for example such as stomach, urine bladder etc will also apply to the presentation herein.

Furthermore, the anal incontinence treatment apparatus is used as an example product and the treatment usage options referred to herein as well as any other possible application inside the body, will in any applicable way also apply to all these alternatives. In this case we focus on both mechanical and hydraulic restriction devices, however, with main focus on mechanical solutions as an example for all other threatment fields and embodiments.

Anal incontinence is a wide-spread disease. Several kinds of sphincter plastic surgery are used today to remedy anal incontinence. There is a prior manually operated sphincter system in an initial clinical trial phase where a hydraulic sphincter system connected to an elastic reservoir (balloon) placed in the scrotum is developed. A disadvantage of this system is that thick, hard fibrosis is created around the reservoir by pump movements making the system useless sooner or later. Another disadvantage is that the use of hydraulic fluid always entails a risk of fluid leaking from the implanted hydraulic system.

A prime object of the present invention is to provide an anal incontinence treatment apparatus in which the risk of liquid leaking from hydraulic components of the apparatus implanted in the patient's body is substantially reduced or completely eliminated.

A further object of the invention is to provide an anal incontinence or stoma treatment apparatus, which does not require a manual manipulation of a combined reservoir and pump mechanism implanted in the scrotum or labia majora region of the patient.

These objects are obtained by an apparatus of the kind stated initially characterised in that the adjustment device is adapted to mechanically adjust the restriction device.

The adjustment device may be non-manually operated, i.e. the adjustment device may be operated by any powered operation device, not manipulated by touching the skin of the patient. Preferably, the adjustment device is adapted to adjust the restriction device in a non-invasive manner.

The adjustment device may adjust the restriction device in a non-thermal manner or in a non-magnetic manner, i.e. magnetic forces may not be involved when adjusting the restriction device.

The restriction device preferably is adapted to control, suitably steplessly, the cross-sectional area of the faecal passageway, i.e. to open and close the faecal passageway.

In the various embodiments hereinafter described the restriction device generally forms an at least substantially closed loop. However, the restriction device may take a variety of different shapes, such as the shape of a square, rectangle or ellipse. The substantially closed loop could for example be totally flat, i.e. thin as seen in the radial direction. The shape of restriction device may also be changed during use, by rotation or movements of the restriction device in any direction.

A physical lumen, like the small intestine, anal channel colon or rectum, is often easier to restrict by contracting at least two opposite or different side walls of the lumen against each other. The expression "colon or rectum should be understood to mean the rectum extended all the way out to the anal sphincter and following the passage of the large intestine in the other direction.

The restriction device may comprise an adjustable cuff, a clamp or a roller for bending the colon or rectum to restrict the faecal passageway therein. Such a cuff, clamp or roller may also be utilized for squeezing the colon or rectum against human material inside the body of the patient for an example the sacral bone of the patient.

Preferably, the restriction device comprises an elongated restriction member and forming means for forming the restriction member into at least a substantially closed loop around the portion of the colon or rectum, wherein the loop defines a restriction opening, whereby the adjustment device adjusts the restriction member in the loop to change the size of the restriction opening.

The restriction device may be designed for implantation in the abdomen or retroperitoneum of the patient and preferably may engage the colon or rectum.

The adjustment device may be incorporated in the restriction device as well as controlled by hydraulic means.

In accordance with a preferred first adjustment principle, the adjustment device mechanically adjusts the longitudinal extension of the elongated restriction member in a loop form.

In a preferred embodiment of the invention utilizing the first adjustment principle, the restriction member comprises a main portion and two elongated end portions, and the adjustment device establishes longitudinal relative displacement between the end portions of the restriction member, so that the size of the restriction opening is adjusted. The forming means may comprise any suitable known or conventional device capable of practising the desired function, such as a spring material forming the elongated restriction member into the loop, so that the restriction opening has a predetermined size, and the adjustment device may adjust the restriction member against the spring action of the spring material. In other words, the restriction member may comprise a spring clip. The spring material may be integrated in the restriction member.

Preferably, the adjustment device comprises a movement transferring member, suitably a drive wheel, in engagement with at least one of the end portions of the restriction member and operable to displace the one end portion relative to the other end portion of the restriction member. The drive wheel may advantageously be in engagement with both of the end portions of the restriction member and be operable to displace said end portions relative to each other. An elongated flexible drive shaft may be operatively connected to the drive wheel, for transferring manual or motor generated power from a location remote from the restriction member. In its simplest embodiment, the drive wheel may comprise a pulley in frictional engagement with the restriction member. As an alternative, a gear rack may be formed on at least one of the end portions of the restriction member and the drive wheel may comprise a gear wheel in mesh with the gear rack. Other suitable known or conventional mechanisms may also or alternatively be used as the adjustment device.

The movement transferring member may alternatively comprise at least one cylinder and a piston, which is movable therein and is connected to one of the end portions of the restriction member, the piston being operable to longitudinally displace the one end portion of the restriction member relative to the other end portion of the restriction member. Alternatively, the movement transferring means may comprise two interconnected cylinders and two pistons in the respective cylinders connected to said end portions, respectively, of the restriction member, the pistons being operable to longitudinally displace the end portions of the restriction member relative to each other. Other known or conventional devices also or alternatively can be used as the movement transferring member.

A motor, which is fixed relative to the main portion of the restriction member and has a rotating drive shaft operatively connected to the movement transferring member, may be positioned relative to the elongated restriction member such that the drive shaft extends transverse thereto. Alternatively, the motor may be positioned relative to the elongated restriction member such that the drive shaft extends substantially tangentially to the loop of the restriction member.

In another embodiment of the invention utilizing the first adjustment principle, the elongated restriction member is longitudinally resilient and the adjustment device comprises a contraction device for longitudinally contracting the resilient restriction member. Preferably, the elongated restriction member comprises a substantially nonresilient main portion and an end portion forming an elongated helical spring, which is contractible by the contraction device. The contraction device may suitably comprise an elongated flexible pulling member connected to the main portion of the restriction member and extending through the helical spring to contract the helical spring against an arresting member, which is fixed relative to the main portion of the restriction member. The pulling member may extend in an elongated tube joined at one end thereof to the arresting member, so that a motor remote from the restriction member may be attached to the other end of the elongated tube and pulls the pulling member through the tube to contract the helical spring.

In yet another embodiment of the invention utilizing the first adjustment principle, the elongated restriction member comprises an elongated helical spring having a free end, and a body to which the spring is nonrotatably secured at its opposite end. The adjustment device rotates the helical spring in one direction to enlarge the coils of the helical spring to longitudinally contract the spring and to rotate the spring in the opposite direction to reduce the size of the coils of the spring to longitudinally extend the spring. As a preferred alternative, the restriction member comprises a further elongated helical spring having a free end and nonrotatably secured to the body at its opposite end, and the adjustment device comprises a drive shaft having two opposite end portions connected to the springs, respectively, at their free ends, the helical coils forming left and right hand helices, respectively. The adjustment device may alternatively comprise a gearing having an input shaft and two opposite aligned output shafts connected to the helical springs, respectively, at their free ends, the input shaft being connected to said output shafts so that the output shafts rotate in the opposite directions upon rotation of the input shaft, the helical coils forming the same helices.

In accordance with a second adjustment principle, the adjustment device mechanically adjusts the restriction member so that at least a portion of a radially innermost circumferential confinement surface formed by the restriction member is substantially radially displaced.

In one embodiment of the invention utilizing the second adjustment principle, the restriction member comprises an elongated voltage responsive element forming part of the confinement surface and capable of bending into a bow in response to a voltage applied across the element, the radius of curvature of the bow being adjustable by changing the level of the voltage.

In another embodiment of the invention utilizing the second adjustment principle, the adjustment device changes the diameter of an elastic annular element of the restriction member, which forms the confinement surface. Preferably, the forming means comprises a substantially rigid outer annular element coaxially surrounding the elastic annular element, and the adjustment device comprises means for pulling the elastic annular element radially outwardly towards the outer annular element to expand the elastic annular element. For example, the pulling means may comprise a plurality of threads secured to the elastic annular element along the circumference thereof and running from the elastic annular element via guide members attached to the outer annular element.

In yet another embodiment of the invention utilizing the second adjustment principle, the forming means comprises a substantially rigid outer annular element, and the restriction member comprises an elongated helical spring extending internally along the outer annular element and contacting the latter. The helical spring forms part of the circumferential confinement surface and has a free end. The restriction member further comprises a body to which the spring is nonrotatably secured at its opposite end. The adjustment device rotates the helical spring in one direction to enlarge the coils of the spring to contract the circumferential confinement surface and rotates the spring in the opposite direction to reduce the size of the coils of the spring to expand the circumferential confinement surface. As an alternative, which is preferred, the restriction member comprises two elongated helical springs forming part of the circumferential confinement surface and connected to the body of the restriction member. The adjustment device rotates each spring in one direction to enlarge the coils of the spring to contract the circumferential confinement surface and rotates the spring in the opposite direction to reduce the size of the coils of the spring to expand the circumferential confinement surface.

In accordance with a third adjustment principle, the restriction member comprises at least two separate elements, at least one of which is pivoted so that it may turn in a plane in which the restriction member extends, and the adjustment device turns the pivoted element to change the size of the restriction opening. Preferably, the restriction member comprises a plurality of separate pivoted elements disposed in series, each pivoted element being pivoted in the plane, and the adjustment device turns all of the pivoted elements to change the size of the restriction opening. For example, the pivoted elements may comprise lamellae arranged like the conventional adjustable aperture mechanism of a camera.

In accordance with a fourth adjustment principle, the adjustment device folds at least two foldable frame elements of the restriction member towards each other. Preferably, the foldable frame elements comprise two substantially or partly semi-circular frame elements which are hinged together so that the semi-circular elements are swingable relative to each other from a fully open state in which they form part of a circle to a fully folded state in which they form part of a semi-circle. The same principal may be used with the swingable parts mounted together in one end and not in the other end. Alternatively, the restriction device may comprises two preferable rigid articulated clamping elements positioned on opposite or different sides of the colon or rectum, and the adjustment device turns the clamping elements toward each other to clamp the colon or rectum between the clamping elements, thereby restricting the faecal passageway in the colon or rectum.

In accordance with a fifth adjustment principle, the adjustment device turns the restriction member around a longitudinal extension thereof, the elongated restriction member being elastic and varying in thickness as seen in a cross-section therethrough. Suitably, the elongated restriction member comprises an elastic belt.

In accordance with a sixth adjustment principle, the adjustment device changes the size of the restriction opening such that the outer circumferential confinement surface of the restriction member is changed.

In accordance with a seventh adjustment principle, the adjustment device changes the size of the restriction opening such that the outer circumferential confinement surface of the restriction member is unchanged.

In accordance with an eighth adjustment principle, the elongated restriction member may be flexible, and the adjustment device pulls a first portion of the flexible restriction member from a second portion of the flexible restriction member opposite the first portion in the loop to squeeze the colon or rectum between the opposite lengths of the elongated flexible restriction member to restrict the faecal passageway in the colon or rectum.

In accordance with a ninth adjustment principle, the restriction device comprises at least two elements on opposite or different sides of the colon or rectum, and the adjustment device decreases the distance between the elements to squeeze the colon or rectum between the elements, thereby restricting the faecal passageway in the colon or rectum. It is also possible to use only one element and squeeze the colon or rectum against human bone or tissue.

The elements above may as well as all the restriction members mentioned in this application be everything from rigid to soft.

In accordance with a tenth adjustment principle, the restriction device bends or rotates a portion of colon or rectum to restrict the faecal passageway in the same. For example, the restriction device may comprise at least two bending members, such as cylindrical or hour-glass shaped rollers, positioned on opposite or different sides of the colon or rectum and displaced relative to each other along the colon or rectum, and the adjustment device may move the bending members against the colon or rectum to bend it to restrict the faecal passageway in the colon or rectum. Suitably, the displacement members may comprise rollers. The restriction device may also rotate a portion of the colon or rectum. The bending or rotating members may have any shape or form and be either hydraulic or non-inflatable.

Alternatively, the two bending members one placed more distal than the other may be rotated in opposite direction relative to each other. With interconnecting material for example flexible bands between the holding members a restriction will occur between the bending members when they are rotated.

The restriction device may in all applicable embodiments take any shape and be either hydraulic or non-inflatable.

In all of the above-described embodiments of the invention the adjustment device is conveniently operated by an operation device, which may comprise a servo means and/or a motor, preferably a reversible electric motor. The motor may be fixed directly to or be placed in association with the restriction device, or alternatively be located remote from the restriction device, advantageously in the abdomen or pelvic region or subcutaneously or in the retroperitoneum of the patient. In the latter alternative the motor is advantageously connected to the adjustment device by a flexible power transmission conduit to permit a suitable positioning of the motor in the abdomen of the patient. The motor may be manually activatable, for example by an implanted switch.

In some of the above described embodiments of the invention, however, the adjustment device may conveniently be operable by a hydraulic operation device, which preferably is manually activatable. The hydraulic operation device may advantageously include a hydraulic servo to facilitate manual activation. As an alternative, the hydraulic operation device may be powered by an electric motor, which may be manually activatable or controlled by remote control means. The components of such a hydraulic operation device may be placed in association with the restriction device and/or be located at a suitable place in the abdomen or be implanted subcutaneously.

More specifically, a reservoir may be provided containing a predetermined amount of fluid for supplying the hydraulic operation device with fluid. The reservoir defines a chamber for the predetermined amount of fluid and the hydraulic operation device changes the volume of the chamber. The hydraulic operation device may comprise first and second wall portions of the reservoir, which are displaceable relative to each other to change the volume of the chamber of the reservoir. The first and second wall portions of the reservoir may be designed to be displaceable relative to each other by manual manipulation thereof, preferably to permit manual pushing, pulling or rotation of any of the wall portions in one direction. Alternatively, the wall portions may be displaceable relative to each other by magnetic means (such as a permanent magnet and magnetic material reed switch, or other known or conventional magnetic devices), hydraulic means or electrical control means such as an electric motor. The magnetic means, hydraulic means, or electrical control means may all be activated by manual manipulation, preferably using a subcutaneously located manually manipulatable means. This control may be indirect, for example via a switch.

The hydraulic operation device may operate the adjustment device with fluid from the reservoir in response to a predetermined first displacement of the first wall portion of the reservoir relative to the second wall portion of the reservoir, to adjust the restriction device to open the faecal passageway, and to operate the adjustment device with fluid from the reservoir in response to a predetermined second displacement of the first wall portion of the reservoir relative to the second wall portion of the reservoir, to adjust the restriction device to close the faecal passageway. In this embodiment, no pump is used, only the volume of the reservoir is varied. This is of great advantage compared to the solution described below when a pump is used to pump fluid between the reservoir and the adjustment device because there is no need for a non-return valve and it is still possible to have fluid going both to and from the reservoir.

As an alternative, the hydraulic operation means may comprise a pump for pumping fluid between the reservoir and the adjustment device. The pump may pump fluid both to and away from the adjustment device. A mechanical manual solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated manually, mechanically, electrically, magnetically, or hydraulically. Any kind of motor could of course be used for all the different operations as well as wireless remote solutions. The pump may comprise a first activation member for activating the pump to pump fluid from the reservoir to the adjustment device and a second activation member for activating the pump to pump fluid from the adjustment device to the reservoir. The activation members may be operable by manual manipulation, preferably to permit manual pushing, pulling or rotating thereof in one direction. Suitably, at least one of the activation members is adapted to operate when subjected to an external pressure exceeding a predetermined magnitude.

Alternatively, at least one of the first and second activating members may be operable by magnetic means, hydraulic means or electrical control means such as an electric motor. The magnetic means, hydraulic means, or electrical control means may all be activated by manual manipulating means preferably located subcutaneously. This activation may be indirect, for example via a switch.

Advantageously, especially when manual manipulation means are used, a servo means could be used. With servo means less force is needed for operating the adjustment device. The term "servo means" encompasses the normal definition of a servo mechanism, i.e. an automatic device that controls large amounts of power by means of very small amounts of power, but may alternatively or additionally encompass the definition of a mechanism that transfers a weak force acting on a moving element having a long stroke into a strong force acting on another moving element having a short stroke. The servo means may comprise a motor, preferably an electric motor, which may be reversible.

Alternatively, a reverse servo may be employed. The term "reverse servo" is to be understood as a mechanism that transfers a strong force acting on a moving element having a short stroke into a weak force acting on another moving element having a long stroke; i.e. the opposite function of the above-defined alternative mechanism of a normal servo mechanism. A first closed hydraulic system that controls another closed hydraulic system in which hydraulic means of the adjustment device is incorporated may be used. Minor changes in the amount of fluid in a smaller reservoir of the first system could then be transferred by the reverse servo into major changes in the amount of fluid in a larger reservoir in the second system. In consequence, the change of volume in the larger reservoir of the second system affects the hydraulic means of the adjustment device. For example, a short stroke that decreases the volume of the smaller reservoir will cause the larger reservoir to supply the adjustment device with a large amount of hydraulic fluid, which in turn results in a long mechanical adjustment stroke on the restriction device. The great advantage of using such a reverse servo is that the larger volume system could be placed inside the abdomen or retroperitoneum where there is more space and still it would be possible to use manual manipulation means of the smaller system subcutaneously. The smaller reservoir could be controlled directly or indirectly by a fluid supply means. The fluid supply means may include another small reservoir, which may be placed subcutaneously and may be activated by manual manipulation means. Both the servo and reverse servo may be used in connection with all of the various components and solutions described in the present specification.

Preferably, the reverse servo comprises hydraulic means and a main fluid supply reservoir and eventually an additional fluid supply reservoir. Both reservoirs define a chamber containing hydraulic fluid, and the hydraulic means comprises first and second wall portions of the main fluid supply reservoir, which are displaceable relative to each other to change the volume of the chamber of the main fluid supply reservoir. The hydraulic means may control the adjustment device indirectly, e.g. via an increased amount of fluid in the main fluid supply reservoir, in response to a predetermined first displacement of the first wall portion of any of the reservoirs relative to the second wall portion of the reservoir to close the faecal passageway, and to control the adjustment device in response to a second displacement of the first wall portion of any reservoir relative to the second wall portion, to indirectly adjust the restriction device to open the faecal passageway. The wall portions of the reservoirs may be designed to be displaceable relative to each other by manual manipulation thereof or be displaceable relative to each other by manually pushing, pulling or rotating any of the wall portions of the reservoir in one direction. Alternatively, the wall portions of the main fluid supply reservoir may be displaceable relative to each other by magnetic means, hydraulic means or electric control means including an electric motor.

The magnetic means, hydraulic means, or electrical control means may all be activated by manually manipulated means preferably located subcutaneously. This control may be indirect for example via a switch.

Even in the broadest embodiment of the invention the adjustment device may comprise a servo means. The servo means may comprise a hydraulic operation means, an electrical control means, a magnetic means, mechanical means or a manual manipulation means. The hydraulic operation means, electrical control means, mechanical means or magnetic means may be activated by manual manipulating means. Using a servo system will save the use of force when adjusting the adjustment device, which may be of importance in many applications, for example when a battery cannot put out enough current although the total energy in the battery is more than enough to power the system.

In accordance with a preferred embodiment of the invention, the apparatus comprises implantable electrical components including at least one, or only one single voltage level guard and a capacitor or accumulator, wherein the charge and discharge of the capacitor or accumulator is controlled by use of the voltage level guard. As a result, there is no need for any implanted current detector and/or charge level detector for the control of the capacitor, which makes the apparatus simple and reliable.

All solutions may be controlled by a wireless remote control for controlling the adjustment device. The remote control may advantageously be capable of obtaining information related to the faecal passageway or the pressure against the restriction device or colon or rectum or other important physical parameters and of commanding the adjustment device to adjust the restriction device in response to obtained information. With the wireless remote control the apparatus of the invention is conveniently controlled by the patient when he so desires, which is of great advantage compared to the prior art procedures. With the remote control the apparatus of the invention is conveniently controlled to adjust the implanted restriction device to release the faecal passageway when the patient wants to relieve himself or herself.

The apparatus may further comprise a pressure sensor for directly or indirectly sensing the pressure against the restriction device and the restriction device may control the blood flow in response to signals from the pressure sensor. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor. The adjustment device preferably non-invasively adjusts the restriction device to change the size of the cross-sectional area.

The adjustment device and/or other energy consuming components of the apparatus may be energised with wirelessly transmitted energy from outside the patient's body or be powered by an implanted battery or accumulator.

The apparatus may further comprise an implanted energy transforming device for transferring wireless energy directly or indirectly into kinetic energy for operation of the restriction device. The energy transforming device may, preferably directly, transform the wireless energy in the form of sound waves into electric energy for operation of the restriction device. Suitably the energy transforming device comprises a capacitor adapted to produce electric pulses from the transformed electric energy.

The apparatus of the invention may further comprise an energy transfer means for wireless transfer of energy from outside the patient's body to the adjustment device and/or other energy consuming implantable components of the apparatus. The energy transfer means may be adapted to intermittently transfer the energy, preferably electric energy, in the form of a train of energy pulses for direct use in connection with the energising of the energy consuming components of the apparatus. An implanted capacitor having a capacity less than 0.1 µF may be used for producing the train of energy pulses.

A motor may be implanted for operating the adjustment device, wherein the energy transfer means is adapted to directly power the motor with transferred energy. Alternatively, or in combination with the motor, a pump may be implanted for operating the adjustment device, wherein the energy transfer means is adapted to transfer wireless energy in the form of electromagnetic waves for direct power of the pump. Preferably, the pump is not a plunger type of pump, but may comprise a peristaltic or membrane pump.

The energy transfer means preferably transfers wireless energy in the form of electromagnetic waves. However, for safety radio waves may be excluded.

Alternatively, the energy transferred by the energy transfer means may comprise an electric field or a magnetic field.

Most preferred, the energy transferred by the energy transfer means comprises a signal.

Preferably, the wireless remote control comprises a separate signal transmitter or receiver and a signal receiver or transmitter implanted in the patient. For example, the signal transmitter and signal receiver may transmit and receive a signal in the form of digital pulses, which may comprise a magnetic or electric field. Alternatively, which is preferred, the signal transmitter and signal receiver may transmit and receive an electromagnetic wave signal, a sound wave signal or a carrier wave signal for a remote control signal. The receiver may comprise an implanted control unit for controlling the adjustment device in response to a control signal from the signal transmitter.

The apparatus of the invention may further comprise an implanted energiser unit for providing energy to energy consuming implanted components of the apparatus, such as electronic circuits and/or a motor for operating the adjustment device. The apparatus may comprise an external energy transmitter for transmitting wireless energy, wherein the energiser unit is adapted to transform the wireless energy into electric energy. An implanted electric motor may operate the adjustment device and the energiser unit may be adapted to power the electric motor with the electric energy transformed from the wireless energy.

The energiser unit may comprise a battery and a switch operable by the wireless energy transmitted by the external transmitter, for connecting the battery to the implanted energy consuming components of the apparatus in an "on" mode when the switch is powered by the wireless energy and to keep the battery disconnected from the energy consuming components in a "standby" mode when the switch is not powered.

The control unit may power such an implanted motor with energy provided by the energiser unit in response to a control signal received from the signal transmitter. Any known or conventional signal transmitter or signal receiver that is suitable for use with a human or mammal patient may be provided as the signal transmitter or signal receiver of the invention.

Generally, all of the above signals may comprise electromagnetic waves, such as infrared light, visible light, laser light, micro waves, or sound waves, such as ultrasonic waves or infrasonic waves, or any other type of wave signals. The signals may also comprise electric or magnetic fields, or pulses. All of the above-mentioned signals may comprise digital signals. The signals may be carried by a carrier wave signal, which in an alternative embodiment may be the same signal as the wireless energy signal. Preferably a digital control signal may be carried by an electromagnetic wave signal. The carrier wave or control signal may be amplitude or frequency modulated.

The motor may be any type of motor, such as a pneumatic, hydraulic or electric motor and the energiser unit may power the motor with pressurized gas or liquid, or electric energy, depending on the type of motor. Where the motor is an electric motor, it may power pneumatic or hydraulic equipment.

The energiser unit may comprise a power supply and the control unit may power the motor with energy from the power supply. Preferably, the power supply is an electric power supply, such as a battery, and the motor is an electric motor. In this case, the battery also continuously powers at least part of the circuitry of the signal receiver in a standby mode between the adjustments, in order to keep the signal receiver prepared for receiving signals transmitted from the signal transmitter.

The energiser unit may transform energy from the control signal, as the control signal is transmitted to the signal receiver, into electric energy for powering the implanted electronic components. For example, the energiser unit may transform the energy from the control signal into a direct or alternating current.

In case there is an implanted electric motor for operating the adjustment device the energiser unit may also power the motor with the transformed energy. Advantageously, the control unit directly powers the electric motor with electric energy, as the energiser unit transforms the signal energy into the electric energy. This embodiment is particularly simple and does not require any recurrent invasive measures for exchanging empty power supplies, such as batteries, that is required in the first embodiment described above. The motor may also be directly powered with wirelessly transmitted electromagnetic or magnetic energy in the form of signals, as the energy is transmitted. All the various functions of the motor and associated components described in the present specification may be used where applicable.

For adjustment devices of the type that requires more, but still relatively low, power for its operation, the energiser unit may comprise a rechargeable electric power supply for storing the electric energy obtained and the control unit may power the electric motor with energy from the rechargeable electric power supply in response to a control signal received from the signal transmitter. In this case, the rechargeable power supply can be charged over a relatively long time (e.g. a few seconds up to a half hour) without powering the electric motor.

The electric power supply suitably comprises an inexpensive simple capacitor. In this case, the electric motor may be a stepping motor. In all embodiments the motor may preferably be able to perform a reversing function.

The signal transmitter may transmit an electromagnetic signal and the energiser unit may draw radiant energy from the electromagnetic wave signal, as the latter is transmitted to the signal receiver, and transform the radiant energy into electric energy.

Alternatively, the energiser unit may comprise a battery or an accumulator, an electrically operable switch adapted to connect the battery to the signal receiver in an on mode when the switch is powered and to keep the battery disconnected from the signal receiver in a standby mode when the switch is unpowered, and a rechargeable electric power supply for powering the switch. The control unit may power the electric motor with energy from the battery in response to a control signal received from the signal transmitter, when the switch is in its on mode. Advantageously, the energiser unit may transform wave energy from the control signal, as the latter is transmitted to the signal receiver, into a current for charging the rechargeable electric power supply, which suitably is a capacitor. Energy from the power supply is then used to change the switch from off (standby mode) to on. This embodiment is suited for adjustment devices of the type that require relatively high power for their operation and has the advantage that the electronic circuitry of the signal receiver does not have to be powered by the battery between adjustments. As a result, the life-time of the battery can be significantly prolonged. The switch may be switched with magnetic, manual or electric energy.

As an example, the signal transmitter may transmit an electromagnetic wave signal and the energiser unit may draw radiant energy from the electromagnetic wave signal, as this is transmitted to the signal receiver, and may transform the radiant energy into said current. The energiser unit suitably comprises a coil of the signal receiver for inducing an alternating current as the electromagnetic wave signal is transmitted through the coil and a rectifier for rectifying the alternating current. The rectified current is used for charging the rechargeable power source.

Alternatively, the signal transmitter and receiver may solely be used for a control signal and a further pair of signal transmitter and receiver may be provided for transferring signal energy to implanted components. By such a double system of signal transmitters and receivers the advantage is obtained that the two systems can be designed optimally for their respective purposes, namely to transmit a control signal and to transfer energy from an energy signal. Accordingly, the apparatus may further comprise an external energy transmitter for transmitting wireless energy, wherein the energiser unit comprises a battery and an operable switch for connecting the battery to the signal receiver in an on mode when the switch is powered and for keeping the battery disconnected from the signal receiver in a standby mode when the switch is unpowered, and the external energy transmitter powers the switch. Suitably, the energy transmitter may directly power the switch with the wireless energy to switch into the on mode. As should be realized by a skilled person, in many of the above-described embodiments of the invention the adjustment device may be operated by control means or manual manipulation means implanted under the skin of the patient, such as a pump, an electrical switch or a mechanical movement transferring means. In the manual embodiment it is not necessary to use a motor for operating the adjustment device.

In embodiments including hydraulic transmission means, an injection port connected to the hydraulic means may be provided for enabling, normally single, once-and-for-all, calibration of the amount of fluid in the hydraulic system.

In all embodiments a motor may be operatively connected to the adjustment device. A reversing device may be implanted in the patient for reversing the motor.

The adjustment device may be adapted to hydraulically adjust the restriction device by using hydraulic means which is devoid of hydraulic fluid of the kind having a viscosity that substantially increases when exposed to heat or a magnetic field, i.e. the hydraulic fluid would not become more viscous when exposed to heat or influenced by magnetic forces.

A pressure sensor may be used to directly or indirectly sense the pressure against the restriction device or the colon or rectum to avoid occurrence of necrosis of the human tissue. The restriction device may be controlled in response to signals from the pressure sensor. The motor which preferably is used to adjust the restriction device must then be capable of performing a reversible function, that is to say, be capable of reversing the driving direction of the motor.

Preferably the adjustment device is directly energised with wirelessly transmitted energy from outside the patient's body. The implanted energy transforming device transforms wireless energy directly or indirectly into kinetic energy for operation of the restriction device. In accordance with another embodiment it would also be possible to use an implanted accumulator or battery and control this implanted energy source from outside the patient's body to supply energy to the adjustment device or other energy consuming parts of the implanted apparatus.

All the above-described various components, such as the motor, pump and capacitor, may be combined in the different embodiments where applicable. Also the various functions described in connection with the above embodiments of the invention may be used in different applications, where applicable.

The invention also provides a method for treating a patient suffering from anal incontinence or stoma surgery comprising surgically implanting in the body of the patient an adjustable restriction device which directly engages the intestine, anal channel, colon or rectum of the patient like an artificial sphincter around the faecal passageway or stoma therein, normally closed, and when desired, mechanically adjusting the restriction device to temporarily open the faecal passageway or stoma. The restriction device will automatically switch between the two restriction devices comprised by the defined restriction device.

The adjustable restriction device preferably is implanted in the base or prolongation of the patient's rectum. It would also be possible to use two or more restricting devices engaging the intestine, anal channel, colon or rectum.

The invention further provides a method for treating anal incontinence, comprising the steps of placing at least two laparascopical trocars in the body of a patient suffering from anal incontinence, inserting a dissecting tool through the trocars and dissecting an area of the colon or rectum in the abdominal or pelvic or retroperitoneal surroundings, placing at least one adjustable restriction device in the dissected area engaging the rectum or colon, adjusting the restriction device to normally restrict the faecal passageway in the rectum or colon, and adjusting the restriction device to open the faecal passageway when the patient wants to relieve himself or herself. The restriction device will automatically switch between the two restriction devices comprised by the restriction device.

A mechanically adjustable restriction device may be used when practising this method, preferably in a non-manual manner, i.e. without touching subcutaneously implanted components of the apparatus.

The invention further provides a method for treating a stoma patient, comprising the steps of placing at least two laparascopical trocars in the body of a patient suffering from the stoma, inserting a dissecting tool through the trocars and dissecting an area of the intestine providing the stoma in the abdominal surroundings, placing at least one adjustable restriction device in the dissected area engaging the intestine, adjusting the restriction device to normally restrict the stoma passageway in the intestine, and adjusting the restriction device to open the stoma passageway when the patient wants to relieve himself or herself. A mechanically adjustable restriction device may be used when practising this method, preferably in a non-manual manner, i.e. without touching subcutaneously implanted components of the apparatus.

The restriction device will automatically switch between the two restriction devices comprised by the restriction device.

The method may further comprise implanting a source of energy in the patient and providing a control device for controlling the source of energy from outside the patient's body to supply energy to the restriction device.

The present invention may also relates to a urinary incontinence treatment apparatus, comprising an adjustable restriction device adapted to engage the urethra or urine bladder of a patient, who suffers from urinary incontinence, to form a restricted urine passageway in the urethra or urine bladder. An implantable adjustment device is provided for adjusting the restriction device to restrict the urethra or urine bladder to close the urine passageway, or release the urethra or urine bladder to open the urine passageway, when the restriction device is implanted in the patient. An implantable operation device is provided for operating the adjustment device.

Urine incontinence is a widespread problem. Many people are helped through training of the muscles in the pelvic floor but too many have severe problems with urine leakage. Many different solutions to this problem have been tried. There is a prior manually operated sphincter system connected to an elastic reservoir/pump placed in the scrotum or in the region of the labia majora. A disadvantage of this system is that over time hard fibrosis is developed around the reservoir which may cause malfunction of pumping components and it is rather complicated to manually squeeze the elastic reservoir when urinating, especially woman can get their fingers wet. Thus, the created fibrosis will sooner or later become a hard fibrotic layer which may make it difficult to pump the reservoir. Yet a further disadvantage is that the use of hydraulic fluid always entails a risk of fluid leaking from the prosthetis. Furthermore, it is a rather complicated task to manually pump the reservoir when needing to urinate.

A prior hydraulic device which is made for compressing the urethra is disclosed in U.S. Pat. No. 5,520,606. Prosthetic sphincters with an inflatable cuff which surrounds the urethra or encloses it on two sides are disclosed in for example U.S. Pat. Nos. 4,571,749 and 4,222,377. U.S. Pat. No. 4,969,474 discloses a hydraulic method for treating both men and women with urinary incontinence problem in the same way. The apparatus of the U.S. Pat. No. 4,969,474 includes a reservoir containing fluid and an inflatable compression device that will compress urethra without risking tissue loss or necrosis to occur. An artificial hydraulically operated urethral sphincter employing an external magnet to achieve closure of the urethral cuff is disclosed in U.S. Pat. No. 5,562,598. A prior mechanical prosthetic sphincter, disclosed in U.S. Pat. No. 4,619,245 comprises a manually controllable actuating component for implanting at a convenient location in the patients body.

The urinary incontinence treatment apparatus is used as an example product and the treatment usage options referred to herein as well as any other possible application inside the body, will in any applicable way also apply to all these alternatives. In this case we focus on both mechanical and hydraulic restriction devices, however, with main focus on hydraulic solutions as an example for all other treatment fields and embodiments.

In this case with the primary goal to supply different kind of hydraulic devices. A prime object of the present invention is to provide a urinary incontinence treatment apparatus, which does not require manual manipulation of a combined reservoir and pump mechanism placed in the scrotum or in the region of the labia majora of the patient.

Another object of the invention is to provide an urinary incontinence treatment apparatus, which does not require complicated surgery.

Yet another object of the invention is to provide an urinary incontinence treatment apparatus, which may be conveniently controlled by the patient with a remote control.

These objects are obtained by an apparatus of the kind described initially characterised in that the operation device comprises a powered operation device and/or a servo means.

The expression "powered" should be understood as energised with everything without manual force, preferably electric energy. In other words, the adjustment device is operated in a non-manual manner. The expression "non-manual manner" should be understood to mean that the adjustment device is not operated by manually touching subcutaneously implanted components of the apparatus or not manipulated by touching the skin of the patient. Thus, as opposed to prior practice when treating urine incontinence, the adjustment device of the invention is not operated by manual forces, such as by manually compressing a fluid containing balloon implanted in the scrotum or in the region of labia majora. Of course, manual manipulation of a subcutaneous start button or the like for activating the powered operation device is permitted within the scope of the present invention.

Alternatively, or in combination with a powered operation device, the servo means may be used, which enables manual manipulation without need for strong manipulation forces. The servo means may comprise hydraulic means, electric control means, magnetic means, or mechanical means, which may be activated by manual manipulating means. Using a servo system will save the use of force when adjusting the adjustment device, which may be of importance in many applications.

The term "servo means" encompasses the normal definition of a servo mechanism, i.e. an automatic device that controls large amounts of power by means of very small amounts of power, but may alternatively or additionally encompass the definition of a mechanism that transfers a weak force acting on a moving element having a long stroke into a strong force acting on another moving element having a short stroke. The servo means may comprise a motor, preferably an electric motor, which may be reversible.

In accordance with a main embodiment of the invention, the apparatus comprises a reservoir, preferably containing a predetermined amount of hydraulic fluid, also implantable in the patient, wherein the operation device, suitably electrically powered, operates the adjustment device by using the hydraulic fluid of the reservoir.

The adjustment device may comprise an expandable cavity in the restriction device, wherein the urethra or urine bladder is squeezed upon expansion of the cavity and released upon contraction of the cavity. In this embodiment the operation device is adapted to distribute hydraulic fluid from the reservoir to expand the cavity, and from the cavity to the reservoir to contract the cavity.

A fluid distribution tube may readily be connected between the reservoir and the cavity in a manner so that the tube does not interfere with other implanted components of the apparatus.

Preferably, the reservoir defines a chamber for the predetermined amount of fluid and the operation device changes the volume of the chamber. The operation device suitably comprises first and second wall portions of the reservoir and is adapted to provide relative displacement between the first and second wall portions of the reservoir, in order to change the volume of the chamber.

The operation device may be adapted to provide said relative displacement in response to the pressure in the reservoir. Suitably, the operation device comprises a pressure controlled hydraulic operation device. For safety, an alarm may be provided for generating an alarm signal in response to the lapse of a predetermined time period during which the pressure controlling the hydraulic operation device exceeds a predetermined high value.

Suitably, the operation device is adapted to distribute fluid from the reservoir to the cavity of the restriction member in response to a predetermined first displacement of the first wall portion of the reservoir relative to the second wall portion of the reservoir and may distribute fluid from the cavity to the reservoir in response to a predetermined second displacement of the first wall portion relative to the second wall portion.

The first and second wall portions of the reservoir may be displaceable relative to each other by a magnetic, hydraulic, or electric power means, such as an electric motor. In this embodiment no pump is used, only the volume of the reservoir is varied. This is of great advantage compared to the solution described below when the operation device comprises a pump used to pump fluid between the reservoir and the adjustment device because there is no need for a non-return valve and it is still possible to have fluid going both to and from the reservoir. Thus, the significant risk of malfunction when using such a non-return valve implanted in the patient is eliminated.

The operation device may comprise hydraulic means and a fluid conduit extending between the hydraulic means and the adjustment device. The hydraulic means and conduit are devoid of any non-return valve. The reservoir may form part of the conduit and a fluid chamber with a variable volume. The operation device may distribute fluid from the fluid chamber to the adjustment device by reduction of the volume of the chamber and withdraw fluid from the adjustment device by expansion of the volume of the chamber. The operation device preferably comprises a motor for moving a movable wall of the reservoir for changing the volume of the chamber. Any kind of motor could be used for the different operations as well as wireless remote solutions for controlling the operations.

The restriction device preferably is operable to perform a reversible function and accordingly there is a reversing device implantable in the patient for reversing the function performed by the restriction device. Such a reversing function preferably involves enlarging and restricting the urine passageway by the restriction device, suitably in a stepless manner. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a gearbox.

Where the reversing device comprises a switch the control device suitably controls the operation of the switch by shifting polarity of released energy supplied to the switch. The switch may comprise an electric switch and the source of energy may supply electric energy for the operation of the switch. The switch mentioned above may comprise an electronic switch or, where applicable, a mechanical switch.

Where the operation device comprises a motor, the reversing device is adapted to reverse the motor.

In accordance with another particular embodiment of the invention, the operation device comprises a pump for pumping fluid between the reservoir and the adjustment device. A mechanical solution is proposed in which it is possible to pump fluid from the reservoir to the adjustment device and vice versa just by pushing an activation member in one direction. The pump preferably comprises a first activation member for activating the pump to pump fluid from the reservoir to the adjustment device, and a second activation member for activating the pump to pump fluid from the adjustment device to the reservoir. At least one of the first and second activation members may be operable by manual manipulation, preferably to permit manual pushing, pulling or rotation thereof in one direction, or by a device powered magnetically, hydraulically, or electrically (e.g. by an electric motor), or be operable by a combination of these methods. Suitably, at least one of the activation members may be adapted to operate when subjected to an external pressure exceeding a predetermined magnitude.

Another alternative is a pump pumping in only one direction and an adjustable valve to change the direction of fluid to either increase or decrease the amount of fluid in the reservoir. This valve may be manipulated either manually, mechanically, magnetically, or hydraulically.

The main embodiment of the invention described above including the reservoir may alternatively be equipped with a servo means comprising a reverse servo. The term "reverse servo" is to be understood as a mechanism that transfers a strong force acting on a moving element having a short stroke into a weak force acting on another moving element having a long stroke; i.e. the reverse function of the above-defined alternative mechanism of a normal servo mechanism. A first closed hydraulic system that controls another closed hydraulic system in which hydraulic means of the adjustment device is incorporated may be used. Minor changes in the amount of fluid in a smaller reservoir of the first system could then be transferred by the reverse servo into major changes in the amount of fluid in a larger reservoir in the second system. In consequence, the change of volume in the larger reservoir of the second system affects the hydraulic means of the adjustment device. For example, a short stroke that decreases the volume of the smaller reservoir will cause the larger reservoir to supply the adjustment device with a large amount of hydraulic fluid, which in turn results in a long mechanical adjustment stroke on the restriction device.

The great advantage of using such a reverse servo is that the larger volume system could be placed inside the abdomen or retroperitoneum where there is more space and still it would be possible to use manual manipulation means of the smaller system subcutaneously. The smaller reservoir could be controlled directly or indirectly by a fluid supply means. The fluid supply means may include another small reservoir, which may be placed subcutaneously and may be activated by manual manipulation means. Both the normal servo means and the specific reverse servo may be used in connection with all of the various components and solutions described in the present specification.

Thus, the reverse servo may be adapted to provide relative displacement between the first and second wall portions of the reservoir, suitably in response to the pressure in the reservoir, in order to change the volume of the chamber of the reservoir.

Generally, the servo means, including the reverse servo, comprises a pressure controlled servo means. The alarm mentioned above may alternatively be adapted to generate an alarm signal in response to the lapse of a predetermined time period during which the pressure controlling the servo means exceeds a predetermined high value.

The reverse servo may comprise magnetic means, electric means or manual manipulation means or a combination thereof. Preferably, however, the reverse servo comprises hydraulic means.

In accordance with a particular embodiment of the invention, the reverse servo further comprises a servo reservoir defining a chamber containing servo fluid, and the operation device comprise first and second wall portions of the servo reservoir, which are displaceable relative to each other to change the volume of the chamber of the servo reservoir. The first and second wall portions of the servo reservoir may be displaceable relative to each other by magnetic means, hydraulic means, or electric control means.

Where the reverse servo comprises hydraulic means it may further comprise a fluid supply reservoir connected to the servo reservoir in a closed system and containing a further predetermined amount of fluid. The fluid supply reservoir defines a chamber for the further predetermined amount of fluid and the operation device is adapted to change the volume of the chamber and thereby control the amount of fluid in the servo reservoir. The fluid supply reservoir comprises first and second wall portions, which are displaceable relative to each other to change the volume of the chamber of the fluid supply reservoir. Suitably, the fluid supply reservoir increases the amount of fluid in the servo reservoir in response to a predetermined first displacement of the first wall portion of the fluid supply reservoir relative to the second wall portion of the fluid supply reservoir and decreases the amount of fluid in the servo reservoir in response to a predetermined second displacement of the first wall portion of the fluid supply reservoir relative to the second wall portion of the fluid supply reservoir.

In accordance with an embodiment of the invention, the adjustment device comprises a hydraulic adjustment device, and an implantable reservoir containing a predetermined amount of hydraulic fluid and a conduit providing fluid connection between the reservoir and the hydraulic adjustment device are provided. The operation device is adapted to operate the hydraulic adjustment device by distributing hydraulic fluid through the conduit between the reservoir and the hydraulic adjustment device, wherein the conduit and hydraulic adjustment device are devoid of any non-return valve to permit free flow of hydraulic fluid in both directions in the conduit. Preferably, the reservoir forms a fluid chamber with a variable volume, and the operation device is adapted to distribute fluid from the chamber to the adjustment device by reduction of the volume of the chamber and to withdraw fluid from the adjustment device by expansion of the volume of the chamber. The operation device may comprise a motor or a pump. Alternatively, the operation device may comprise a movable wall of the reservoir for changing the volume of the chamber. For example, the operation device may be adapted to change the volume of the chamber by moving the movable wall in response to the pressure in the chamber.

In the above embodiments including a reservoir for hydraulic fluid an injection port may be provided for subcutaneous implantation in the patient to be in fluid communication with the chamber of the reservoir. The injection port may be integrated in the reservoir. Such an injection port may be provided for enabling, normally single, once-and-for-all, calibration of the amount of fluid in the hydraulic system used.

In the various embodiments hereinafter described the restriction device generally forms an at least substantially closed loop. However, the restriction device may take a variety of different shapes, such as the shape of a square, rectangle or ellipse. The substantially closed loop could for example be totally flat, i.e. thin as seen in the radial direction. The shape of restriction device may also be changed during use, by rotation or movements of the restriction device in any direction. A physical lumen, like the urethra or urine bladder, often is easier to restrict by contracting two opposite sidewalls of the lumen against each other. Thus, the restriction device may be designed to perform such a contracting effect of the opposite walls of the urethra or urine bladder. Either mechanical or hydraulic solutions may be employed to operate the restriction device. Alternatively, the restriction device may comprise an adjustable cuff, a clamp or a roller for bending or rotating the urethra or urine bladder to close its passageway. Such a cuff, clamp or roller may also be utilized for squeezing the urethra or urine bladder against human material inside the body of the patient, for example the sacral bone of the patient, or against implanted structures of the apparatus. The bending or rotating members may take any shape and be either hydraulic or non-inflatable.

Preferably the restriction device comprises an elongated restriction member and forming means for forming the restriction member into at least a substantially closed loop around the urethra or urine bladder, wherein the loop defines a restriction opening, whereby the adjustment device adjusts the restriction member in the loop to change the size of the restriction opening.

Advantageously, the forming means may form the restriction member into a loop having a predetermined size. Alternatively, the forming means may form the restriction member into a loop having a size selected from several predetermined sizes.

The adjustment device may change the size of the restriction opening such that the outer circumferential confinement surface of the restriction member either is changed or is unchanged.

The elongated restriction member may be flexible, for example take the shape of a belt or cord, and the adjustment device may pull a first portion of the flexible restriction member from a second portion of the flexible restriction member opposite the first portion in the loop to squeeze the urethra or urine bladder between the opposite lengths of the elongated flexible restriction member to restrict the urine passageway. The restriction member may be non-inflatable, and the adjustment device may mechanically adjust the restriction member in the loop.

The adjustment device may mechanically or hydraulically adjust the restriction device. In the embodiments described the adjustment device may either mechanically or hydraulically adjust the restriction device, where applicable. It should be noted that the operation device might mechanically or hydraulically operate the adjustment device irrespectively of whether the adjustment device is adapted to adjust the restriction device mechanically or hydraulically.

In accordance with an embodiment of the invention, the restriction device comprises at least two elements on opposite or different sides of the urethra or urine bladder, and the adjustment device decreases the distance between the elements to squeeze the urethra or urine bladder between the elements, thereby restricting the urine passageway. It is also possible to use only one element and squeeze the urethra or urine bladder against human bone or tissue. The elements above may as well as all the restriction members mentioned in this application be everything from rigid to soft.

In accordance with an alternative, the restriction device bends or rotates a portion of the urethra or urine bladder to restrict the urine passageway in the same. For example, the restriction device may comprise at least two bending members, such as cylindrical or hour-glass shaped rollers, positioned on opposite or different sides of the urethra or urine bladder and displaced relative to each other along the urethra or urine bladder, and the adjustment device may move the bending members against the urethra or urine bladder to bend the latter to restrict the urine passageway. The restriction device may also rotate a portion of the urethra or urine bladder. The bending or rotating members may take any shape and be either hydraulic or non-inflatable.

Alternatively, the two bending members one placed more distal than the other may be rotated in opposite directions relative to each other. With interconnecting means for example flexible bands between the bending members a restriction will occur between the bending members when they are rotated.

Preferably the adjustment device is operable to adjust the restriction device to steplessly change the restriction of the urine passageway in the urethra or urine bladder.

All embodiments according to the invention may be controlled by a wireless remote control.

In accordance with an advantageous embodiment of the invention, there is provided a wireless remote control for non-invasively controlling the operation device. The remote control may conveniently comprise an external hand-held remote control unit, which is manually operable by the patient to control the restriction device to squeeze and release the urethra or urine bladder. With the wireless remote control the apparatus of the invention is conveniently controlled by the patient when he so desires, which is of great advantage compared to the prior art procedures. With the remote control the apparatus of the invention is conveniently controlled to adjust the implanted restriction device to release the urine passageway when the patient wants to relieve himself or herself.

The remote control may advantageously be capable of obtaining information related to important parameters, such as the condition of the urine passageway or the pressure against the restriction device, and of commanding the operation device to operate the adjustment device to adjust the restriction device in response to obtained information. With the remote control the apparatus of the invention is conveniently controlled to adjust the implanted restriction device to open and close the urine passageway. The adjustment device may control the restriction device to steplessly change the restriction of the passageway.

Preferably, the wireless remote control comprises a separate signal transmitter or receiver and a signal receiver or transmitter implanted in the patient. For example, the signal transmitter and signal receiver may transmit and receive a signal in the form of digital pulses, which may comprise a magnetic or electric field. Alternatively, which is preferred, the signal transmitter and signal receiver may transmit and receive an electromagnetic wave signal, a sound wave signal or a carrier wave signal for a remote control signal. The receiver may comprise an implanted control unit for controlling the adjustment device in response to a control signal from the signal transmitter. Any known or conventional signal transmitting or signal receiving means that is suitable for use with a human or mammal patient may be provided as the signal transmitter or signal receiver.

The apparatus of the invention may further comprise an implanted energiser unit for providing energy to energy consuming implanted components of the apparatus, such as electronic circuits and/or a motor for operating the adjustment device. Where a motor is provided the control unit is adapted to power the motor with energy provided by the energiser unit in response to a control signal received from the signal transmitter. The motor may be any type of motor, such as a pneumatic, hydraulic or electric motor and the energiser unit may power the motor with pressurized gas or liquid, or electric energy, depending on the type of motor. Where the motor is an electric motor, it may power pneumatic or hydraulic equipment.

The remote control advantageously comprises wireless energy transfer device for transferring energy from outside the patient's body to energy consuming implantable components of the apparatus. The energy transfer device may comprise said energiser unit is adapted to transform energy from the control signal, as it is transmitted to the signal receiver, into electric energy. Where the operation device comprises a motor the wireless energy transfer device is adapted to directly power the motor with transferred energy.

The energy transferred by the wireless energy transfer device preferably comprises a signal, suitably a wave signal. The energy transferred by the wireless energy transfer device may comprise an electric field or a magnetic field or a combination thereof. The signal may be analog or digital or a combination thereof. The energy transfer device may transfer the energy from the signal into a direct, pulsating direct or alternating current or a combination thereof.

Any of the above mentioned signals may comprise analog or digital pulses. The analog or digital signal may comprise a magnetic field or an electric field or a combination thereof. Where the signal is a wave signal it may comprise an electromagnetic wave signal, a sound wave signal or a carrier wave signal for a remote control signal or a combination thereof. Where a carrier signal is used it may be frequency, amplitude or frequency and amplitude modulated.

The apparatus of the invention may comprise an implantable source of energy for powering the operation device and/or for energizing other energy consuming components of the apparatus, wherein the energy from the source of energy is releasable from outside the patient's body. Furthermore, the apparatus may comprise an energy transmission device for wireless transmission of energy of a first form and an energy transforming device implantable in the patient for transforming the energy of the first form into energy of a second form, to be supplied to the source of energy and/or other implantable energy consuming parts of the apparatus. The energy transforming device may transform the wireless energy directly or indirectly into energy different than the wireless energy for operation of the restriction device. Typically, the energy of the second form is different than the energy of the first form. The function of the energy transmission device may be different from that of the energy transforming device.

An implantable motor or pump for operating the adjustment device may be provided, wherein the energy transmission device may be adapted to transmit wireless energy in the form of a magnetic field or electromagnetic waves or field for direct power of the motor or pump, as the wireless energy is being transmitted. Suitably, the energy transmission device transmits energy by at least one signal separate from the above mentioned control signal.

An implantable stabiliser for stabilising the energy of the first or second form may be provided. Where the energy of the second form comprises electric current, the stabiliser suitably comprises at least one capacitor.

Generally, the source of energy comprises a battery, accumulator, capacitor or a combination thereof.

In accordance with an embodiment of the invention, the apparatus comprises a control device adapted to produce wireless energy for directly powering the operation device and/or for energizing other energy consuming components of the apparatus.

It should be understood that the energy consuming parts of the apparatus for example a motor or pump may be or may not be energised with the unchanged wirelessly transmitted energy as this being transmitted as well as being or not being energised with energy different than the transmitted energy for example transformed into electrical energy but still directly used for energising the energy consuming parts of the apparatus as the transmitted energy is transmitted. Alternatively the energy consuming parts of the apparatus may be energised from a implanted source of energy or storage device, which still may be loaded with wireless energy. In all these aspects it is preferable to be able to wirelessly control the release of energy and get an feedback of the result of the performed function of the device. Direct use of transmitted energy may be unreliable without a feedback what has happened, has the energy reached it's goal?

Generally, the wireless energy may comprise a wave signal including a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Any of the above mentioned signals may comprise a wave signal including a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

The control device may be adapted to produce wireless energy in the form of a train of energy pulses and the energy transfer device may be adapted to intermittently transfer the train of energy pulses for direct use in connection with the energising of the energy consuming components of the apparatus. Alternatively, the control device may be adapted to control the energy transforming device to produce the energy of the second form in said train of energy pulses for direct use in connection with the operation of the adjustment device. The transferred energy preferably comprises electric energy. An implantable capacitor may be provided for producing the train of energy pulses.

Where a capacitor is used in any of the above described embodiments it may have a relatively low capacity, i.e. less than 0.1 µf, in order to be small and suited for implantation.

Where the operation device comprises an implantable motor or pump for operating the adjustment device, the energy transfer device may be adapted to directly power the motor or pump with transferred energy, at the same time as the energy is transferred. Where a pump is used it should not be a plunger type of pump, because a plunger pump is noisy, but may comprise a peristaltic or membrane pump.

As mentioned above the apparatus comprises a wireless remote control for non-invasively controlling the operation device, which preferably is electrically powered. Alternatively, the operation device is powered by magnetic energy, non-magnetic energy, electromagnetic energy, non-electromagnetic energy, kinetic energy, non-kinetic energy, sonic energy, non-sonic energy, thermal energy or non-thermal energy. However, the operation device may be unpowerable by permanent static magnetic energy. Any other kind of energy, such as electric, electromagnetic energy or a moving permanent magnetic energy, may be conceivable for operating the adjustment device. As a result, the implanted restriction device would not be accidentally adjusted if the patient comes close to any permanent magnet. Suitably, the operation device is adapted to non-invasively operate the adjustment device.

Where the operation device comprises a hydraulic operation device it may use hydraulic fluid, the viscosity of which changes when the hydraulic fluid is exposed to energy, preferably electric energy, different than thermal energy. However, use of hydraulic fluid of the kind having a viscosity that increases when exposed to heat or a magnetic field, i.e. the hydraulic fluid would not become substantially more viscous when exposed to heat or influenced by magnetic forces, should be avoided, because external heat sources or heat from the body when the patient has fever and external magnetic sources might affect the implanted components of the apparatus.

The adjustment device is may be operable to adjust the restriction device to steplessly change the restriction of the urine passageway. Furthermore, the adjustment device may be adapted to mechanically adjust the restriction device. Alternatively, it may be adapted to hydraulically adjust the restriction device by using hydraulic means, which is devoid of hydraulic fluid of the kind having a viscosity that substantially increases when exposed to heat or a magnetic field.

In accordance with an embodiment of the invention, the apparatus comprises a control device for controlling the restriction device. The control device may comprise an internal programmable control unit implantable in the patient and, possibly an external control unit outside the patient's body for programming the programmable internal control unit. Alternatively, the external control unit may be programmable and wirelessly control the restriction device. The control device may be adapted to produce wireless energy for directly powering the operation device and/or for energizing other energy consuming components of the apparatus.

At least one sensor for sensing at least one physical parameter of the patient may conveniently be implanted in the patient. The sensor may preferably sense as the physical parameter the horizontal position of the patient or may comprise a pressure sensor for sensing the pressure against the restriction device or the urethra or urine bladder or other important parameters. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor.

Either the internal control unit or the external control unit of the control device may suitably control the restriction device to enlarge or close the urine passageway. For safety the restriction device may enlarge or open the urine passageway in response to the sensor sensing for example an abnormally high pressure value. The internal control unit may directly control the restriction device in response to signals from the sensor.

Wherever magnetic means is utilized according to the invention it may comprise a permanent magnet and a magnetic material reed switch, or other suitable known or conventional magnetic means.

Where a source of energy is used the control device suitably is operable from outside the patient's body for controlling the source of energy to release energy for use in connection with the operation of the adjustment device, when the adjustment device is implanted. The source of energy may be provided external to the patient's body, and the control device may be adapted to control the external source of energy to release wireless energy for use in connection with the operation of the adjustment device.

The control device may control the source of energy to release magnetic energy, non-magnetic energy, electromagnetic energy, non-electromagnetic energy, kinetic energy, non-kinetic energy, sonic energy, non-sonic energy, thermal energy or non-thermal energy, preferably in a non-invasive manner and for a determined time period and/or in a determined number of energy pulses.

Where the implantable components of the apparatus comprise electrical components they may include at least one or a single voltage level guard. In this case, the electrical components suitably are devoid of any current detector and/or charge level detector. Furthermore, the electrical components may comprise a capacitor or accumulator, wherein the charge and discharge of the capacitor or accumulator is controlled by use of the voltage level guard. As a result, there is no need for any implanted current detector and/or charge level detector for the control of the capacitor, which makes the apparatus simple and reliable.

In accordance with an advantageous embodiment of the invention, the apparatus comprises an implantable switch for directly or indirectly switching the operation of the restriction device. The switch may be operated by the energy supplied by the energy transmission device mentioned above to switch from an off mode, in which the implantable source of energy mentioned above is not in use, to an on mode, in which the source of energy supplies energy for the operation of the restriction device.

In accordance with an alternative embodiment, the above mentioned a remote control may be employed for controlling the implantable source of energy, wherein the switch is operated by the energy supplied by the energy transmission device to switch from an off mode, in which the remote control is prevented from controlling the source of energy and the source of energy is not in use, to a standby mode, in which the remote control is permitted to control the source of energy to supply energy for the operation of the restriction device.

In accordance with another alternative embodiment, the switch is operated by the energy supplied by the implantable energy transforming device mentioned above to switch from an off mode, in which the source of energy is not in use, to an on mode, in which the source of energy supplies energy for the operation of the restriction device.

In accordance with yet another alternative embodiment, the switch is operated by the energy supplied by the energy transforming device to switch from an off mode, in which the remote control is prevented from controlling the source of energy and the source of energy is not in use, to a standby mode, in which the remote control is permitted to control the source of energy to supply energy for the operation of the restriction device.

Suitably, the restriction device is embedded in a soft or gel-like material, such as a silicone material having hardness less than 20 Shore.

The energy transforming device may be designed to be implanted subcutaneously or in the abdomen, thorax or cephalic region of the patient.

The adjustment device may be adapted to adjust the restriction device such that the restriction device provides a predetermined contraction of the urine passageway that is satisfactory for the patient.

The adjustment device is preferably adapted to adjust the prosthesis device in a non-flux magnetic or non-thermal manner or non-viscosity changing manner, because these would give rise to unreliable function of the device. The expression "non-viscosity changing manner" should be understood to mean that the adjustment device is not adjusted by changing the viscosity of the hydraulic fluid used.

All the above described various components, such as the motor, pump and capacitor, may be combined in the different embodiments where applicable. Also the various functions described in connection with the above embodiments of the invention may be used in different applications, where applicable. Specifically, the various remote control functions described and all the various methods for supplying energy may be used in any conceivable combination that is apparent to those skilled in the art.

The invention also provides a method for treating a patient suffering from urinary incontinence, comprising the steps of placing at least two laparascopical trocars in the body of a patient suffering from urinary incontinence, inserting a dissecting tool through the trocars and dissecting an area of the urethra or urine bladder in the abdominal or pelvic or retroperitoneal surroundings, placing at least one adjustable restriction device in the dissected area engaging the urethra or urine bladder adjusting the restriction device to normally restrict the urine passageway in the urethra or urine bladder, and adjusting the restriction device to open the urine passageway when the patient wants to relieve himself or herself. A hydraulic adjustable restriction device may be used when practicing this method, preferably in a non-manual manner, i.e. without touching subcutaneously implanted components of the apparatus.

The method may further comprise implanting a source of energy in the patient and providing a control device for controlling the source of energy from outside the patient's body to supply energy for the adjustment of the restriction device.

The present invention also provides a method for treating urinary incontinence, comprising surgically implanting in the body of a patient suffering from urinary incontinence an adjustable restriction device engaging the urethra or urine bladder to restrict the urine passageway, and when desired to allow the patient to urinate, adjusting the restriction device to temporarily release the urethra or urine bladder to open the urine passageway. The method may further comprise implanting an elongated restriction member of the restriction device around the urethra or urine bladder.

The urinary incontinence treatment apparatus of the invention may also be laparoscopicly implanted. Thus, there is provided a method comprising the steps of placing at least two laparoscopical trocars in the patient's body, inserting a dissecting tool through the trocars and dissecting an area of the pelvic or abdominal or retroperitoneal surroundings and placing an operable restriction device in the dissected area, so that the restriction device engages the urethra or urine bladder to restrict the urine passageway.

There are a number of conceivable alternative embodiments of the invention that give the same result as the above-described embodiments. For example, the microprocessor of the external and implanted, respectively, control units may be replaced by discrete components. The power amplifier of the external control unit may be omitted if the signals generated by the signal generator are strong enough. Therefore, the invention is to be accorded the broadest interpretation of the appended claims to encompass all equivalent structures and assemblies.

Any embodiment, part of embodiment, method, or part of method may be combined in any applicable way. Any embodiment described for urinary incontinence or any embodiment described for anal incontinence may apply to all other treatment fields treatment apparatus or methods presented herein or any applicable apparatus usage placed inside the body including the described restriction device using two automatically switching restriction devices.

BRIEF DESCRIPTION OF THE DRAWINGS

The invention is now described, by way of example, with reference to the accompanying drawing, in which:

FIG. 1 is an overview of a patient when the implantable hydraulic restriction device has been implanted, FIG. 2a shows a sectional view of the implanted hydraulic restriction device when fixated to a muscular layer of the abdominal wall, FIG. 2b shows an embodiment of the implantable hydraulic restriction device, FIG. 3 shows an embodiment of the implantable hydraulic restriction device, FIG. 4 is an overview of a patient when the implantable hydraulic restriction device has been implanted for restricting the fallopian tubes of the patient, FIG. 5a shows an embodiment of the implantable hydraulic restriction device restricting the fallopian tube of the patient, FIG. 5b shows the uterus and fallopian tubes of the patient when the implantable hydraulic restriction device has been implanted, FIG. 12 shows an overview of a patient when the implantable hydraulic restriction device has been implanted for restricting the large intestine of the patient, FIG. 13a shows the large intestine of the patient schematically, when the hydraulic restriction device has been implanted, FIG. 13b shows a sectional view of the patient when the implantable hydraulic restriction device has been implanted for restricting the large intestine, FIG. 22 shows a sectional side-view and sectional top-view of an embodiment of a control unit for use in the implantable hydraulic restriction device, FIG. 23 shows a sectional side-view and sectional top-view of an embodiment of a control unit for use in the implantable hydraulic restriction device, FIG. 24 shows a sectional side-view and sectional top-view of an embodiment of a control unit for use in the implantable hydraulic restriction device, FIG. 25 shows a sectional side-view and sectional top-view of an embodiment of a control unit for use in the implantable hydraulic restriction device, FIG. 29 shows an elevated perspective view of an operation device for operating an implantable hydraulic restriction device, FIG. 30a shows a sectional side view of an operation device for operating an implantable hydraulic restriction device, in a first state, FIG. 30b shows a sectional side view of the operation device of FIG. 30a, in a second state, FIGS. 31a and 31b shows a sectional side-view and sectional top-view of an operation device for operating an implantable hydraulic restriction device.

DETAILED DESCRIPTION

Figure 6:
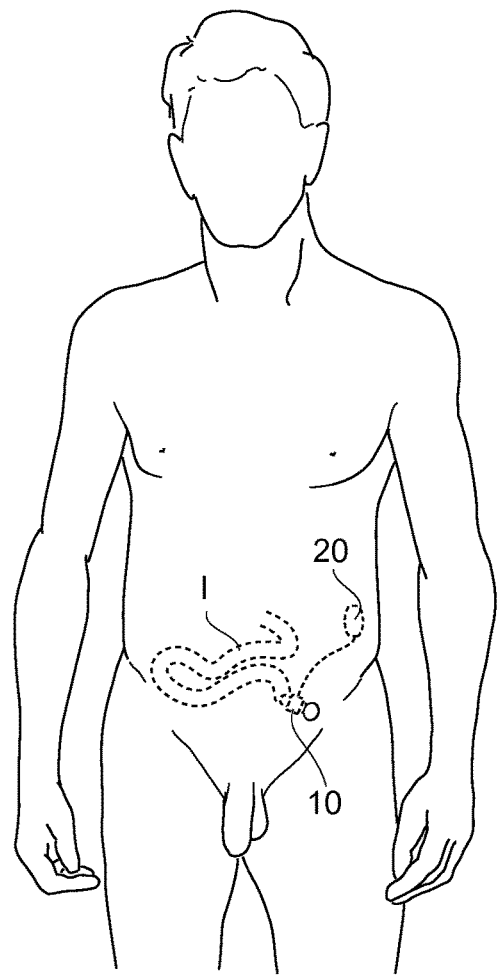
FIG. 6 is an overview of a patient when the implantable hydraulic restriction device has been implanted for restricting a part of a stoma of the patient.

A hydraulic implantable restriction device for restricting a luminary organ of a patient is provided. The hydraulic implantable restriction device comprises a first hydraulic restriction element adapted to restrict a first portion of the luminary organ, and a second hydraulic restriction element adapted to restrict a second portion of the luminary organ. The luminary organ could for example be an intestine of the patient, a blood vessel of the patient, the urethra of the patient, the vas deference of the patient, the stomach of the patient, the esophagus of the patient or the oviducts of the patient, and the restriction thereof is adapted to control the flow of matter in the luminary organ. When a portion of a luminary organ is restricted, the blood flow of that particular portion of the organ is hampered, which creates a risk that the portion suffers from ischemia which may cause irreversible necrosis of the restricted tissue. By constantly switching the restricted portion the risk of necrosis or other damage to the tissue of the patient is considerably reduced. For this purpose, the hydraulic implantable restriction device further comprises a control unit adapted to control the first and second restriction elements for automatically switching between restricting the first and second portion of the luminary organ, for creating a less invasive restriction. By switching between a first and second portion of restriction, the blood flow hampering effect of the restriction can be limited in time, such that the risk of damage to the restricted tissue is reduced. The control unit is adapted to automatically switch between restricting the first and second portion of the luminary organ on the basis of at least one of: a lapsed time being between 10 minutes and 6 months, the patient using the function of the restricted luminary organ, and the receipt of a control signal. The patient using the function could for example be, in an embodiment were the restriction device is adapted to restrict the urethra, the patient releasing the restriction for the purpose of releasing urine. The control unit could be operated on the basis of the receipt of a control signal, which for example could be control signal generated on the basis of a sensor input generated on the inside of the body of the patient, or a control signal transmitted from outside of the body of the patient.

The lapsed time should be adapted to the need for the tissue of the particular position to recover from the strain created by the restriction, which could depend on the application area. Too frequent switching consumes a lot of energy, which is an aspect which must be considered when choosing the intervals of the operation. The lapsed time could for example be 1 hour, 2 hours, 4 hours, 8 hours, 12 hours, 16 hours, 20 hours or a full 24 hours. In other applications the lapsed time could be as much as 2 days, 4 days, 1 week, 2 weeks, 1 month, 2 months or 6 months, in which case the energy consumption is very low.

The implantable hydraulic restriction device could comprise an implantable fluid reservoir connected to the first and second restriction element by means of fluid conduits. Fluid could be transported from the fluid reservoir to the first and second restriction element by means of the reservoir comprising at least one moveable wall portion for changing the volume of the implantable fluid reservoir and thereby moving fluid from the implantable fluid reservoir to the first and second restriction elements.

The implantable hydraulic restriction device may further comprise a hydraulic pump for pumping fluid from the implantable reservoir to at least one of the first and second restriction element. The hydraulic pump may be a hydraulic pump in the form of a reservoir acting as a pump by a wall of the reservoir moving, or by the reservoir acting as a pump to move fluid by changing volume, or at least one non-valve pump, or at least one valve pump, or at least one peristaltic pump, or at least one membrane pump, or at least one gear pump, or at least one bellows pump.

In another embodiment, the implantable hydraulic restriction device may further comprise an implantable valve member for directing fluid from the implantable reservoir to the first or second restriction element, in which case the hydraulic restriction device may only need one hydraulic pump capable of moving fluid in one direction.

For the purpose of operating the restriction devices, the implantable hydraulic restriction device may further comprise at least one motor for operating a movable wall portion, an implantable pump, and an implantable valve member. The motor could be an electrical motor selected from for example an alternating current (AC) electrical motor, a direct current (DC) electrical motor, a linear electrical motor, an axial electrical motor, a piezo-electric motor, a three-phase motor, a more than one-phase motor, a bimetal motor, and a memory metal motor.

For the purpose of increasing the force and reducing the speed of the work created by the motor, the implantable hydraulic restriction device may further comprise a gear system placed between the motor and a movable wall portion, or the implantable pump or the implantable valve member.

The gear system could be a gear system comprising an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element may be adapted to engage the inside of the first gear, such that the outside of the first gear is pressed against the inside of the second gear such that the teeth of the first gear are interengaged with the teeth of the second gear in at least one position interspaced by positions at which the teeth are not interengaged. The operation of the operable element advances the positions and thereby causes relative rotation between the first gear and the second gear.

The operable element may comprise a planetary gear or a structure or wheel using friction to interconnect with the first gear.

The implantable hydraulic restriction device may further comprise a threaded member arranged to move a wall portion of an implantable reservoir. The threaded member may be connected to a motor or a gear system for transferring a rotating force to a reciprocating force for moving the wall portion.

The implantable hydraulic restriction device may further comprise an injection port for supplying fluid to the reservoir, which could be a subcutaneous injection port comprising a self sealing silicone membrane adapted to be penetrated by an injection needle.

The implantable hydraulic restriction device may further comprise a servo connected between the motor and one of a movable wall portion, an implantable pump, and an implantable valve member.

The hydraulic pump comprised in the implantable hydraulic restriction device may be a peristaltic hydraulic pump comprising: a hollow member for fluid transportation and an operable compression member adapted to engage and compress the hollow member. The compression member is in direct or indirect connection with a motor such that the motor operates the compression member such that fluid is transported in the hollow member. The hollow member of the peristaltic pump may form a loop or part of a loop adapted to at least partially encircle at least one of the gear system and the motor in at least partially the same axial plane, and the motor may be adapted to propel the compressing member such that the compression member compresses the hollow member towards the outer periphery of the loop or part of loop.

The implantable hydraulic restriction device may further comprise an implantable energizing unit for providing energy to energy consuming components of the device to be implanted in the patient and/or an energy transfer member for wireless transfer of energy from outside the patient's body to an energy consuming implantable component of the device, or to the implantable energizing unit.

A luminary organ is to be understood as any organ comprising a lumen, a hollow space or a space adapted to be filled with, or pass, a fluid. Examples of luminary organs A luminary organ could for example be an intestine of the patient, a blood vessel of the patient, the urethra of the patient, the vas deference of the patient, the stomach of the patient, the esophagus of the patient, the bile duct of the patient, a part of the intestine of the patient forming an ostomy, or the oviducts of the patient.

Restriction of a luminary organ is to be understood as any operation decreasing a cross-sectional area of the lumen of the organ. The restriction may decrease the flow of matter in the lumen, or may completely close the lumen such that no matter can pass.

A control unit is to be understood as any implantable unit capable of controlling the restriction device. A control unit could include a motor and/or pump or another operation device for operating the implantable hydraulic restriction device, or could be separate from the operation device and only be adapted to control the operation thereof.

A control signal is to be understood as any signal capable of carrying information and/or electric power such that the restriction device can be directly or indirectly controlled.

A gear system is to be understood as any system capable of providing transmission such that work of a first form can be transmission into work of a second form. The form of the work could for example include the velocity, the force and/or the direction of the work.

In the following a detailed description of embodiments of the invention will be given with reference to the accompanying drawings. It will be appreciated that the drawings are for illustration only and are not in any way restricting the scope of the invention. Thus, any references to directions, such as "up" or "down", are only referring to the directions shown in the figures. It should be noted that the features having the same reference numerals have the same function, a feature in one embodiment could thus be exchanged for a feature from another embodiment having the same reference numeral unless clearly contradictory. The descriptions of the features having the same reference numerals should thus be seen as complementing each other in describing the fundamental idea of the feature and thereby showing the features versatility.

FIG. 1 is an overview of a patient in which hydraulic implantable restriction device for restricting a luminary organ has been implanted. The hydraulic implantable restriction device comprises restriction elements 10, and a control unit 20 connected to the restriction elements 10 for controlling the operation thereof. The control unit 20 is connected to the restriction elements by means of a fluid conduit transferring hydraulic force and/or an electrical lead transferring a control signal.

FIG. 2a shows an embodiment of a hydraulic implantable restriction device for restricting a luminary organ L of a patient. The hydraulic implantable restriction device comprises a first hydraulic restriction element 10' adapted to restrict a first portion p1 of the luminary organ L, and a second hydraulic restriction element 10" adapted to restrict a second portion p2 of the luminary organ L. The luminary organ L could for example be an intestine of the patient, a blood vessel of the patient, the urethra of the patient, the vas deference of the patient, the stomach of the patient, a portion of the esophagus of the patient or the oviducts of the patient, and the restriction thereof is adapted to control the flow of matter in the luminary organ L. The hydraulic implantable restriction device further comprises a control unit 20 comprising an operation device 110 adapted to control the first and second restriction elements 10', 10" for automatically switching between restricting the first and second portion p1, p2 of the luminary organ L, for creating a less invasive restriction. By switching between a first and second portion p1, p2 of restriction, the blood flow hampering effect of the restriction can be limited in time, such that the risk of damage to the restricted tissue is reduced. The control unit 20 is adapted to automatically switch between restricting the first and second portion p1, p2 of the luminary organ L on the basis of at least one of: a lapsed time being between 10 minutes and 6 months, the patient using the function of the restricted luminary organ L, and the receipt of a control signal. The patient using the function could for example be, in an embodiment were the restriction device is adapted to restrict the urethra, the patient releasing the restriction for the purpose of releasing urine. The control unit 20 could be operated on the basis of the receipt of a control signal, which for example could be a control signal generated on the basis of a sensor input generated on the inside of the body of the patient, or a control signal transmitted from outside of the body of the patient.

The first and second restriction elements 10', 10" are connected to the control unit 20 by means of a first and second fluid conduit 162', 162". The fluid conduits 162', 162" and the first and second restriction element 10', 10" are preferably made from a biocompatible material such as silicone and/or polyurethane. The fluid conduits could be materially integrated in the restriction elements such that the number of joints are reduced, which reduces the risk of the rupture between the restriction elements and the fluid conduits 162', 162". The fluid conduits 162', 162" are further connected to a hydraulic pump 150' of the operation device 110 of the control unit 20. The hydraulic pump 150' is propelled by a motor 130 which could be connected to the hydraulic pump via a gear system 140 adapting the work created by the motor 130 to what is required by the hydraulic pump 130.

The control unit further comprises an energizing unit 190 which may be an accumulator by means of which energy can be stored in the body of the patient. The accumulator could for example be a rechargeable battery or a capacitor. The control unit also comprises a control system 195 comprising a processing unit for handling the control of the restriction device. The processing unit could be a single CPU (Central processing unit), or could comprise two or more processing units. For example, the processor may include a general purpose microprocessor, an instruction set processor and/or related chips sets and/or special purpose microprocessors such as ASICs (Application Specific Integrated Circuit). The processor may also comprise board memory for caching purposes. The control system 195 could be adapted to keep track of the lapsed time since the restriction device was last switched, and could include an I/O interface for receiving sensor input for the purpose of controlling the restriction device. The control system 195 could be wirelessly programmable form outside of body of the patient and the programming of the controlling could be based on a combination of lapsed time, real time, sensor input (which could be sensor input related to a functional parameter of the device or a physical parameter of the patient), patient input (by means of for example a remote control) and input by medical professionals, such that the restriction device can be programmed to function optimally. The optimal function of the restriction device could in many instances be a mediation between optimal restriction of the luminary organ and restriction with causes the least damage to the restricted tissue.

Turning again to the implanted control unit, the control unit 20 of the embodiment of FIG. 2a is fixated to the muscular layer M of the abdomen, by means of the main part 20' of the control unit 20 being placed on the inside of the muscular layer M and communication part 20" of the control unit 20 being placed on the outside of the muscular layer M, subcutaneously. The main part 20' and the communication part 20" are interconnected by means of an interconnecting portion 20'''. The interconnection of the main part 20' and the communication part 20" clamps the muscular layer M which fixates the control unit to the muscular layer M.

The communication part 20" of the control unit comprises a receiving/transmitting unit 120 adapted to receive information from a communication unit 30a and wireless energy from a wireless energy transmitter 30b of an external unit 200. The wireless energy may be in the form of an electromagnetic field transferred between a coil of the external unit 200 and a coil of the receiving unit 120, by means of the coils of the receiving unit 120 and external unit 200 functioning as electrical conductors inductively coupled to each other, forming a transformer like circuit for the purpose of transferring alternating electrical energy signals. The wireless energy could in alternative embodiments be in the form of a moving magnetic field magnetically connected to a movable structure of the implantable operation device 110 comprising magnets or magnetic material, such that the movable structure of the operable implant moves along with the moving magnetic field created in the external unit 200. The receiving/transmitting unit 120 could further be a combination unit adapted to receive wireless energy both in the form a moving magnetic field affecting a movable structure of the operation device, and as wireless energy generating electrical current on in the control unit 20 for operating the restriction device or charging the energizing unit 190.

In alternative embodiments, the implantable control unit may further comprise a push-button placed under the skin for providing force, information, or for overriding the automatic system of the control unit. Generally speaking, the control unit of the restriction device may control the restriction automatically according to a pre-programmed time-schedule or on the basis of input from any sensor sensing any possible physical parameter of the patient or any functional parameter of the device.

The control unit may comprise a feedback device for sending information from inside the patient's body to the outside thereof to give feedback information related to at least one functional parameter of the stretching device or restriction device or a physical parameter of the patient, thereby optimizing the performance of the restriction device. One preferred functional parameter of the device is correlated to the transfer of energy for charging the internal energizing unit.

The wireless energy supplied to the control unit may generally be transferred by means of any suitable Transcutaneous Energy Transfer (TET) device, such as a device including a primary coil arranged in the external unit 200 and a secondary coil arranged in the implanted control unit

20. When an electric current is fed through the primary coil, energy in the form of a voltage is induced in the secondary coil which can be used to operate the restriction device, e.g. after storing the incoming energy in an energizing unit 190, such as a battery or a capacitor. However, the present invention is generally not limited to any particular energy transfer technique, TET devices or energy storing devices, and any kind of wireless energy may be used.

The amount of energy received inside the body to the device may be compared with the energy used by the device. The term used by the device is then understood to include also energy stored by the device. The amount of transferred energy can be regulated by means of the external unit 200 based on the determined energy balance. In order to transfer the correct amount of energy, the energy balance and the required amount of energy can be determined by means of the control unit 20. The control unit 20 may thus be arranged to receive various measurements obtained by suitable sensors or the like, not shown, measuring certain characteristics of the restriction device, somehow reflecting the required amount of energy needed for proper operation of the restriction device. Moreover, the current condition of the patient may also be detected by means of suitable measuring devices or sensors, in order to provide parameters reflecting the patient's condition. Hence, such characteristics and/or parameters may be related to the current state of the restriction device, such as power consumption, operational mode and temperature, as well as the patient's condition reflected by, e.g., body temperature, blood pressure, heartbeats and breathing. Alternatively or additionally, characteristics of the energizing unit 190, also reflecting the required amount of energy, may be measured as well. Characteristics of the energizing unit 190 may be related to the current state of the battery, such as voltage, temperature, etc. In order to provide sufficient voltage and current to the restriction device, and also to avoid excessive heating, it is clearly understood that the energizing unit should be charged optimally by receiving a correct amount of energy, i.e. not too little or too much. Energizing unit characteristics may be measured on a regular basis to determine the current state of the energizing unit, which then may be stored as state information in a suitable storage means in the control unit 20. Thus, whenever new measurements are made, the stored energizing unit state information can be updated accordingly. In this way, the state of the energizing unit can be "calibrated" by transferring a correct amount of energy, so as to maintain the energizing unit in an optimal condition.

The control unit 20 may be adapted to determine the energy balance and/or the currently required amount of energy, (either energy per time unit or accumulated energy) based on measurements made by the above-mentioned sensors or measuring devices on the restriction device, or the patient, or an energizing unit if used, or any combination thereof.

Sensor measurements from the inside of the patients body can be transmitted directly to the external unit 200 wherein the energy balance and/or the currently required amount of energy can be determined by the external unit 200, thus integrating the above-described function of the control unit 20 in the external unit 200. The energy balance and the currently required amount of energy can be determined by the external unit 200 based on sensor measurements.

The control unit 20 may employ feedback of information indicating the required energy, which is more efficient than previous solutions because it is based on the actual use of energy that is compared to the received energy, e.g. with respect to the amount of energy, the energy difference, or the energy receiving rate as compared to the energy rate used by the restriction device. The different parameters discussed above would thus be used if relevant and needed and then as a tool for determining the actual energy balance. However, such parameters may also be needed per se for any actions taken internally to specifically operate the restriction device.

The control unit and external unit may operate basically in the following manner. The energy balance is first determined by the control unit 20. A control signal reflecting the required amount of energy is also created by the control unit 20, and the control signal is transmitted from the control unit 20 to the external unit 200. Alternatively, the energy balance can be determined by the external unit 200 instead depending on the implementation, as mentioned above. In that case, the control signal may carry measurement results from various sensors. The amount of energy emitted by the external unit 200 can then be regulated by the external unit 200, based on the determined energy balance, e.g. in response to the received control signal. This process may be repeated intermittently at certain intervals during ongoing energy transfer, or may be executed on a more or less continuous basis during the energy transfer. The amount of transferred energy can generally be regulated by adjusting various transmission parameters such as voltage, current, amplitude, wave frequency and pulse characteristics. A method is thus provided for controlling transmission of wireless energy supplied to the restriction device implanted in the patient. The wireless energy is transmitted from the external unit outside the patient and is received by the control unit located inside the patient, the control unit being connected to the restriction device for directly or indirectly supplying received energy thereto. An energy balance is determined between the energy received by the control unit and the energy used for the restriction device. The transmission of wireless energy from the external unit is then controlled based on the determined energy balance.

The control unit may additionally comprise a reverse device for altering the direction of an electrical motor or a fluid flow. The reverse device could for example be a valve member, a mechanical gear, or a device for changing current polarity, or a device for altering an alternating current, such as a converter.

The communication part 20″ further comprises a subcutaneous injection port 126 by means of which the fluid level in the hydraulic restriction device can be calibrated. The subcutaneous injection port 126 could have a self sealing membrane, for example made from hard silicone, such that an injection needle can be inserted through the skin S of the patient and through the self sealing membrane and removed substantially without the occurrence of any leakage.

The interconnecting portion 20‴ comprises a fluid conduit for transferring fluid from the injection port 126 of the communication part 20″ to the hydraulic pump or a fluid reservoir in fluid connection with the fluid pump 150′. The interconnecting portion 20‴ further comprises an electrical lead for transferring electrical power received at the receiving/transmitting unit 120 or transferring information and/or control signals received from or to be transmitted by the receiving/transmitting unit 120

Turning now to the external wireless energy transmitter 30b for transmitting wireless energy. The wireless energy transmitter 30b comprises a coil and an electronic circuit connected to the second coil, wherein the coil of the energy transmitter 30b transmits wireless energy which is received by the coil of the implanted receiving/transmitting unit 120. The control system 195 of the control unit 20 further comprises a power switch for switching the connection of the coil of the receiving/transmitting unit 120 on and off, such that feedback information related to the transfer of wireless energy can be received by the wireless energy transmitter 30*b* in the form of an impedance variation in the load of the external coil.

I alternative embodiments, the wireless energy signal transmitted by the external wireless energy transmitter 30*b* may include a wave signal selected from the following: a sound wave signal, an ultrasound wave signal, an infrared light signal, a visible light signal, an ultra violet light signal, a laser light signal, a micro wave signal, a radio wave signal, an x-ray radiation signal and a gamma radiation signal. The wireless energy-transmission device 30*b* may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Now turning to the communication unit 30*a*. The communication unit may 30*a* function as a wireless remote control for transmitting a wireless control signal for non-invasively controlling the apparatus. The wireless remote control could be operated by the patient such that the generated control signal is a patient input control signal. The wireless remote control could additionally be used by medical professionals for calibrating the device or altering the settings. The implanted control unit 20 may be adapted to automatically control the restriction device and the received control signal from the wireless remote control could be a control signal to alter the programming of the control unit 20, and thus altering the automatic function of the control unit 20. Alternatively, the control signal may be adapted to override the automatic operation by the control unit 20. In yet an alternative embodiment, the external unit 200 comprises the functionality keeping track of the automated operation of the control unit 20. I.e. the external unit 200 sends a control signal automatically to the implanted control unit 20 when it is time to switch restriction position.

In alternative embodiments, the control unit may additionally comprise a fixation member adapted to directly or indirectly fixate at least a portion of the control unit to at least one muscular fascia and/or at least one bone fascia and/or at least one cortical bone layer and/or at least one muscular layer and/or fibrotic tissue and/or any part of the abdominal wall and/or any part of the subcutaneous space and its surroundings in the body.

In the example where the hydraulic implantable restriction device is a restriction device adapted to restrict the urethra of the patient for treating urinary incontinence, the patient may operate, via the wireless remote control, the releasing of the restriction device for enabling release of urine. A different version of the communication unit 30*a* operated by the medical professional could have the capabilities of changing the settings of the restriction device, for example by changing the frequency with which the restriction device switches between restricting a first and second portion of the urethra. The professional version of the communication unit could also have the capabilities of receiving feedback from the restriction device. The feedback could for example be related to the energy level at the energizing unit 190 of the control unit, the fluid level of the hydraulic restriction device, number of operations that the restriction device has performed, or any other functional parameter of the device or physiological parameter of the patient.

The wireless signals used by the communication unit 30*a* may include a frequency, amplitude, or phase modulated signal or a combination thereof. Alternatively, the wireless signal could include an analogue or a digital signal, or a combination of an analogue and digital signal. The wireless control signal may comprise an electric or magnetic field, or a combined electric and magnetic field. The communication unit 30*a* may additionally transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

The control unit 20 is enclosed by en enclosure such that the control unit is protected from bodily fluids. The enclosures may be an enclosure made from one of or a combination of: a carbon based material (such as graphite, silicon carbide, or a carbon fiber material), a boron material, a polymer material (such as silicone, Peek®, polyurethane, UHWPE or PTFE,), a metallic material (such as titanium, stainless steel, tantalum, platinum, niobium or aluminum), a ceramic material (such as zirconium dioxide, aluminum oxide or tungsten carbide) or glass. In any instance the enclosure should be made from a material with low permeability, such that migration of fluid through the walls of the enclosure is prevented.

FIG. 2*b* shows an embodiment of a hydraulic pump 150' for implantation. The hydraulic pump is a peristaltic hydraulic pump 150' adapted pump and thus transport a hydraulic fluid to the first and second restricting element 10', 10". The peristaltic pump 150' is adapted to be connected to force output of a motor, such as the motor 130 in the control unit 20 of FIG. 2*a*. The implantable peristaltic pump 150' comprises a deflectable hollow member 152 for fluid transportation, in form of a tubing made from a resilient material, such as an elastomeric polymer material, such as silicone, Parylene® coated silicone, NBR, Hypalon, Viton, PVC, EPDM, Polyurethane or Natural Rubber. The deflectable hollow member 152 is adapted to be deflected by an operable compression member 153 or "wiper", adapted to engage and compress the hollow member 152, and thus transport the hydraulic fluid. The compression member 153 is propelled by the motor (130 in FIG. 2*a*). The hollow member 152 is placed inside a peristaltic pump housing 151, such that the hollow member 152 is compressed between the operable compression member 153. The peristaltic pump 150' enables the hydraulic fluid to be completely separated from the bodily fluids, such that the hydraulic fluid can be transported without the risk of leakage.

The deflectable hollow member 152 is connected to or integrated with fluid conduits 162', 162", which in turn is connected to or integrated with the hydraulic restriction elements 10', 10". When the compression member 153 is propelled in a clockwise direction, it creates a peristaltic wave which presses hydraulic fluid through the hollow member 152 and further through the first fluid conduit 162' and to the first restriction element 10'. When the first restriction element 10' is inflated by the fluid, it restricts a first portion of the luminary organ L. When the compression member 153 is propelled in a counter clockwise direction, it creates a peristaltic wave which presses hydraulic fluid through the hollow member 152 and further through the second fluid conduit 162" and to the second restriction element 10". When the second restriction element 10" is inflated by the fluid, it restricts a first portion of the luminary organ L, such as shown in FIG. 2*a*. By the construction of the embodiment of FIG. 2*b*, the restricted portion can be switched from the first to the second by altering the direction of movement of the compression member 153. The embodiment shown in FIG. 2b enables the fluid of the hydraulic restriction device to be entirely encapsulated such that the risk of leakage is minimized.

The first and second restriction elements 10', 10" each comprises fixation portions 14'a, 14"a, 14'b, 14"b adapted to be interconnected such that the restriction element forms a closed loop encircling the luminary organ L. The first ends of the fixation portions 14'a, 14"a may be connected to the second ends of the fixation portions 14'b, 14"b by means of for example sutures or staplers.

FIG. 3 shows an embodiment of implantable hydraulic restriction device in which the restriction elements 10', 10" are identical to the restriction elements described under reference to FIGS. 2a and 2b. The control unit 20, or part of the control unit operating the hydraulic restriction device differ from that of FIG. 2b in that the control unit comprises a torus shaped reservoir made from a resilient material, such as silicone, Parylene® coated silicone, NBR, Hypalon, Viton, PVC, EPDM, Polyurethane or Natural Rubber, such that the walls of the reservoir are movable such that the reservoir 160 can be compressed and thereby functioning as a non-valve pump for moving fluid from the reservoir 160 to the restriction elements 10', 10". The torus shaped reservoir is connected to an implantable valve member 40 (which may in alternative embodiments be integrated in the control unit 20). The implantable valve member 40 comprises a movable fluid guide 44 which is controllable to rotate within the housing 41 of the valve member 40. By means of the valve member 40, the fluid from the reservoir 160 conveyed through the fluid conduit 162 can be controlled by the valve 40, by means of the fluid guide 44, to either be conveyed through a first fluid conduit 162' to a first restriction element 10' or through a second fluid conduit 162" to a second restriction element 10". The implantable valve 40 is operated by an electrical motor or solenoid (not shown) connected to the valve guide 44.

Now, turning to the control unit 20, the control unit comprises a hydraulic pump in the form of a torus shaped reservoir 160 adapted to contain a hydraulic fluid. The torus shaped reservoir 160 is adapted to be compressed by a radially extending engaging member 444 operated by a threaded member 441 connected to an operation device 110' comprising an electrical motor and a gear system. The torus shaped reservoir 160 is preferably made from a material which is elastic enough to create suction, such that the fluid from the restriction elements is returned to the torus shaped reservoir 160 when the pressure from the radially extending engaging member 444 is released. The operation device 110' could for example comprise the combination of motor and gear system as described in any of FIG. 22, 23, 24 or 25. The control unit further comprises an enclosure 161 enclosing the torus shaped reservoir 160 and the radially extending engaging member 444. The additional enclosure 161 comprises a sealing member 167 adapted to seal between the additional enclosure and the fluid conduit 162 adapted to transport the hydraulic fluid from the torus shaped reservoir 160 to the implantable valve. The additional enclosure further seals the operation device 110' from the bodily fluids and reduces the risk that fibrotic tissue in-growth affects the operation of the operation device 110'. Examples of the operation of the control unit 20 is described in further detail with reference to FIGS. 22, 23, 24 and 25.

FIG. 4 shows an overview of a female patient in whom the hydraulic implantable restriction device has been implanted such that the restriction elements are restricting the fallopian tubes F of the patient and thus hindering eggs travelling through the fallopian tubes from reaching the uterus UT of the patient. The implantable hydraulic restriction device thus functions as an implantable contraceptive system.

FIGS. 5a and 5b shows the restriction device adapted to restrict the fallopian tubes F in further detail. The restriction device comprises the two restriction elements 10', 10" connected to a two-directional peristaltic pump 150' by means of a first and second fluid conduit 162', 162". The first and second peristaltic pump 150' and restriction element 10 may be connected to a single control unit controlling the two pumps 150' and restricting elements 10, alternatively, the first and second peristaltic pumps 150' are each connected to a control unit, such that the first and second peristaltic pumps 150' and restriction elements 10 are controlled individually.

The peristaltic pumps 150' of the two restriction devices are controlled such that the restricted portion of the fallopian tubes F is continuously switched such that the restricted tissue is allowed to rest from the pressure exerted by the restricting elements 10', 10". When a portion of the fallopian tube is restricted, the blood flow of that particular portion of the fallopian tube is hampered, which creates a risk that the portion suffers from ischemia which may cause irreversible necrosis of the restricted tissue. By constantly switching the restricted portion the risk of necrosis or other damage to the tissue of the patient is considerably reduced. The switching could be performed on the basis of a lapsed time and/or on the basis of the patient using the device for the purpose of releasing eggs in the fallopian tube F. I.e. the first restriction elements 10' can be used for restricting the fallopian tube F until the patient operates the restriction device for releasing one or more eggs, after which the second restriction element 10" is used for restricting the fallopian tube F. It is also conceivable to program the control unit 20 such that the switching occurs on the basis of both lapsed time and patient usage. In alternative embodiments, or as a complement to the previously described control method, the device may be controlled on the basis of sensor input. The sensor providing sensor input could be a sensor sensing a functional parameter of the device, such as pressure, mechanical elongation or available energy, or a physical parameter of the patient, such as temperature, saturation, blood pressure or an ischemia marker such as lactate. Please note that any of the embodiments of hydraulic restriction devices herein may be used for the purpose of restricting the fallopian tube and that the particular embodiment shown is only to be seen as an example.

Figure 7:
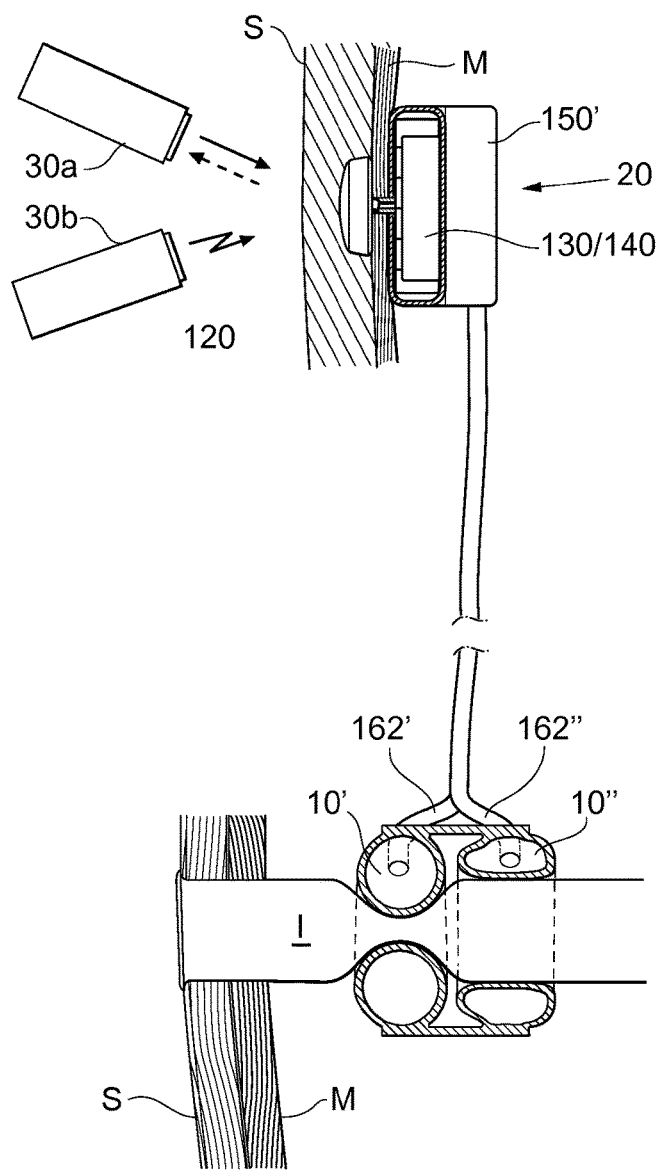
FIG. 7 shows the implantable hydraulic restriction device in further detail, when implanted for restricting a stoma of the patient.

FIG. 6 and FIG. 7 shows the implantable hydraulic restriction device according to the embodiment described in further detail with reference to FIGS. 2a and 2b, when implanted in the body of a patient positioned on a stoma created using a portion of the patient's intestine I. The stoma penetrates the muscular layer M of the abdominal wall and the skin S of the patient for the purpose of allowing matter which have passed through the intestines I of the patient to exit the body, when a portion of the patient's intestine I has been removed. When a portion of the intestine I is restricted, the blood flow of that particular portion of the intestine I is hampered, which creates a risk that the portion suffers from ischemia, which may cause irreversible necrosis of the restricted tissue. By constantly switching the restricted portion the risk of necrosis or other damage to the tissue of the patient is considerably reduced. The switching could be performed on the basis of a lapsed time and/or on the basis of the patient using the device for the purpose of releasing the intestinal content. I.e. the first restriction element 10' can be used for restricting the stoma until the patient operates the restriction device for emptying the intestine I after which the second restriction element 10" is used for restricting the stoma. It is also conceivable to program the control unit 20 such that the switching occurs on the basis of both lapsed time and patient usage. In alternative embodiments, or as a complement to the previously described control method, the device may be controlled on the basis of sensor input. The sensor providing sensor input could be a sensor sensing a functional parameter of the device, such as pressure, mechanical elongation or available energy, or a physical parameter of the patient, such as temperature, saturation, blood pressure or an ischemia marker such as lactate. Please note that any of the embodiments of hydraulic restriction devices herein may be used for the purpose of restricting the intestine and that the particular embodiment shown is only to be seen as an example.

Figure 8:
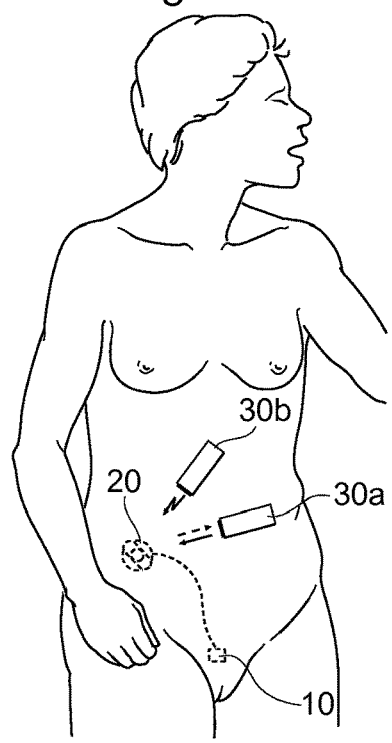
FIG. 8 shows an overview of a patient when the implantable hydraulic restriction device has been implanted for restricting the urethra of the patient.
Figure 9A:
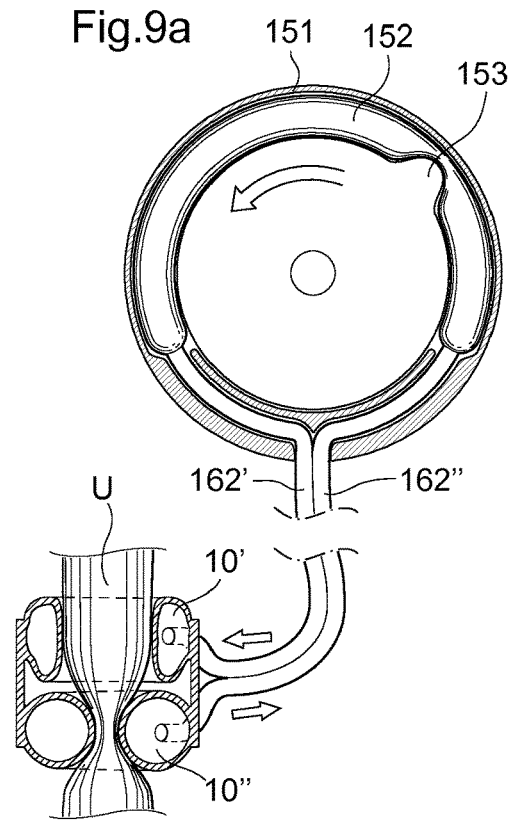
FIG. 9a shows the urethra of the patient when the implantable hydraulic restriction device has been implanted.
Figure 9B:
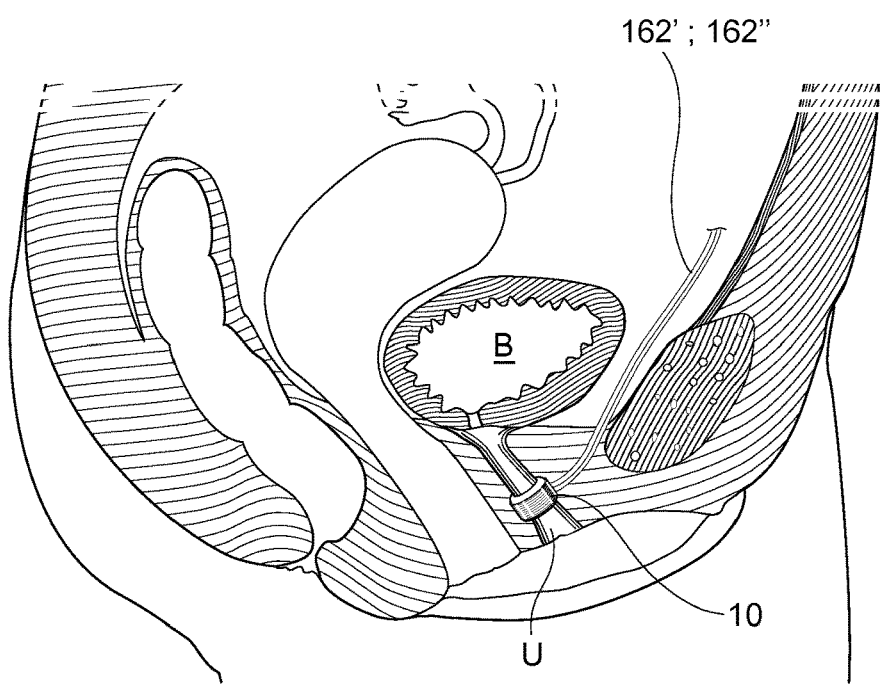
FIG. 9b shows a sectional view of the patient when the implantable hydraulic restriction device has been implanted for restricting the urethra.

FIGS. 8, 9*a* and 9*b* shows the implantable hydraulic restriction device according to the embodiment described in further detail with reference to FIGS. 2*a* and 2*b*, when implanted in the body of a patient positioned on the urethra U for the purpose restricting the flow of urine in the urethra for treating incontinence. When a portion of the urethra U is restricted, the blood flow of that particular portion of the urethra U is hampered, which creates a risk that the portion suffers from ischemia, which may cause irreversible necrosis of the restricted tissue. By constantly switching the restricted portion the risk of necrosis or other damage to the tissue of the patient is considerably reduced. The switching could be performed on the basis of a lapsed time and/or on the basis of the patient using the device for the purpose of releasing urine. I.e. the first restriction element 10' can be used for restricting the urethra until the patient operates the restriction device for emptying the urinary bladder B after which the second restriction element 10" is used for restricting the urethra U. It is also conceivable to program the control unit 20 such that the switching occurs on the basis of both lapsed time and patient usage. In alternative embodiments, or as a complement to the previously described control method, the device may be controlled on the basis of sensor input. The sensor providing sensor input could be a sensor sensing a functional parameter of the device, such as pressure exerted on the restrictions elements 10', 10" from the urine in the bladder B and urethra U, mechanical elongation or available energy, or a physical parameter of the patient, such as temperature, bladder expansion, nerve impulses, saturation, blood pressure or an ischemia marker such as lactate. Please note that any of the embodiments of hydraulic restriction devices herein may be used for the purpose of restricting the urethra and that the particular embodiment shown is only to be seen as an example.

When the restriction device is used for restricting the urethra or intestine of the patient the device may function such that the passage way for urine and fecal matter is open when each of the restriction elements are half full, which in the embodiment of FIG. 9*a* corresponds to the compression member 153 being placed in the middle of the hollow member 152. When the patient needs to open the passageway, the compression member 153 is moved to the middle and paused while the patient requires the passageway to be open, after which the compression member 153 continues to the opposite end position closing the other restriction element. As the restriction needs to be opened anyway, the switching of restriction elements does not create any additional energy consumption, which makes the solution energy efficient.

Figure 10:
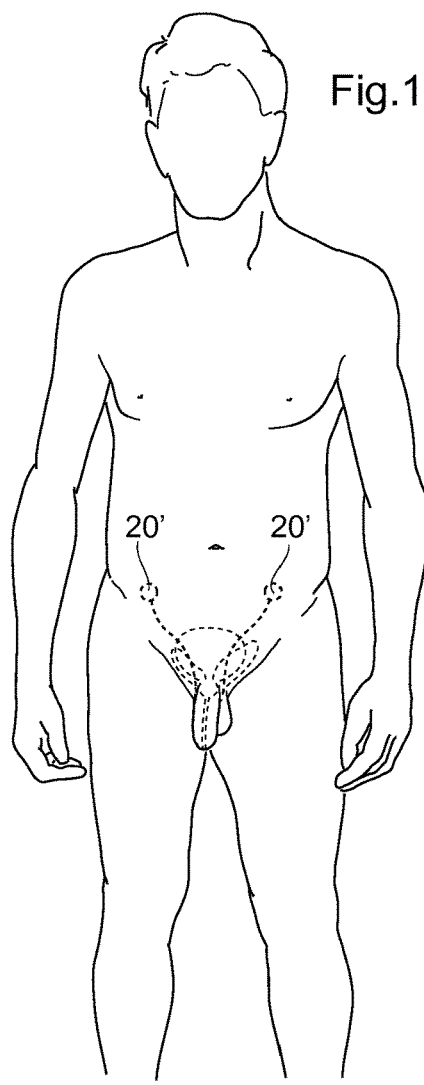
FIG. 10 shows an overview of a patient when the implantable hydraulic restriction device has been implanted for restricting the vas deferens of the patient.
Figure 11A:
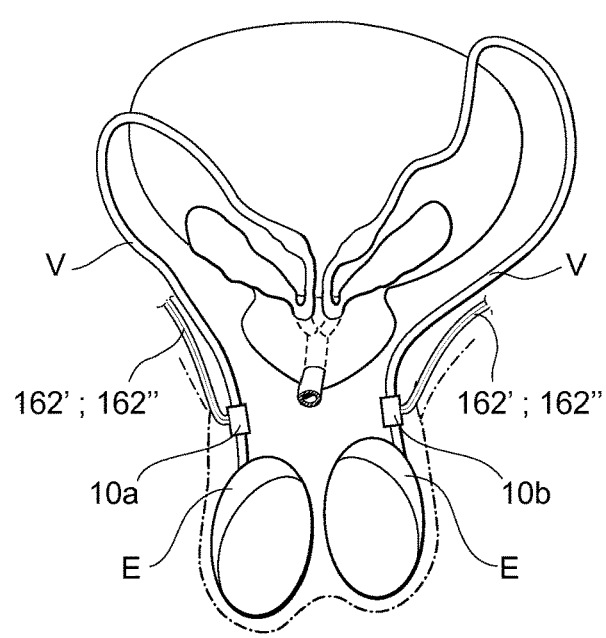
FIG. 11a shows the scrotum and the vas deferens of the patient in further detail, when the hydraulic restriction device has been implanted.
Figure 11B:
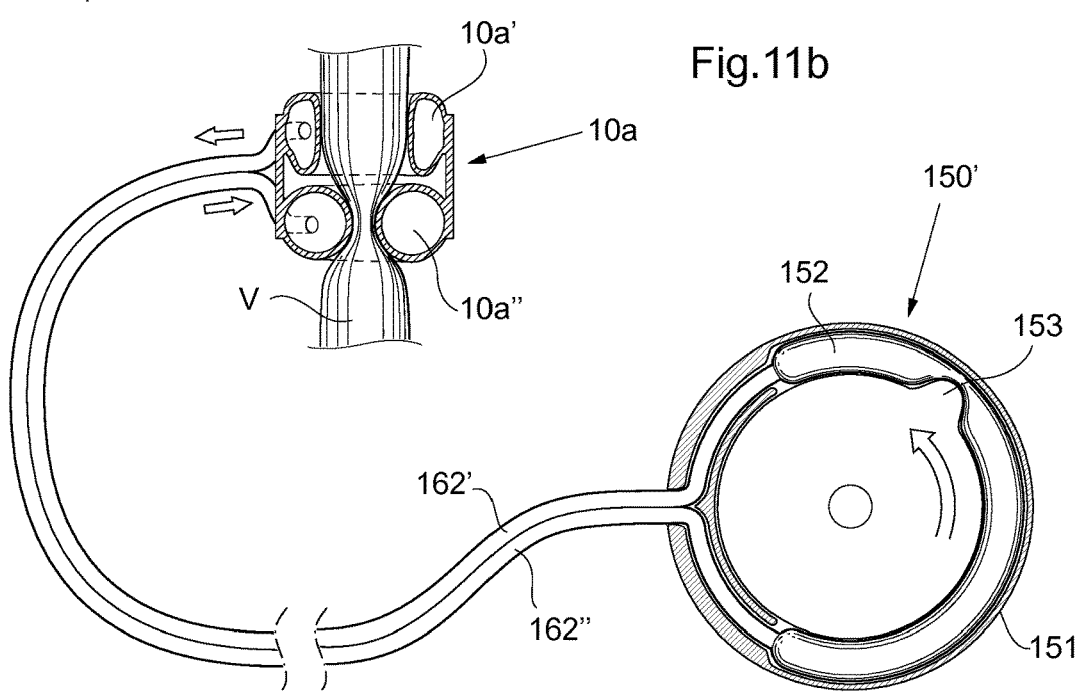
FIG. 11b shows the vas deferens of the patient schematically, when the hydraulic restriction device has been implanted.

FIGS. 10, 11*a* and 11*b* shows the implantable hydraulic restriction device according to the embodiment described in further detail with reference to FIGS. 2*a* and 2*b*, when implanted in the body of a patient positioned on the vas deferens V for the purpose restricting the flow of sperm from the epididymis E for the purpose of functioning as a contraceptive or a reversible sterilization. When a portion of the vas deference V is restricted, the blood flow of that particular portion of the vas deferens V is hampered, which creates a risk that the portion suffers from ischemia, which may cause irreversible necrosis of the restricted tissue. By constantly switching the restricted portion the risk of necrosis or other damage to the tissue of the patient is considerably reduced. The switching could be performed on the basis of a lapsed time and/or on the basis of input from the patient. It is also conceivable to program the control unit 20 such that the switching occurs on the basis of both lapsed time and patient input. In alternative embodiments, or as a complement to the previously described control method, the device may be controlled on the basis of sensor input. The sensor providing sensor input could be a sensor sensing a functional parameter of the device, mechanical elongation or available energy, or a physical parameter of the patient, such as temperature, nerve impulses, saturation, blood pressure or an ischemia marker such as lactate. Please note that any of the embodiments of hydraulic restriction devices herein may be used for the purpose of restricting the vas deferens and that the particular embodiment shown is only to be seen as an example.

FIGS. 12, 13*a* and 13*b* shows the implantable hydraulic restriction device according to the embodiment described in further detail with reference to FIGS. 2*a* and 2*b*, when implanted in the body of a patient positioned on the large intestine in the end region thereof in proximity to the anus of the patient for the purpose restricting the large intestine and thus function as an artificial sphincter restricting the flow of intestinal content and thus treating anal incontinence. When a portion of the large intestine I is restricted, the blood flow of that particular portion of the intestine I is hampered, which creates a risk that the portion suffers from ischemia, which may cause irreversible necrosis of the restricted tissue. By constantly switching the restricted portion the risk of necrosis or other damage to the tissue of the patient is considerably reduced. The switching could be performed on the basis of a lapsed time and/or on the basis of the patient using the device for the purpose of releasing the intestinal content. I.e. the first restriction element 10' can be used for restricting the intestine I until the patient operates the restriction device for emptying the intestine I after which the second restriction element 10" is used for restricting the intestine I. It is also conceivable to program the control unit 20 such that the switching occurs on the basis of both lapsed time and patient usage. In alternative embodiments, or as a complement to the previously described control method, the device may be controlled on the basis of sensor input. The sensor providing sensor input could be a sensor sensing a functional parameter of the device, such as pressure exerted on the device by intestinal content, mechanical elongation or available energy, or a physical parameter of the patient, such as temperature, saturation, blood pressure, the presence of intestinal content in the intestine I (which for example could be sensed by means of ultrasound or electric resistance) or an ischemia marker such as lactate. Please note that any of the embodiments of hydraulic restriction devices herein may be used for the purpose of restricting the large intestine and that the particular embodiment shown is only to be seen as an example.

Figure 14:
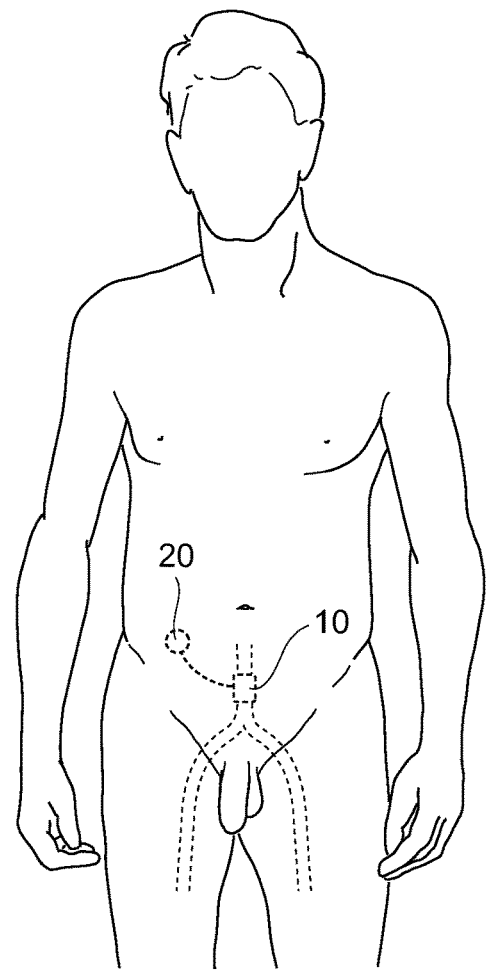
FIG. 14 shows an overview of a patient when the implantable hydraulic restriction device has been implanted for restricting an aneurysm of the patient.
Figure 15:
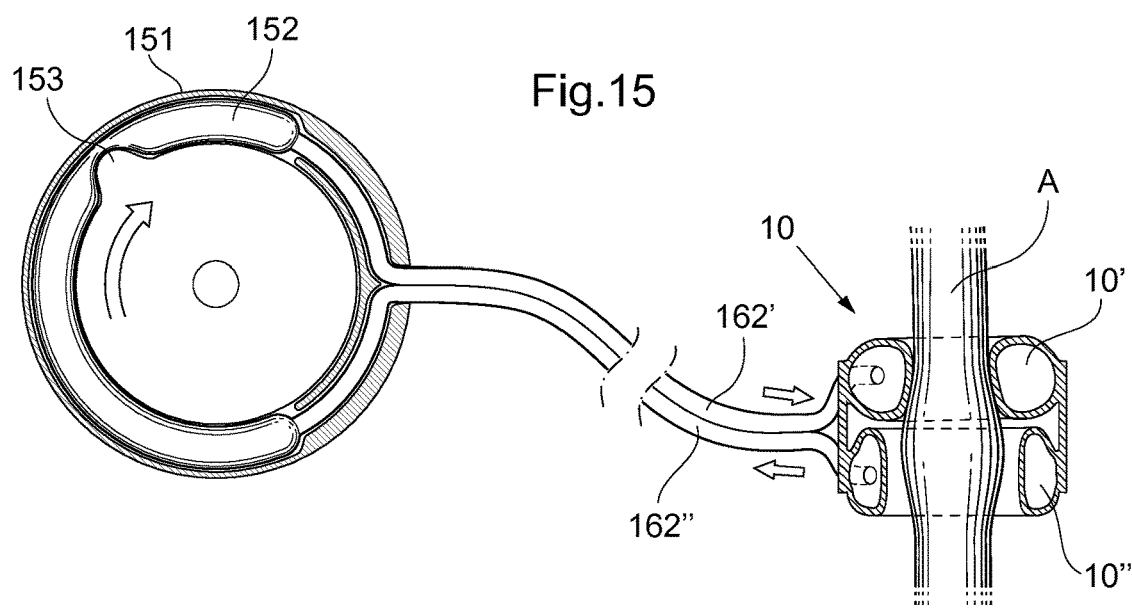
FIG. 15 shows the abdominal aorta of the patient schematically, when the hydraulic restriction device has been implanted.

FIGS. 14 and 15 shows the implantable hydraulic restriction device according to the embodiment described in further detail with reference to FIGS. 2a and 2b, when implanted in the body of a patient positioned on the abdominal aorta A for the purpose restricting an aortic aneurysm. Aortic aneurysm is caused by the weakening of the wall of the abdominal aorta A and creates a balloon like bulge. As the aneurysm grows the wall of the aorta is further weakened which eventually leads to the rupture of the aorta which in many instances is fatal. The hydraulic restriction device restricts the further expansion of the abdominal aorta A by the restricting elements 10 encircling the aorta A and pressing against the aorta A by means of the hydraulic fluid supplied to the restricting elements. When a portion of a blood vessel, such as the abdominal aorta A is restricted, the blood flow of that particular portion of the vessel is hampered, which creates a risk that the portion suffers from ischemia, which may cause irreversible necrosis of the restricted tissue. By constantly switching the restricted portion the risk of necrosis or other damage to the tissue of the patient is considerably reduced. The switching could be performed on the basis of a lapsed time and/or on the basis of input from the patient and/or a medical professional. It is also conceivable to program the control unit 20 such that the switching occurs on the basis of both lapsed time and input. In alternative embodiments, or as a complement to the previously described control method, the device may be controlled on the basis of sensor input. The sensor providing sensor input could be a sensor sensing a functional parameter of the device, such as pressure exerted from the aneurysm, mechanical elongation or available energy, or a physical parameter of the patient, such as temperature, nerve impulses, saturation, blood pressure or an ischemia marker such as lactate. Please note that any of the embodiments of hydraulic restriction devices herein may be used for the purpose of restricting an aneurysm and that the particular embodiment shown is only to be seen as an example.

Figure 16:
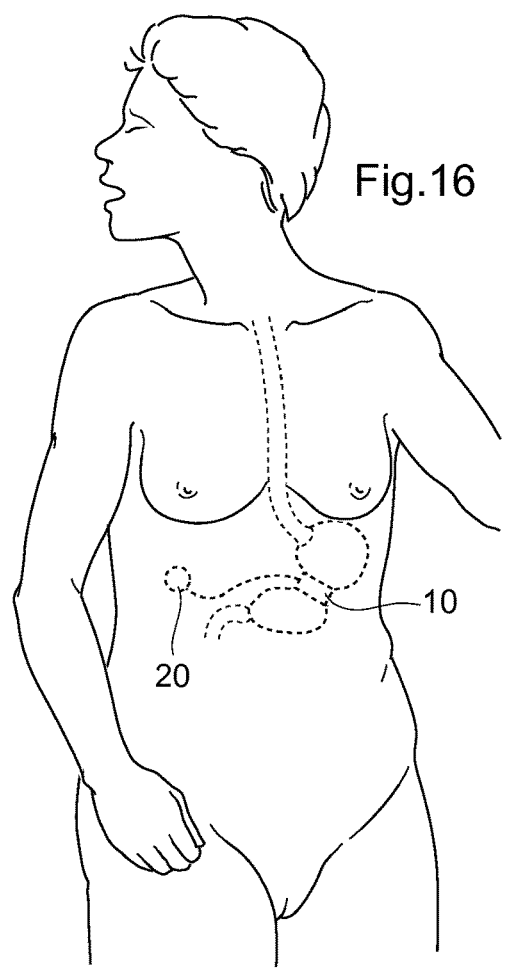
FIG. 16 shows an overview of a patient when the implantable hydraulic restriction device has been implanted for restricting the stomach of the patient.
Figure 17A:
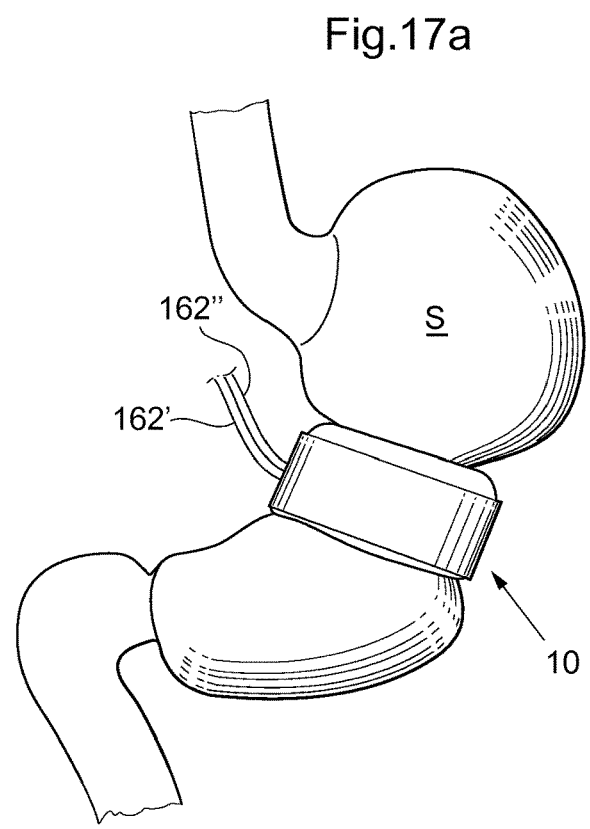
FIG. 17a-17c shows three different embodiments of the hydraulic restriction device implanted for restricting the stomach of the patient.
Figure 17B:
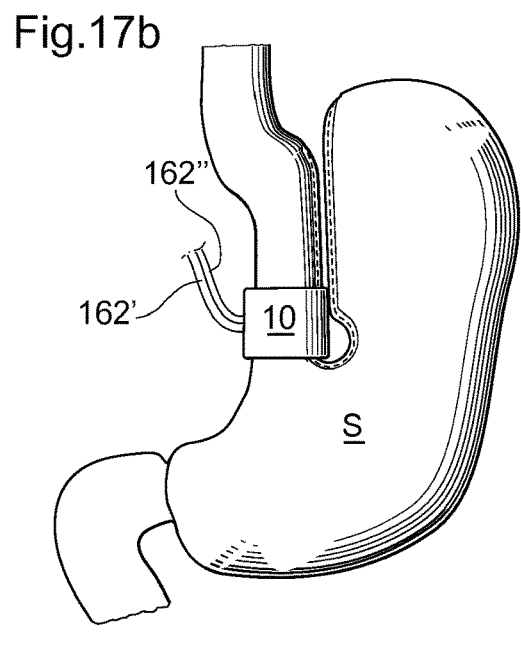
Figure 17C:
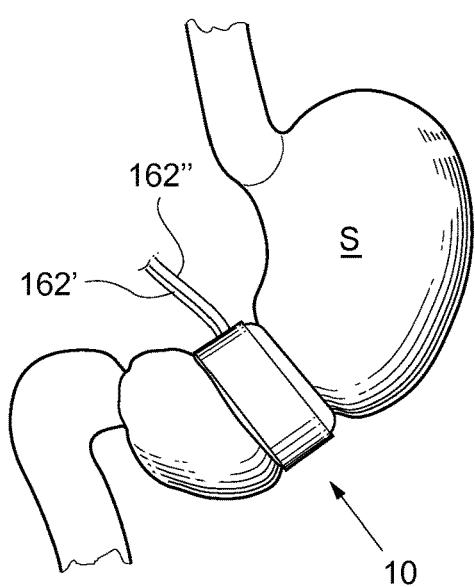

FIGS. 16 and 17a shows the implantable hydraulic restriction device according to the embodiment described in further detail with reference to FIGS. 2a and 2b, when implanted such that the restriction elements 10 encircles a portion of the stomach S of the patient for restricting the food passage way of the stomach S for reducing the nutrient uptake and the ability for the patient to ingest food and thus inducing weight loss in the patient. FIG. 17b shows an alternative way of restricting the stomach of the patient, by using the hydraulic restriction device in vertical banded gastroplasty (VBG) and FIG. 17c shows yet another alternative embodiment for restricting the food passageway of the stomach in which the restriction elements 10 are placed at the lower portion of the stomach S. The fluid conduits 162', 162" connects the restriction elements to a control unit, which could be the control unit of any of the embodiments herein. When a portion of the stomach S is restricted, the blood flow of that particular portion of the stomach S is hampered, which creates a risk that the portion suffers from ischemia, which may cause irreversible necrosis of the restricted tissue. By constantly switching the restricted portion the risk of necrosis or other damage to the tissue of the patient is considerably reduced. The switching could be performed on the basis of a lapsed time and/or on the basis of input from the patient and/or a medical professional. It is also conceivable to program the control unit 20 such that the switching occurs on the basis of both lapsed time and input.

In alternative embodiments, or as a complement to the previously described control method, the device may be controlled on the basis of sensor input. The sensor providing sensor input could be a sensor sensing a functional parameter of the device, such as pressure exerted from stomach activity, mechanical elongation or available energy, or a physical parameter of the patient, such as temperature, nerve impulses, saturation, blood pressure, acidity in the stomach, blood glucose level, stomach contraction or any other indicator of the patient eating, or an ischemia marker such as lactate. Please note that any of the embodiments of hydraulic restriction devices herein may be used for the purpose of restricting an aneurysm and that the particular embodiment shown is only to be seen as an example.

Figure 18A:
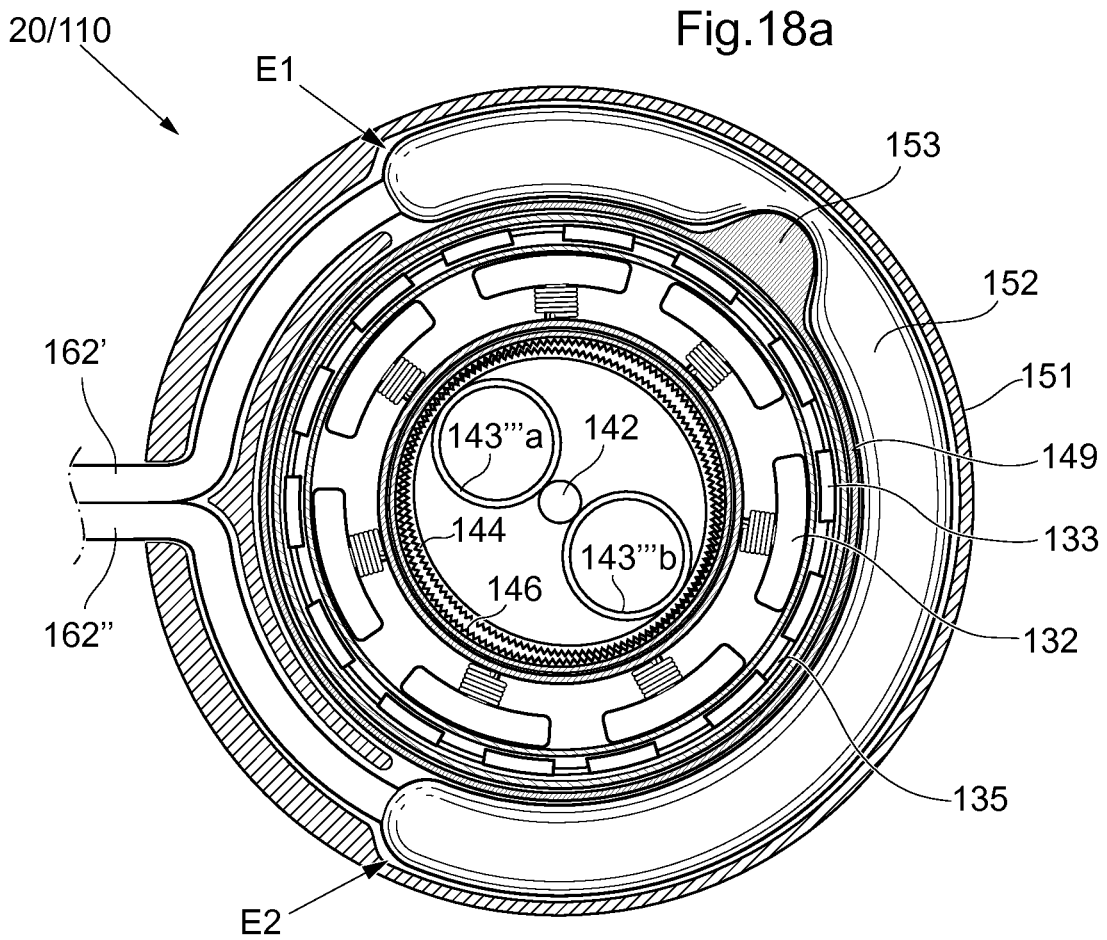
FIG. 18a shows a sectional top-view of an embodiment of a control unit for use in the implantable hydraulic restriction device.
Figure 18B:
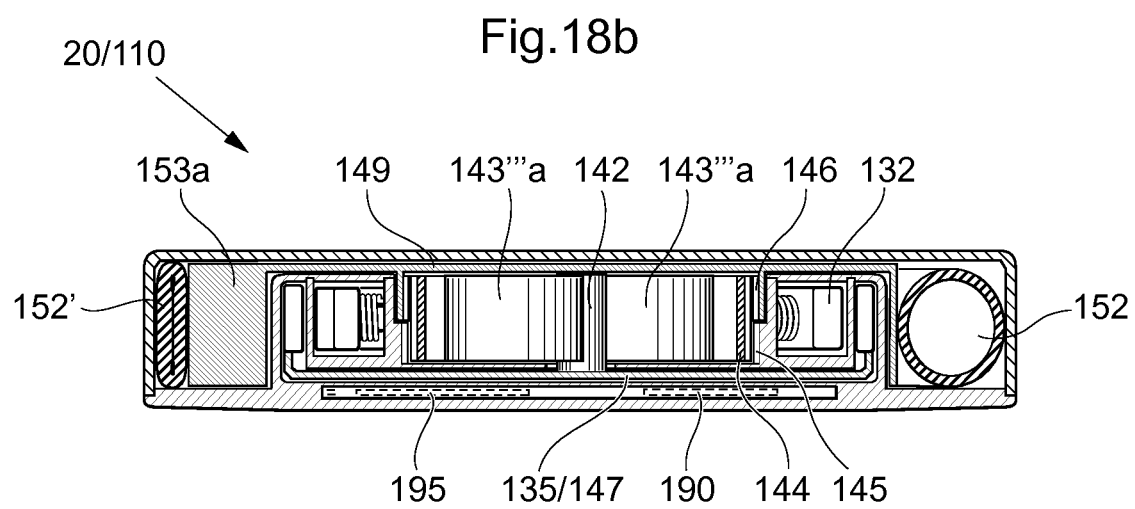
FIG. 18b shows a sectional side-view of an embodiment of a control unit for use in the implantable hydraulic restriction device.

FIGS. 18a and 18b shows an embodiment of a control unit 20 comprising an operation device 110, which may be used as control unit in any of the embodiments describes herein. The operation device 110 comprises a peristaltic hydraulic pump, such as further described with reference to FIGS. 2b and 26. The peristaltic pump comprises a hollow member 152 for fluid transportation integrated with the fluid conduits 162', 162" conveying fluid to the restriction elements of the fluid restriction device. The peristaltic pump further comprises an operable compression member 153 adapted to engage and compress the hollow member 152. The compression member 153 is connected to a rotating force output 149 of a gear system having a radially extending portion transferring force from the gear system to a cylindrical portion of the force output 149, to which the compression member 153 is fixated. Both the electrical motor and the gear system of the operation device is placed inside the peristaltic pump.

In further detail, the coils 132 of the electrical motor is connected by means of leads (not shown) to the control system 195 of the control unit 20 which in turn is connected to a energizing unit 190. The control system 195 generates an alternating current (AC) by means of a converter which is used to energize the coils 132. The AC thus sequentially energizes the coils 132 such that a propagating magnetic field is created in the coils 132 propelling the magnets 133 fixated to a rotatable structure 135. The rotatable structure 135 is in turn connected to a force input 142 of the gear system, such that the force input propels operable elements 143'''a, 143'''b deflecting the first gear 144 of the gear system and causing relative rotation between the third gear 146 and the second gear 145 which propels the force output 149 of the gear system which is in direct connection with the operable compression member 153. The detailed operation and alternative embodiments of the gear system is described with reference to FIGS. 20a-21d. The hollow member 152 forms ¾ of a loop encircling the electrical motor and the gear system, and the compressing member 153 compresses the hollow member 152 towards the outer periphery of the loop and against the housing 151 which is a portion of the enclosure of the operation device. The control system 195 controls the electrical motor such that the compressing member 153 is propelled in a first direction towards a first end portion E1 of the hollow member 152. The compression of the hollow member 152 transports fluid from the hollow member 152 through the first fluid conduit 162' and to the first restriction element (not shown) for restricting a first portion of a luminary organ. When the control system decides (based on for example a lapsed time or an input form a sensor or a person) that the restriction device should switch restricted portion of the luminary organ, the control system controls the electrical motor such that the compression member 153 compresses the hollow member 152 in the opposite direction towards a second end portion E2 of the hollow member 152 which transports fluid from the hollow member through the second fluid conduit 162" to the second restriction element (not shown) for restricting a second portion of the luminary organ.

When the restriction device is used for restricting the urethra or intestine of the patient the device may function such that the passage way for urine and fecal matter is open when each of the restriction elements are half full, which in the embodiment of FIG. 18a corresponds to the compression member 153 being placed in the middle of the hollow member 152. When the patient needs to open the passageway, the compression member 153 is moved from the first end portion E1 to the middle and paused while the patient requires the passageway to be open, after which the compression member 153 continues to the opposite end position E2 closing the restriction element (10" not shown in this fig.). As the restriction needs to be opened anyway, the switching of restriction elements does not create any additional energy consumption, which makes the solution energy efficient.

Figure 19A:
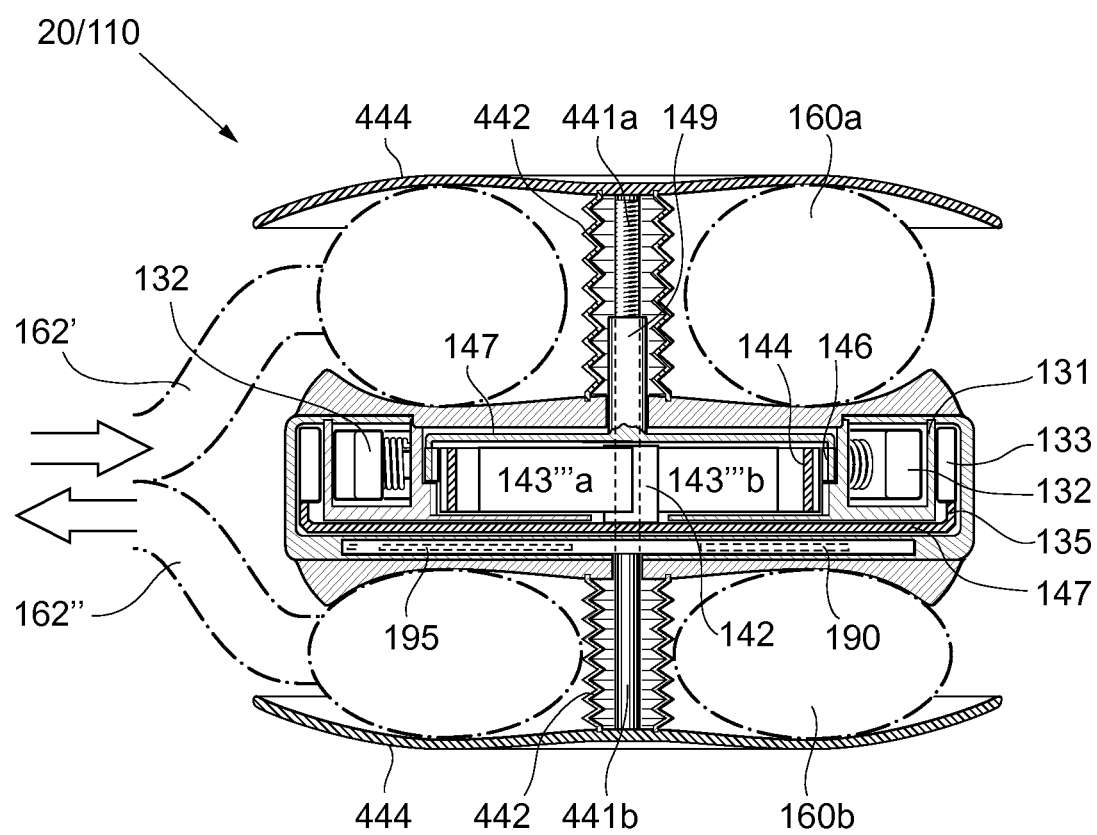
FIG. 19a shows a sectional side-view of an embodiment of a control unit for use in the implantable hydraulic restriction device.

FIG. 19a shows an embodiment of a control unit 20 comprising an operation device 110, which for may be used as control unit in any of the embodiments describes herein. In the embodiment shown in FIG. 19a, a motor and gear system (similar to the motor and gear system shown in FIGS. 18a and 18b) is placed between a first and second compressible reservoir 160a, 160b, similar to the reservoir described with reference to FIG. 3.

In detail, coils 132 of the electrical motor are connected by means of leads (not shown) to the control system 195 of the control unit 20 which in turn is connected to a energizing unit 190. The control system 195 generates an alternating current (AC) by means of a converter which is used to energize the coils 132. The AC thus sequentially energizes the coils 132 such that a propagating magnetic field is created in the coils 132 propelling the magnets 133 fixated to a rotatable structure 135 radially outside the coils 132. The rotatable structure 135 comprises a radially extending portion 147 adapted to transfer the force from the periphery of the rotatable structure 135 to the center of the rotatable structure 135 below the electrical motor and the gear system. The radially extending portion 147 transfers force to the force input 142 of the gear system, which in turn engages the operable elements 143'''a, 143'''b. The operable elements 143'''a, 143'''b engages the inside of a first gear 144 in two diametrically placed positions. The operable elements 143'''a, 143'''b deflects the first gear 144 causing the first gear 144 to assume an oval shape, in an axial cross-section. The operable elements 143'''a, 143'''b maintains the first gear 144 deflected, such that the teeth of the first gear 144 are interengaged with the teeth of a second gear 145 in two angularly spaced, diametrically placed positions. The second gear 145 has a greater number of teeth than the first gear 144, on the inside surface thereof, and the operation of the operable element 143'''a, 143'''b thus advances the interengaged positions and thereby causes relative rotation between the first gear 144 and the second gear 145. The gear system further comprises a third gear 146 having an inside comprising the same amount of teeth as the outside of the first gear 144. The teeth of the third gear 146 are adapted to interengage with the teeth of the first gear 144 such that the third gear 146 rotates in relation to the second gear 145, along with the interengaged positions. The third gear 146 is in connection with a force output 149 of the gear system 140 by means of a radially extending connecting structure 147 for transferring force from the third gear 146 to the force output 149.

The force output 149 is, in the embodiment described in FIG. 19a, a hollow shaft equipped with inner threads (not shown) adapted to engage outer threads of a threaded member 441a, such that the interaction between the hollow shaft 149 and the threaded member 441 transforms the radially rotating force generated by the operation of the gear system 140, to a linear force. The threaded member 441 is connected to a radially extending engaging member 444 (such as also described with reference to FIG. 3) adapted to engage the first reservoir 160a containing a hydraulic fluid. The threaded member is further connected to a shaft portion 441b which in turn is connected to a second radially extending member 444 adapted to engage the second reservoir 160b containing a hydraulic fluid. The first and second fluid reservoirs 160a, 160b are torus shaped and in fluid connection with the first and second fluid conduits 162', 162" connecting the reservoirs 160a, 160b to the restricting elements of the implantable restriction device. The torus shaped reservoirs 160a, 160b may be made from a material which is elastic to return to its torus shape when the pressure from the radially extending engaging members 444 is released, and/or the reservoirs 160a, 160b may be fixated to the radially extending engaging members 444 such that the reservoirs are forced to expand when the radially extending engaging members 444 are moved in the expanding direction of the reservoirs 160a, 160b.

In operation, the control system 195 controls the electrical motor (by energizing the coils 132) such that the force output in form of the hollow shaft 149 rotates and causes linear movement of the threaded member 441a, which, when the electrical motor is operated in a first direction causes compression of the first reservoir 160a pressing fluid from the first reservoir via the first fluid conduit 162' to the first restriction element (not shown) such that a first portion of a luminary organ is constricted. As the threaded member 441a is connected to the shaft 441b connected to the second radially extending engaging member 444 engaging the second fluid reservoir 160b, the second fluid reservoir 160b is expanded simultaneously as the first fluid reservoir 160a is compressed. The expansion of the second fluid reservoir 160b cause the fluid to return to the second fluid reservoir from the second restriction element (not shown) via the second fluid conduit 162", releasing the constriction of the second portion of the luminary organ of the patient. When the control system 195 decides (based on for example a lapsed time or an input form a sensor or a person) that the restriction device should switch restricted portion of the luminary organ, the control system controls the electrical motor such that rotation in the opposite direction is created such that the force output in form of the hollow shaft 149 rotates and causes linear movement of the threaded member 441a in the opposite direction, which via the connection with the shaft 441b causes compression of the second reservoir 160b pressing fluid from the second reservoir 160b via the second fluid conduit 162" to the second restriction element (not shown) such that a second portion of a luminary organ is constricted. The first fluid reservoir 160a is expanded simultaneously as the second fluid reservoir 160b is compressed. The expansion of the first fluid reservoir 160a cause the fluid to return to the first fluid reservoir 160a from the first restriction element (not shown) via the first fluid conduit 162", releasing the constriction of the first portion of the luminary organ of the patient.

The control unit comprises a seat portion 445 functioning as an anvil in relation to the compression of the reservoir 160, and at the same time functioning as an enclosure, at least partially enclosing the gear system and the electrical motor. The seat portion 445 connects to a pleated bellows portion 442 of the enclosure adapted to enclose the force output 149 and the threaded member 441, such that the threaded member 441 and force output 149 is sealed from bodily fluids. The connection of the seat portion 445 with the portion of the enclosure 442 enclosing the force output 149 and the threaded member 441 removes the need for a seal between the seat portion 445 and the force output 149 which facilitates the operation of gear system 140 and makes it possible for the gear system 140 to be hermetically enclosed. The pleated portion 442 is adapted to allow in-growth of fibrotic tissue without the mobility of the pleated portion 442 being affected. Further, in the embodiment of FIG. 19a, the coils 132 are placed and sealed in an individual coil enclosure 131, such that the coils 132 are further isolated from the bodily fluids of the patient and/or from lubricating fluids used in the gear system and/or from the hydraulic fluids.

Figure 19B:
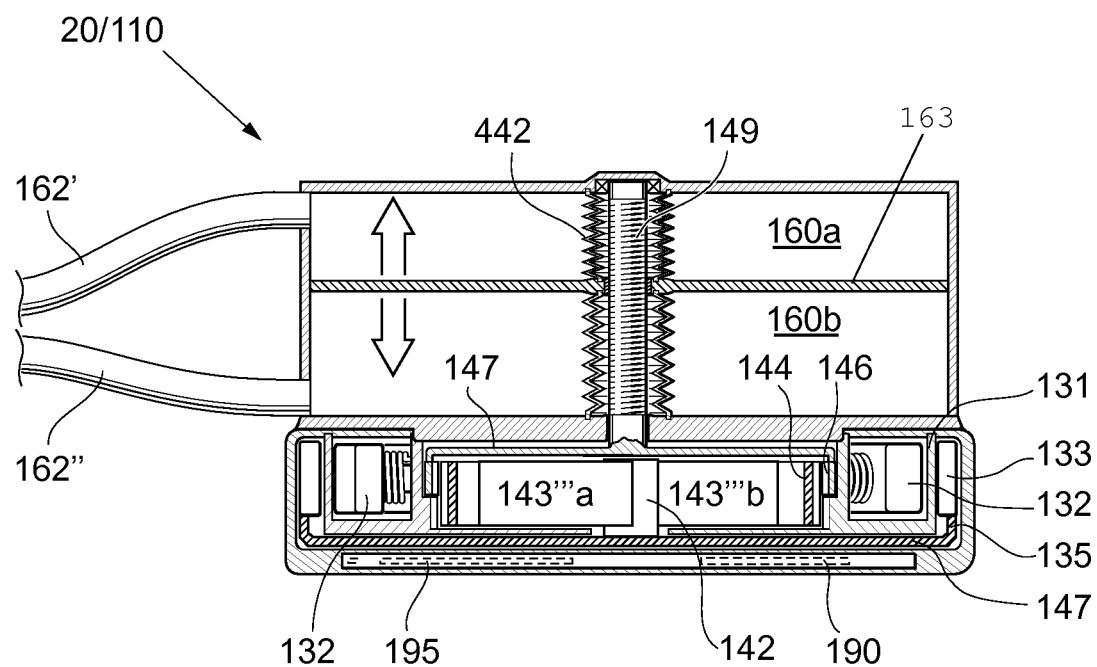
FIG. 19b shows a sectional side-view of an embodiment of a control unit for use in the implantable hydraulic restriction device.

FIG. 19b shows an embodiment functionally equivalent to the embodiment shown in FIG. 19a. The difference is that the implantable first and second fluid reservoirs 160a, 160b are divided a common moveable wall 163 for changing the volume of the implantable fluid reservoirs 160a, 160b and thereby increasing fluid in the first fluid reservoir 160a simultaneously with decreasing fluid in the second fluid reservoir 160b and vice versa. The force output 149 of the operation device is threaded and engages a correspondingly threaded portion of the movable wall 163 such that the rotating force created by the operation device is transferred to a linear force moving the movable wall 163. The threaded force output 149 is enclosed by pleated bellows portions 442 both above and below the movable wall 163 such that the threaded force output 149 (and the rest of the operation device) is protected from the fluids in the reservoirs 160a, 160b.

An embodiment of a gear system which may be used in any of the operation devices will now be described in further detail with reference to FIGS. 20a-21d.

Figure 20A:
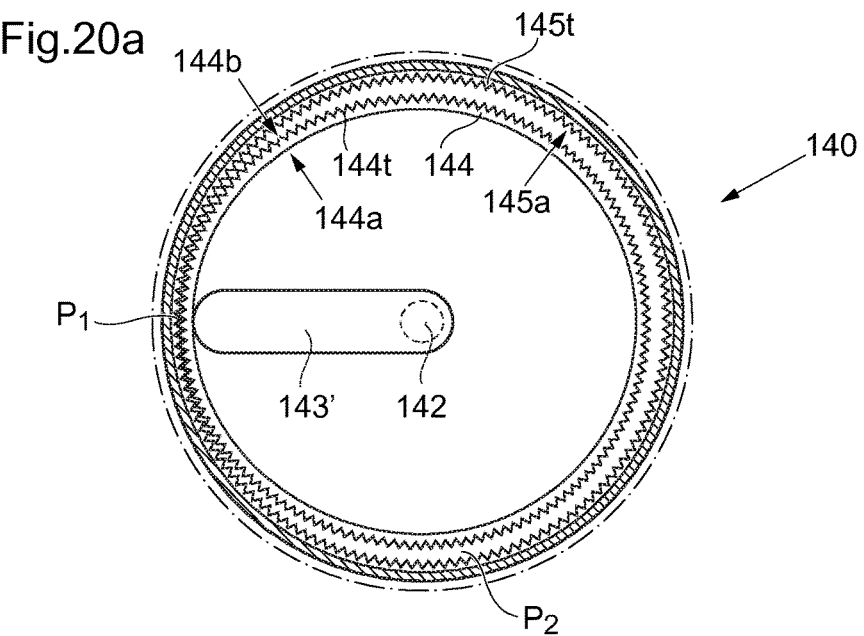
FIG. 20a shows a top-view of a gear system for use in an operation device.

FIG. 20a shows an embodiment of an implantable gear system 140 for operation in an operation device. The gear system 140 is adapted to receive mechanical work having a first force and first velocity, and output mechanical work having a second, different force and a second different velocity. The gear system 140 comprises a force input 142 connected to an operable element 143' adapted to engage a first gear 144 having the shape of a hollow cylinder, comprising a first number of teeth 144t, for example 160, on the peripheral outside thereof, and a second gear 145 having the shape of a hollow cylinder, comprising a greater number of teeth 145t than the first gear, for example 162, on the inside surface thereof. The operable element 143' is adapted to engage the inside 144a of the first gear 144, such that the outside 144b of the first gear 144 is pressed against the inside 145a of the second gear 145 such that the teeth 144t of the first gear 144 are interengaged with the teeth 145t of the second gear 145 in position $P_1$ interspaced by positions (for example the position $P_2$) at which the teeth are not interengaged. The operation of the operable element 143' advances the position $P_1$ and thereby causes relative rotation between the first gear 144 and the second gear 145. In the embodiment shown in FIG. 20a, the second gear 145 comprises two more teeth 145t than the first gear 144, resulting in the first gear 144 rotating 2/160 or 1/80 of a revolution for each revolution that the operable element 143' performs, which results in a transmission of 80 times, i.e. the force output (149 of FIG. 2b) provides a force with 1/80 of the velocity and 80 times the force, thus increasing the force which can be exerted by for example an electrical motor, 80 times. In the embodiment shown in FIG. 20a the operable element slides radially against the inner surface of the first gear 144. For reducing the friction a lubricating fluid may be present in the gear system, it is further conceivable that the operable element 143' or the surface against which the operable implant 143' slides may comprise a self lubricating material, such as Graphalloy, Nyliol or PTFE.

Figure 20B:
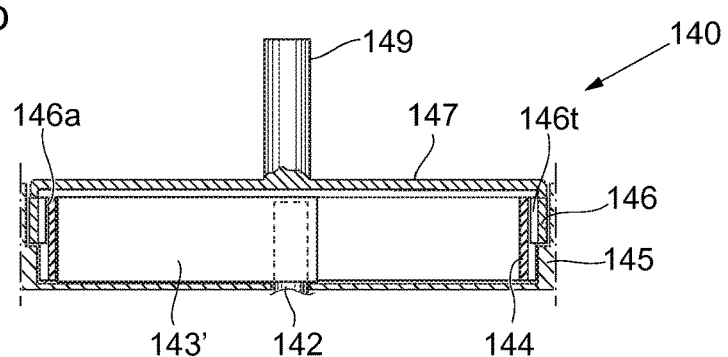
FIG. 20b shows a sectional side-view of the gear system shown in FIG. 20a, FIG. 20c shows a top-view of a gear system for use in an operation device.

FIG. 20b shows the gear system 140 in a sectional side view, in an embodiment in which the gear system 140 comprises a third gear 146 having an inside 146a comprising the same amount of teeth 146t as the outside 144b of the first gear 144. The teeth 146t of the third gear 146 are adapted to interengage with the teeth of the first gear 144 such that the third gear 146 rotates in relation to the second gear 145, along with the interengaged position ($P_1$ of FIG. 20a). The third gear 146 is in connection with a force output 149 of the gear system 140 by means of a radially extending connecting structure 147 for transferring force from the third gear 146 to the force output 149.

Figure 20C:
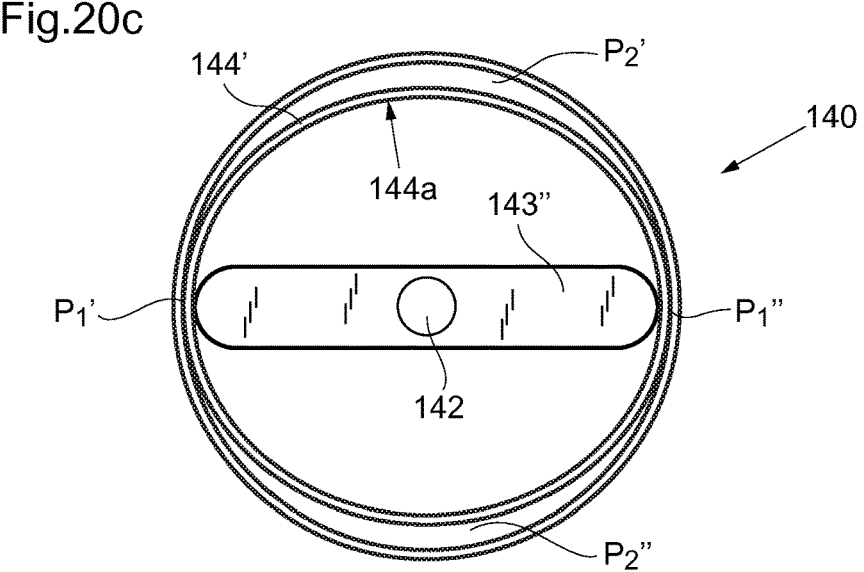

FIG. 20c shows an alternative embodiment of the medical device, wherein the operable element 143" is adapted to engage the inside 144a of the first gear 144 in two diametrically placed positions. The operable element 143" deflects the first gear 144 causing the first gear 144 to assume an oval shape, in an axial cross-section. The operable element 143" is adapted to maintain the first gear 144' deflected, such that the teeth of the first gear 144 are interengaged with the teeth of the second gear 145 in two angularly spaced, diametrically placed, positions $P_1'$ and $P_1''$. The two positions $P_1'$ and $P_1''$ are interspaced by positions at which the teeth are not interengaged, for example positions $P_2'$ and $P_2''$. In the embodiment of FIG. 20c, when the teeth of the first and second gears 144, 145 are interengaged in two positions, for the first gear 144 to be equally deflected, thus forming an oval shape, the difference in the number of teeth between the first gear 144 and the second gear 145 must be possible to divide by 2, such that the differing number of gears can be evenly distributed amongst the two areas between the first and second gears 144, 145 with positions in which the teeth of the first and second gears 144, 145 are not interengaged. Mathematically this can be expressed as if the first gear has x teeth, the second gear must have x+n*2 gears and the transmission provided by the gear system 140 is then calculated as: transmission=x/(x+n*2). In alternative embodiments (not shown) the operable element may be an operable element adapted to deflect the first gear 144 such that the first and second gears 144, 145 are interengaged at three, four or more positions, for the purpose of creating an even deflection of the first gear 144, the difference in the number of teeth between the first gear 144 and the second gear 145 must correspond to the number of contacting portions. In a more general mathematical expression, the relation can be expressed such that the second gear must have x+n*m number of teeth, where n is a constant selected based on the desired transmission and m is the number of positions in which the teeth of the first and second gears are interengaged.

Figure 21A:
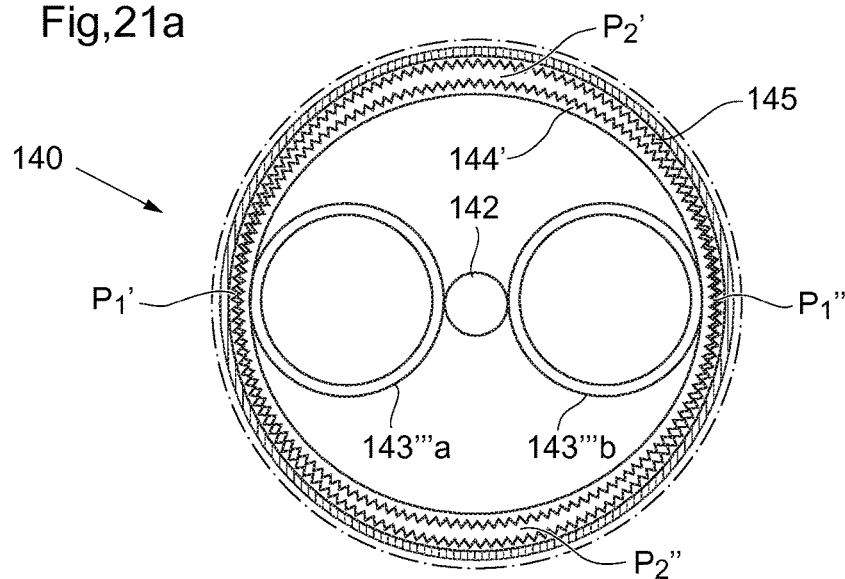
FIG. 21a shows a top-view of a gear system for use in an operation device.

FIG. 21a shows an embodiment in which the operable element comprises a planet gear in which the force input 142 comprises a central gear in connection with a first and second planet gear 143'''a, 143'''b, which in turn deflects the first gear 144 such that the teeth of the first gear 144 interengages the teeth of the second gear 145 in a first and second position P₁', P₁'. Analogously to what was previously described with reference to FIG. 20c, for the first gear 144' to be equally deflected, thus forming an oval shape, the difference in the number of teeth between the first gear 144 and the second gear 145 must be possible to divide by 2, such that the differing number of gears can be evenly distributed amongst the two areas between the first and second gears 144, 145 with positions in which the teeth of the first and second gears 144, 145 are not interengaged.

The planetary gear of FIG. 21*a* further increases the transmission of the gear system with the transmission resulting from the difference in the number of teeth between the central gear 142 and the planetary gears 143'''*a*, 143'''*b*, i.e. the total transmission of the gear system 140 equals the transmission provided by the planetary gear plus the transmission provided by the difference in number of teeth between the first gear 144 and the second gear 145.

Figure 21B:
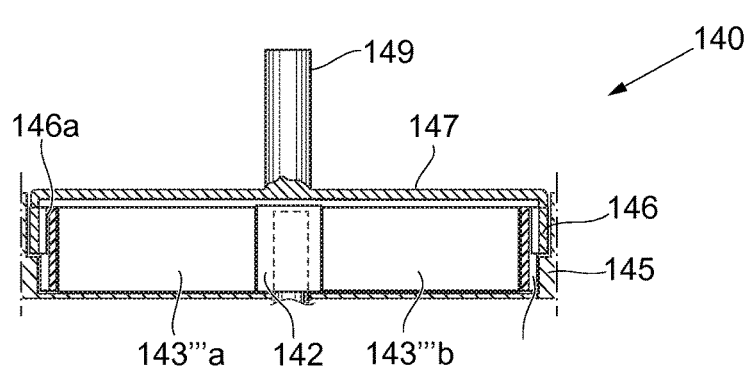
FIG. 21b shows a sectional side-view of the gear system shown in FIG. 20a, FIG. 21c shows a top-view of a gear system for use in an operation device.

FIG. 21*b* shows the gear system 140 in a sectional side view. In the embodiment shown in FIG. 21*b*, the gear system 140 also comprises a third gear 146 analogously to the third gear described with reference to FIG. 20*b*, such that the third gear 146 rotates along with the first gear and the interengaged positions P1', P1''. The third gear 146 is in connection with a force output 149 of the gear system 140 by means of a radially extending connecting structure 147 for transferring force from the third gear 146 to the force output 149.

Figure 21C:
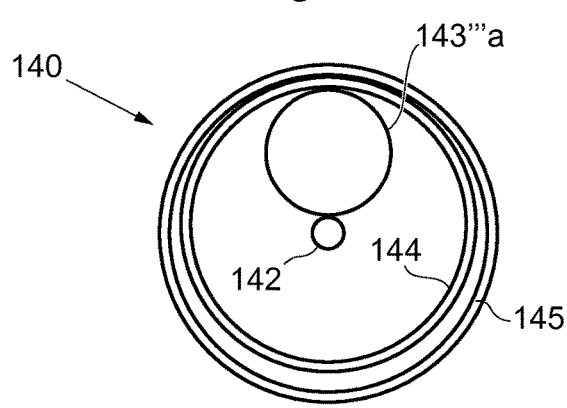
FIG. 21d shows a top-view of a gear system for use in an operation device.

FIG. 21*c* shows an alternative embodiment of the planetary gear, in which the planetary gear only comprises one planet gear 143'''*a* in connection with the central gear 142. The embodiment functions similarly to the embodiment described with reference to FIG. 20*a*, the difference being that additional transmission is provided by the planetary gear.

Figure 21D:
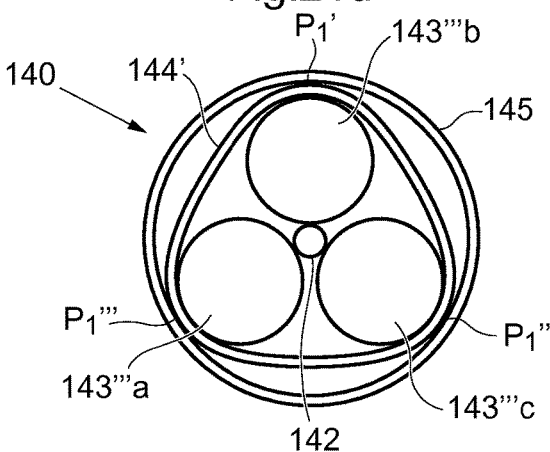

FIG. 21*d* shows an embodiment in which the planetary gear comprises three planet gears 143'''*a*, 143'''*b*, 143'''*c*, each deflecting the first gear 144', such that the first gear 144 is pressed against the second gear 145 in three angularly spaced (substantially with 120° between each) contacting positions P₁', P₁'', P₁'''. Analogy to the other embodiments described, the difference in the number of teeth between the first gear 144 and the second gear 145 must correspond to the number of contacting portions, i.e. in the embodiment shown in FIG. 21*d*, the difference must be possible to divide by three for the first gear 144 to be evenly deflected.

In alternative embodiments, the gears of the planetary gears in any of the embodiments described with reference to FIGS. 21*a*-21*d* are gears without teeth and thus only uses friction to interengage each other. The central gear is thus connected to, and propels, the planet gears by means of a friction based connection.

The gear system 140 of any of the embodiment in FIGS. 20*a*-21*d* could for example be made of a metallic material, plastic material or ceramic material. In one embodiment, the gear system is made from non metallic and/or non-magnetic material, such that the gear system does not affect the energy transfer to an implantable energy receiver. The gear system may be lubricated with a biocompatible lubricant, such as hyaluronic acid, and may, for that purpose, be placed inside a reservoir adapted to hold a hydraulic fluid, which also may serve as a lubricant. The gear system may be encapsulated by an enclosure for preventing bodily fluids from affecting the gear system and/or the in-growth of human tissue in the gear system and/or the leakage of hydraulic and/or lubricating fluids. The enclosure may be a non-metallic and/or non-magnetic enclosure, such that the material of the enclosure does not affect the ability of transferring wireless energy to a wireless energy receiver of the operable implant. The gear system may be encapsulated separately, or may be encapsulated along with an electrical motor of the operation device, or additional components of the operation device.

FIG. 22 shows an embodiment of a control unit 20 with an operation device 110 comprising a hydraulic pump in the form of a single reservoir 160 connected to a fluid conduit 162. The control unit may for example be used together with a valve member, such as for example described with reference to FIG. 3. The operation device 110 of FIG. 22 comprises an implantable electrical motor comprising coils 132 and magnets 133. Energizing of the coils 132 generates a magnetic field by the electrical current in the coil winding 132' and the coil core 132'', magnetically connecting with the magnets 133. The magnets 133 are fixated to a rotatable structure 135, such that sequential energizing of the coils 132 propels the magnets 133 and causes the rotatable structure 135 to rotate. The magnetic connection between the coils 132 and the magnets 133 is positioned in the periphery of the operation device 110 such that the generated torque should be as large as possible. The rotatable structure 135 comprises a radially extending portion 147 transferring the force generated by the coils 132 and magnets 133 in the periphery of the operation device 110 to the force input 142 of the gear system in connection with the operable elements 143'''*a*, 143'''*b*. The operable elements engages and deflects the first gear 144 of the gear system 140 such that the outside of the first gear 144 is pressed against the inside of the second gear 145 such that the teeth of the first gear 144 are interengaged with the teeth of the second gear 145 in two positions interspaced by positions at which the teeth are not interengaged. The second gear 145 has a greater number of teeth than the first gear 144, on the inside surface thereof, and the operation of the operable element 143'''*a*, 143'''*b* thus advances the interengaged positions and thereby causes relative rotation between the first gear 144 and the second gear 145.

The gear system further comprises a third gear 146 having the shape of a hollow cylinder. The inside of the third gear 146 comprises the same amount of teeth as the outside of the first gear 144, and the teeth of the third gear 146 is adapted to interengage the teeth of the first gear 144 such that the third gear 146 rotates in relation to the second gear 145, along with the at least one interengaged position. The third gear 146 is connected to a radially extending portion 147 connecting the third gear 146 and the centrally placed force output 149 of the gear system.

Both the first 144, second 145 and third 146 gears have smaller diameters than the portion of the rotatable structure 135 at which the magnets 133 are fixated, and smaller diameters than the portion of the enclosure 111*c* fixating the coils 133. The gear system can thus be placed inside of the electrical motor, such that the coils 132 and magnets 133 axially overlaps the gear system. The electrical motor and gear system being placed in the same axial plane makes it possible to package the operation device 110 in a thin enclosure 111, which for example makes the operation device 110 suitable for subcutaneous implantation.

The embodiment of the operation device described with reference to FIG. 22 comprises a threaded member in the form of a worm shaft 441' having a first spiral groove in a first direction and a second spiral groove in a second direction. The worm shaft 441' is engaged by an operable portion 446 connected to a radially extending engaging member 444 in turn adapted to compress the reservoir 160. The rotation of the worm shaft 441' causes reciprocation of the operable portion 446 in the spiral grooves, by the operable portion 446 switching from engaging the first spiral groove, to the operable portion 446 engaging the second spiral groove at the end portions of the worm shaft 441'. The worm shaft 441' makes it possible to compress and expand the reservoir 160 with the electrical motor always rotating in the same direction, which facilitates the control and makes it possible to optimize the motor, seals and bearings for a particular rotational direction.

In the operation device 110 FIG. 22, the coils 132 are placed in a sealed space further comprising a energizing unit in the form of a battery 190, adapted to power the electrical motor, and a control system 195 adapted to control the electrical motor and/or additional operable elements of the operable implant. The battery 190 and/or control system 195 is in connection with a lead 192 connecting the battery 190 and/or control system 195 to a wireless energy receiver and/or a wireless communication unit and/or an additional battery 190 for supplying the operation device with additional energy. In alternative embodiments, where the electrical motor is powered directly from a wireless energy receiver, the battery 190 is only adapted to power the control system 195.

FIG. 23 shows a control unit 20 and operation device 110 similar to the control unit 20 and operation device 110 shown with reference to FIG. 22, the difference being that in the operation device in FIG. 23, the magnets 133 are fixated to a rotatable structure 135 comprising a radially extending portion 147 adapted to transfer the force from the periphery of the rotatable structure 135 to the center of the rotatable structure 135 below the electrical motor and the gear system. The radially extending portion 147 transferring force to the force input 142 of the gear system, which in turn engages the operable elements 143'''a, 143'''b.

In the embodiment of FIG. 23, the coils 132 are placed and sealed in an individual coil enclosure 131, such that the coils 132 are further isolated from the bodily fluids of the patient and/or from lubricating fluids used in the gear system and/or from hydraulic fluids adapted to transfer force from the reservoir 160 to a hydraulically operable body engaging portion, through the fluid conduit 162.

FIG. 24 shows yet an alternative embodiment of a control unit 20 and operation device 110 similar to the control unit 20 and operation device 110 shown with reference to FIGS. 22 and 23. In the embodiment shown with reference to FIG. 24, the rotatable structure 135 comprising the magnets 133 is adapted to be propelled by coils 132 mounted to a portion 111c of the enclosure 111 having a peripheral diameter larger than the diameter of the rotatable structure 135 where the magnets 133 are mounted. The coils 132 are thus placed radially outside the magnets 133 and are sealed from the rest of the operation device 110 and from the bodily fluids of the patient by means of a coil enclosure 131. The rotatable structure 135 is connected to a force input 142 in the center of the rotatable structure, which in turn is adapted to engage the operable elements 143'''a, 143'''b of the gear system (as described in further detail in other embodiments herein). The embodiment shown in FIG. 24 places all rotating parts of the operation device 110 centrally in the operation device 110 which further insulates the rotating parts of the operation device 110, such that noise created by the moving parts are less likely to propagate through the enclosure 111 of the operation device 110 and the body of the patient.

FIG. 25 shows yet an alternative embodiment of a control unit 20 and operation device 110 similar to the control unit 20 and operation device 110 shown with reference to FIGS. 22, 23 and 24. In FIG. 25 the magnets 133 are integrated in the operable elements 143'''a, 143'''b of the operation device 110. The operable elements 143'''a, 143'''b are rotatably connected to a connecting structure 143c and engages and deflects the first gear 144 of the gear system as the magnetic attraction force generated by the coils sequentially attracts the magnets 133 propelling the operable elements 143'''a, 143'''b. The portion of the operable elements 143'''a, 143'''b to which the magnets 133 are connected have a larger diameter than the portion of the operable elements 143'''a, 143'''b engaging the first gear 144 of the gear system, such that the magnets 133 can be placed in close connection with the coils 132. The distance between the coils 132 and the magnets 133 could for example be as little as one of 50 μm, 100 μm, 200 μm, 400 μm, 600 μm, 800 μm, 1 mm, 2 mm, 3 mm, or 5 mm, depending on the overall dimensions of the operation device 110 and the magnetic force created by the coils 132.

Figure 26:
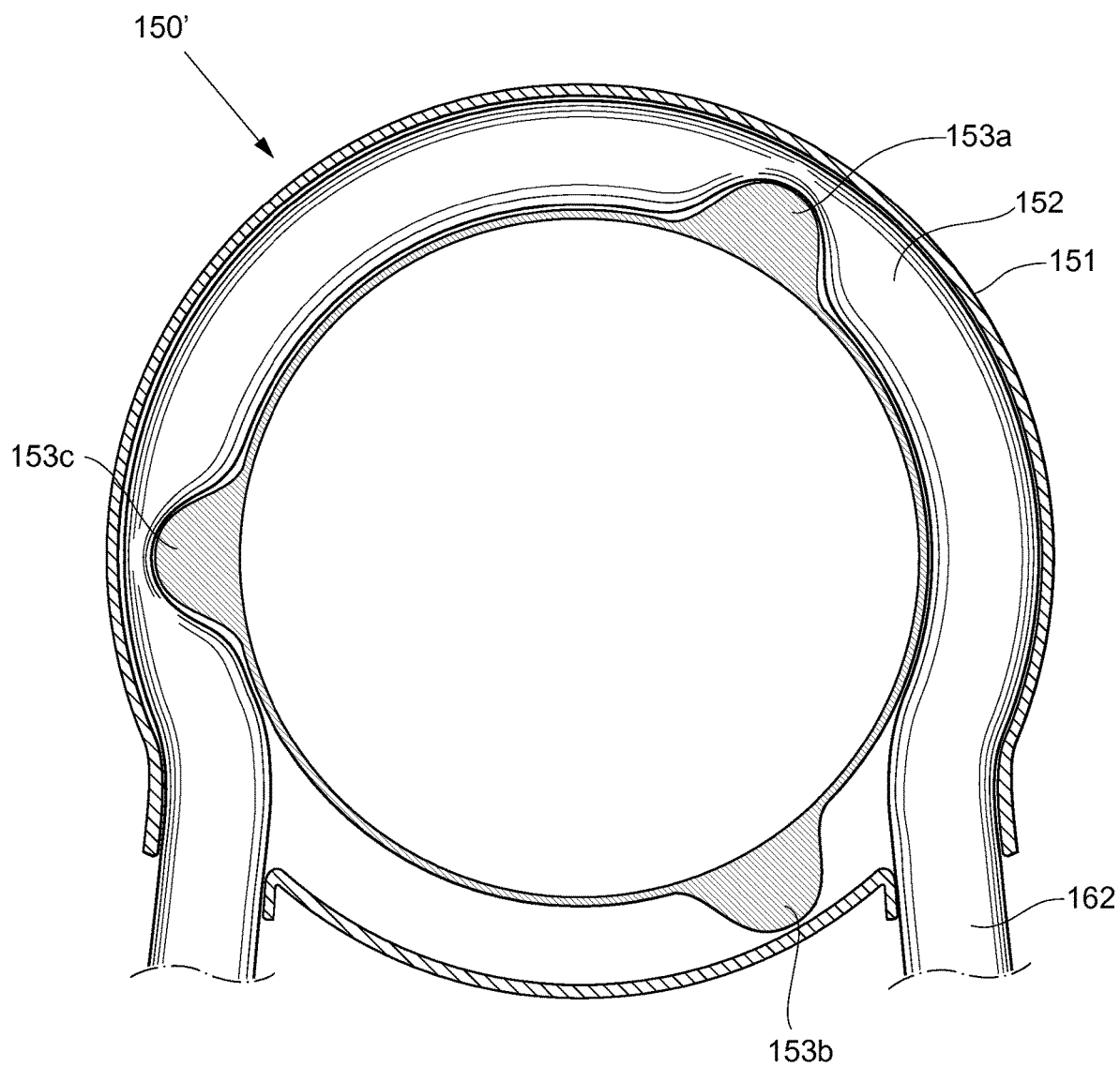
FIG. 26 shows a top-view of a peristaltic pump for use in the operation device of any of the embodiments herein.
Figure 27A:
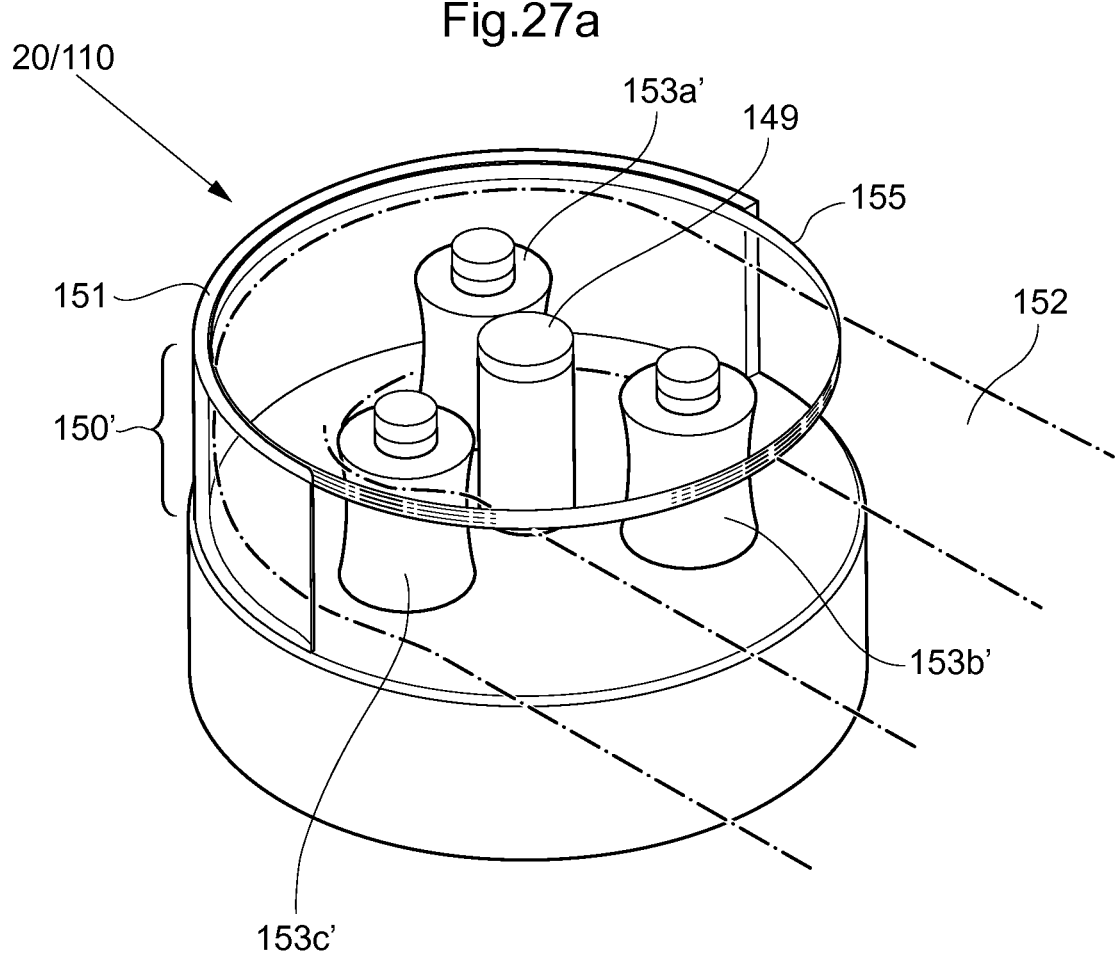
FIG. 27a shows a control unit for use in a hydraulic restriction device comprising a peristaltic pump, in a perspective view.
Figure 27B:
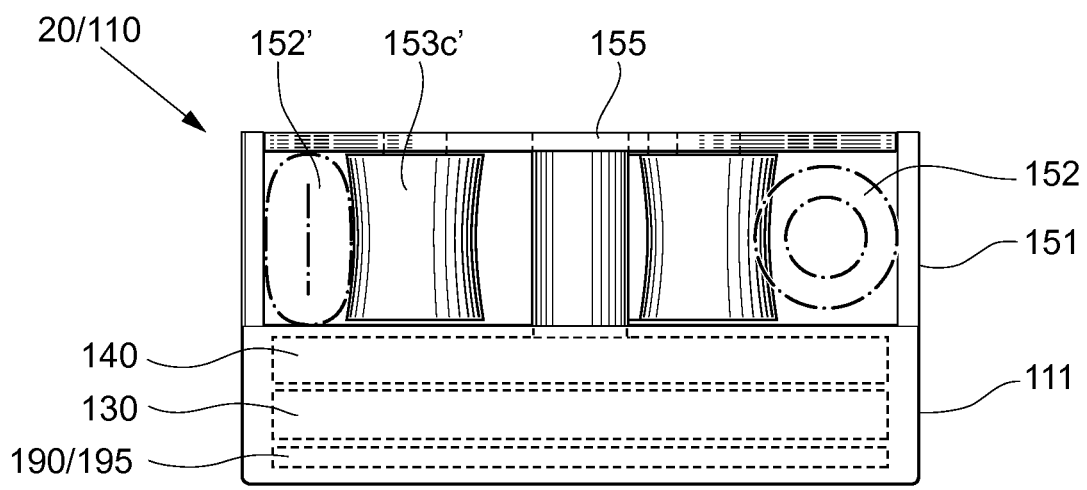
FIG. 27b shows a sectional side view of the control unit of FIG. 27a, FIG. 28 shows an exploded view of an embodiment of an operation device.

FIG. 26 shows a more detailed view of an implantable peristaltic pump 150' adapted to pump and thus transport a hydraulic fluid to a hydraulically restriction element (not shown). The peristaltic pump 150' could be adapted to be connected to the force output of an electrical motor and/or gear system, such as any of the motors and/or gear systems disclosed herein. The implantable peristaltic pump 150' comprises a deflectable hollow member 152 for fluid transportation, in form of a tubing made from a resilient material, such as an elastomeric polymer material, such as silicone, Parylene® coated silicone, NBR, Hypalon, Viton, PVC, EPDM, Polyurethane or Natural Rubber. The deflectable hollow member 152 is adapted to be deflected by an operable compression member 153a-153c or wiper, adapted to engage and compress the hollow member 152, and thus transport the hydraulic fluid. The compression members 153a-153c, are propelled by the motor/gear system connection (not shown). The hollow member 152 is placed inside a peristaltic pump housing 151, such that the hollow member 152 is compressed between the operable compression members 153a-153c. The peristaltic pump 150' enables the hydraulic fluid to be completely separated from the bodily fluids as the hollow member 152 is integrated with the fluid conduit 162 conveying fluid to the restriction elements (not shown), such that the hydraulic fluid can be transported without the risk of leakage. In the e FIGS. 27a and 27b shows a control unit 20 comprising an operation device 110 comprising a peristaltic hydraulic pump 150' similar to the peristaltic pump 150' described with reference to FIG. 26, for use in the any of the restriction device disclosed herein. The difference between the embodiment disclosed in FIG. 26 and the embodiment of FIGS. 27a and 27b is that the operable compression members comprises rollers 153a'-153c' rotatably connected to a rotatable structure 155 propelled by a force output 149 of the gear system 140. The gear system 140 is in turn connected to an electrical motor 130 adapted to propel the gear system 140. The electrical motor 130 is in the embodiment described in FIGS. 27a and 27b energized by a battery 190 and controlled by a control system 195, both enclosed by the enclosure 111 enclosing the control unit 20.

The rollers 153a'-153c' sequentially compresses the hollow member 152 and thus transports fluid in the hollow member 152. In FIG. 27b the operation device with the peristaltic pump 150' is shown in section, such that the hollow member 152 is shown in its non-compressed state 152 and its compressed state 152', when the roller 153c' compresses the hollow member 152' against the housing 151 of the peristaltic pump 150'. The electrical motor 130 and the gear system 140 could for example be an electrical motor (130) and gear system (140) described in any of the embodiments herein. As the rollers 153a'-153c' roll against the hollow member 152 they do not wear or rupture the hollow member 152 in the same way as a wiping or sliding operable compression member risks to do, which increases the life span of the hollow member 152.

Figure 28:
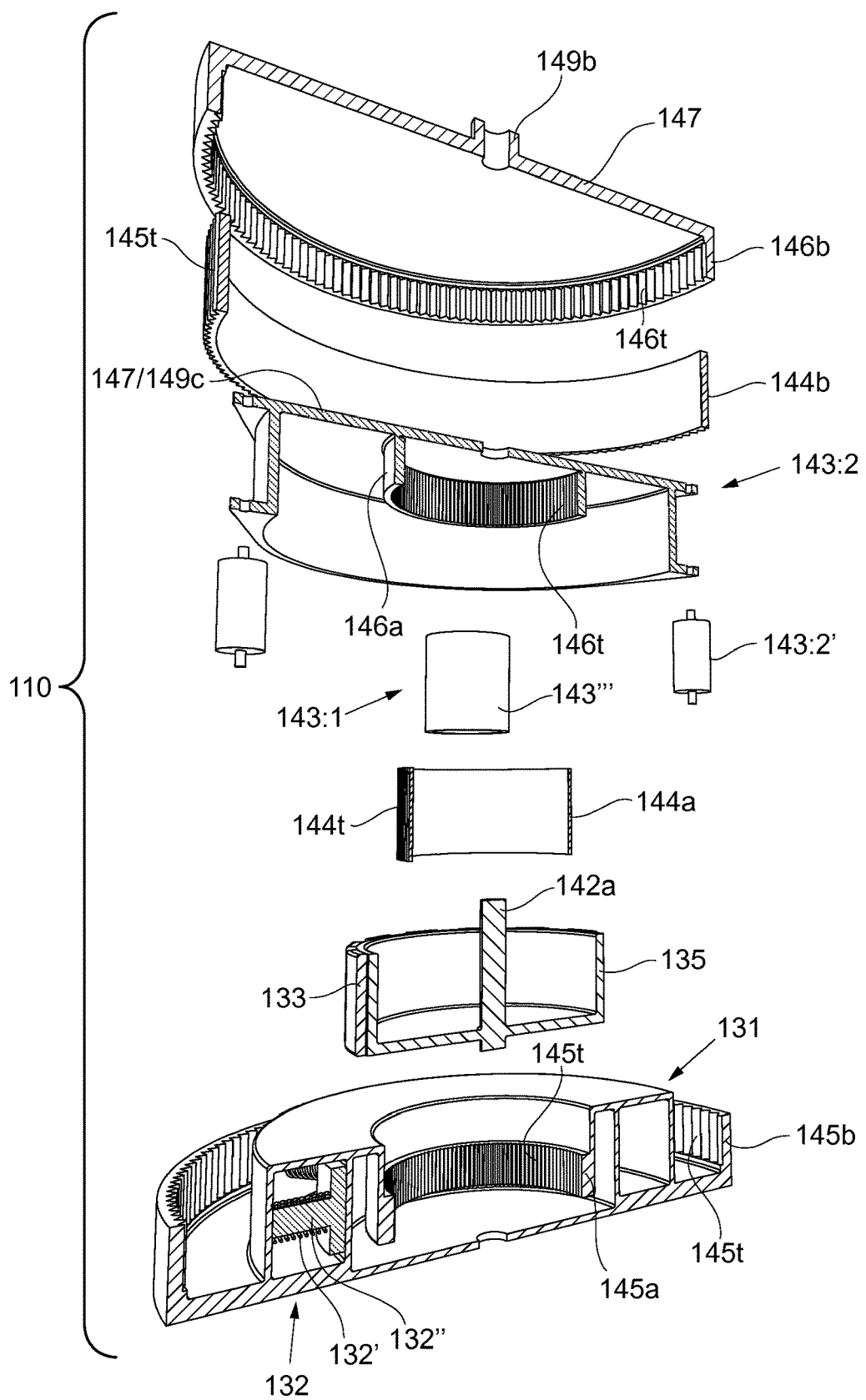

FIG. 28 shows an embodiment of an electrical motor and a first and second gear system in an exploded view. The embodiment may be integrated in the control unit in any of the embodiments herein. The lowermost piece is the static part of the operation device 110, comprising the second gear 145a of the first gear system and the second gear 145b of the second gear system 145b. The lowermost piece further comprises the coils 132 of the electrical motor, comprising the coil cores 132" and the coil windings 132', and the coil enclosures 131, which are adapted to hermetically enclose the coils 132, such that the coils 132 are sealed from bodily fluids and/or lubricants adapted to lubricate the first and/or second gear system and/or hydraulic fluids for transferring force from the operation device 110 to a hydraulically operable body engaging portion of the operable implant (further described in relation to other embodiments described herein). Above the static part 132, 145a, 145b, the rotatable structure 135 is depicted. The rotatable structure 135 comprises the magnets 133 adapted to be in magnetic connection with the coils 132, such that sequential energizing of the coils 132 propels the magnets 133 and thus the rotatable structure 135 to which the magnets 133 are fixated. The rotatable structure 145 also comprises the force input 142a to the first gear system 140a, which is adapted to propel the planetary gear 143'" being the operable element 143:1 of the first gear system 140a, by means of interengaging teeth or friction. The operable element 143'" engages and deflects the first gear 144a of the first gear system 140a such that the teeth 144t on the outside of the first gear 144a interengage the teeth 145t on the inside of the second gear 145a of the first gear system, being part of the static part. As the first gear 144a of the first gear system comprises fewer teeth 144t than second gear 145b of the second gear system, the interengaging position between the first and second gears 144a, 145a are advanced, and as the third gear 146a of the first gear system comprises the same amount of teeth 146t as the first gear 144a, the third gear 146a moves along with the advancing positions. The third gear 146a of the first gear system is an integrated part of the operable element 143:2 of the second gear system, thus also comprising the force output 149b of the second gear system, and a radially extending structure 147 connecting the third gear 146a of the first gear system and the rolling operable elements 143:2' of the operable element 143:2.

The rolling operable elements 143:2' of the operable element 143:2 of the second gear system engages and deflects the first gear 144b of the second gear system, such that the second gear system propels the third gear 146b of the second gear system analogously to the first gear system. The third gear 146b of the second gear system is integrated in a structure (the uppermost structure depicted) further comprising a radially extending element 147 connecting the third gear 146b the force output 149b of the second gear system (and of the operation device), such that the mechanical work generated by the electrical motor 132, 133 can be outputted as rotational force through the force output 149b.

In the embodiment shown in FIG. 28 the first and second gear systems have the same transmission. However, it is conceivable that the second gear system have a higher transmission than the first gear system, i.e. that the gears of the second gear system has more teeth than the gears of the first gear system, while the difference between the number of teeth of the first and second gears 144a, 144b, 145a, 145b of the first and second gear systems are the same. For example, the first gear 144a of the first gear system having 98 teeth, the second gear 145a of the first gear system having 100 teeth, the first gear 144b of the second gear system having 198 teeth and the second gear 144b of the second gear system having 200 teeth, resulting in the first gear system having a transmission of 1:50 (plus the transmission of the planetary gear system provided by the operable element) and the second gear system having a transmission of 1:100. In some applications it may be advantageous that the gears of the second gear system has the same number of teeth as the gears of the first gear system (thus being larger), as the gears of the second gear system is required to transfer higher force with lower velocity.

FIG. 29 shows an alternative embodiment of the operation device 110 similar to the operation device described with reference to FIG. 28. The difference being the first gear system 140a is the gear system placed in the periphery, while the second gear system 140b is the gear system placed centrally. The coils 132 in the embodiment shown in FIG. 29 are placed inside the rotatable structure 135 comprising the magnets 133. The rotatable structure 135 is in the embodiment shown in FIG. 29 integrated with the operable element 143:1 of the first gear system 140a. The operable element 143:1, in the embodiment shown in FIG. 29 comprises a rolling operable element 143:1' adapted to engage the inside of the first gear 144a for deflecting the first gear 144a. The interengagement of the first gear 144a and the third gear 146a of the first gear system 140a propels the third gear 146a of the first gear system 140a which is in connection with the force input 142b adapted to propel the operable elements 143", in turn deflecting the first gear 144b of the second gear system 140b, for propelling the third gear 146b of the second gear system 140b, serving as force output for the operation device 110. The structure 131, 145b enclosing the coils 132 constitutes the static part of the operation device 110 and is directly or indirectly connected to the second gear 145a of the first gear system 140a such that the second gear 145a of the first gear system 140a is static along with the second gear 145b of the second gear system 140b and the coil enclosure 131.

FIG. 30a shows an embodiment of an operation device 110 which may be integrated in the control unit of any of the embodiments herein. The operation device 110 of the embodiment of FIGS. 30a and 30b comprises an operable reservoir 160 adapted to contain a hydraulic fluid. The electrical motor and double gear system portion of the operation device is similar to what is operation device described with reference to FIGS. 28 and 29. However, the operation device of FIGS. 30a and 30b additionally comprises a circular reservoir 160 encircling the operation device 110. The circular reservoir 160 comprises a movable wall portion adapted to compress and expand the circular reservoir 160, thereby altering the volume of the reservoir 160. The third gear 146b of the second gear system, rotating along with the interengaging portions between the first and second gears 144b, 145b is connected to an operation spiral 472 adapted to engage a radially fixed corresponding operation spiral 473, such that the operation of the operation spiral 472 in relation to the radially fixed operation spiral 473 moves the radially fixed operation spiral axially, such that the reservoir 160 is compressed.

FIG. 30a shows the operation device 110 in a state in which the operation spiral 473 is aligned in relation to the corresponding radially fixated operation spiral, such that the two spirals 472, 473 match and forms a structure being as thin as possible and thus compressing the reservoir 160 minimally i.e. the thinnest portion of the operation spiral 472b engages the thickest portion of the radially fixed operation spiral 473a.

FIG. 30b shows the operation device 110 in a state in which the operation spiral 472 has performed close to a full rotation, such that the thickest portion of the operation spiral 472a engages the thickest portion of the radially fixed operation spiral 473a, such that the two spirals "mismatch" and forms a structure being as thick as possible and thus compressing the reservoir 160 maximally. One revolution of the operation spiral 472 thus alters the state of the reservoir 160 from being fully expanded to fully compressed, which enables transportation of hydraulic fluid from the reservoir to the hydraulically operable body engaging portion by the operation device 110.

The circular reservoir 160 is compressible by means of a pleated portion 443 enabling the reservoir 160 to be made from a resilient but non-elastic material, such as a non-elastomeric polymer material.

FIGS. 31a and 31b shows an embodiment of an operation device 110 similar to the embodiment of the operation device 110 shown with reference to FIGS. 30a and 30b. The electrical motor 130 portion and the gear systems 140 portions are identical. The difference in the operation device is that the third gear 146 of the second (outer) gear system is connected to radially operable operation members 482a, 482b adapted to engage two reservoirs 160a, 160b, each radially extending along substantially half the circumference of the operation device 110. The first and second radially extending reservoirs 160a, 160b comprises walls having pleated portions 442 enabling the compression of the reservoirs 160a, 160b by the radial movement of the radially operable operation members 482a, 482b. A first end 160a' of the first reservoir 160a is connected to a first radially operable operation member 482a, and a second end 160a" of the first reservoir 160a is connected to a first radially fixated member 483a. Analogously, a first end 160b' of the second reservoir 160b is connected to a second radially operable operation member 482b, and a second end 160b" of the second reservoir 160b is connected to a second radially fixated member 483b. The first and second reservoirs 160a, 160b are compressed between the radially operable operation members 482a, 482b and the radially fixated members 483a, 483b, respectively, such that the volume in the first and second reservoirs is changed. As the volume in the reservoirs decrease, the fluid contained in the reservoirs is transported from the reservoirs 160a, 160b to the body engaging portions via fluid conduits 162. The operation device of FIG. 31a is connected to a control unit 20 (such as any of the control units described herein) by means of a lead 192 adapted to transfer energy and/or information.

Figure 32:
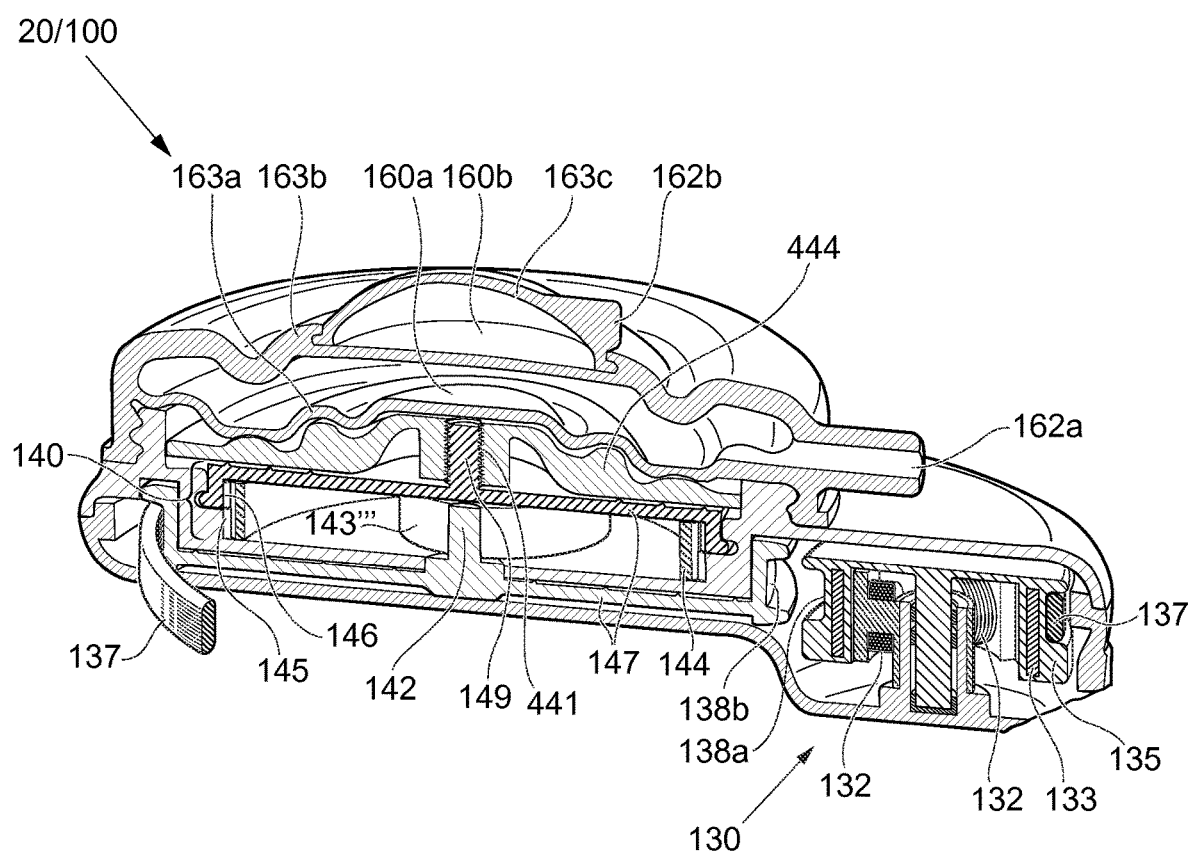
FIG. 32 shows a sectional elevated side-view of a control unit for use in an implantable hydraulic restriction device.

FIG. 32 shows a control unit 20 comprising an implantable operation device 110 for operating a body engaging portion of an operable hydraulic implant in section. The control unit may be used for implantation in any of the positions disclosed herein and may be connected the restriction elements according to any of the embodiments herein. The operation device comprises a reservoir 160a for holding a hydraulic fluid. The reservoir 160a comprises a movable wall portion 163a adapted to move to alter the volume of the reservoir 160a and thereby transport hydraulic fluid from the reservoir 160a to the body engaging portion. The operation device further comprising an operation member 444, extending radially and being connected to the movable wall portion 163a, such that operation of the operation member 444 alters the volume of the reservoir 160a. The operation device 110 further comprises a flexible enclosure 111 adapted to have its volume altered by changing the outer size and shape of the enclosure and enclose the movable wall portion 163a and the operation member 444. The movable wall portion 163a is adapted to move inside of the enclosure 111, such that the volume of the reservoir 160a can be changed by affecting the outer dimensions of the operation device 110 to a lesser extent and in the opposite direction than the change of volume of the reservoir 160a by the movement of the movable wall portion 163a inside of the enclosure 111. The reservoir 160a further comprises a manual portion (reservoir) 160b comprising a movable wall portion 163c adapted to be compressed by manual force from outside of the body of the patient, such that fluid can be transported from the reservoir 160b via a second fluid conduit 162b to the body engaging portion by means of manual force, for temporarily increasing the hydraulic pressure at the body engaging portion. The manual portion 160b could for example be used in emergencies if an implantable battery runs out of power, or if a patient would like to override an automatic system.

In further detail, the hydraulic operation 110 device shown in FIG. 32 comprises an electrical motor 130, which in the embodiment shown is an alternating current (AC) electrical motor comprising a plurality of coils 132 connected to a static structure, and a plurality of magnets 133 connected to a rotatable structure 135. The plurality of coils 132 and plurality of magnets 133 are magnetically connected such sequential energizing of the coils 132 propels the magnets 133 and thus the rotatable structure 135. The peripheral surface of the rotatable structure 135 comprises or acts like a pulley 138a engaging a belt 137, such that operation of the electrical motor 130 propels the belt 137.

The belt 137 is further connected to a second pulley 138b connected to a radially extending portion 147 connecting the pulley 138a to a force input 142 of a gear system 140, being the gear system described in several embodiments herein. The force input 142 propels the operable elements 143''', which in turn engages and deflects the first gear 144 having teeth interengaging the second gear 145 and third gear 146. The first gear 144 having less teeth than the second gear 145 creating a rotation of the interengaging positions between the first and second gears 144, 145. The third gear 146 has the same amount of teeth as the first gear 144 and thus rotates along with the interengaged positions. The third gear 146 is connected to the force output 149 of the gear system 140 by means of a radially extending portion 147. The force output 149 is a threaded shaft adapted to engage inner threads of a threaded member 441 of a radially extending operation member 444 adapted to engage a movable wall portion 163a of the reservoir 160a. The interaction between the threaded shaft 149 and the threaded member 441 transforms the radially rotating force generated by the operation of the gear system 140, to a linear, axially reciprocating force. The average thickness of the movable wall portion 163a is less than the average thickness of the movable outer wall portion 163b of the reservoir 160a. The reservoir 160a is connected to a fluid conduit 162a for transporting fluid from the fluid reservoir 160a to the body engaging portion of the hydraulically operable implant 110.

The radially extending operation member 444 presses the movable wall portion 163a upwards for compressing the fluid reservoir 160a, a vacuum is created beneath the radially extending operation member 444 which forces the outer movable wall 163b to move downwards thus compresses the reservoir 160a from the outside. The operation thus changes the external size of the operation device 110 by moving a movable wall 163a within the operation device 110.

Placed coaxially and on top of the reservoir 160a is a second manual reservoir 160b. The manual reservoir 160b is enclosed by the wall of the first reservoir 160a and an external movable wall 163c adapted to be compressed by manual operation from the outside of the body of the patient. The second manual reservoir 160b comprises a second fluid conduit 162b adapted to connect the second manual reservoir 160b to the body engaging portion, such that manual compression of the reservoir 160b transports fluid from the second manual reservoir 160b to the body engaging portion. The manual portion could for example be used in emergencies if an implantable battery runs out of power, or if a patient would like to override an automatic system.

In alternative embodiments, the implantable operation device 110 may additionally comprise an injection port for injecting hydraulic fluid into the reservoir from outside the body of the patient. The injection port may be an integrated portion of the reservoir or may be connected to the reservoir by means of a fluid conduit. The injection port may be adapted to refill or calibrate the fluid amount in the first reservoir and/or in the manual reservoir 160b.

The control unit may be implanted subcutaneously and may additionally comprise a fixation member (such as the fixations member described with reference to FIGS. 43a-43e) adapted to directly or indirectly fixate at least a portion of the implantable operation device to at least one muscular fascia and/or at least one bone fascia and/or at least one cortical bone layer and/or at least one muscular layer and/or fibrotic tissue and/or any part of the abdominal wall and/or any part of the subcutaneous space and its surroundings in the body.

In alternative embodiments, the electrical motor 130 of the operation device may be an electrical motor selected from: an alternating current (AC) electrical motor, a direct current electrical motor, a linear electrical motor, an axial electrical motor, a piezo-electric motor, a two or more phase motor, a three phase motor, a bimetal motor, and a memory metal motor.

Figure 33A:
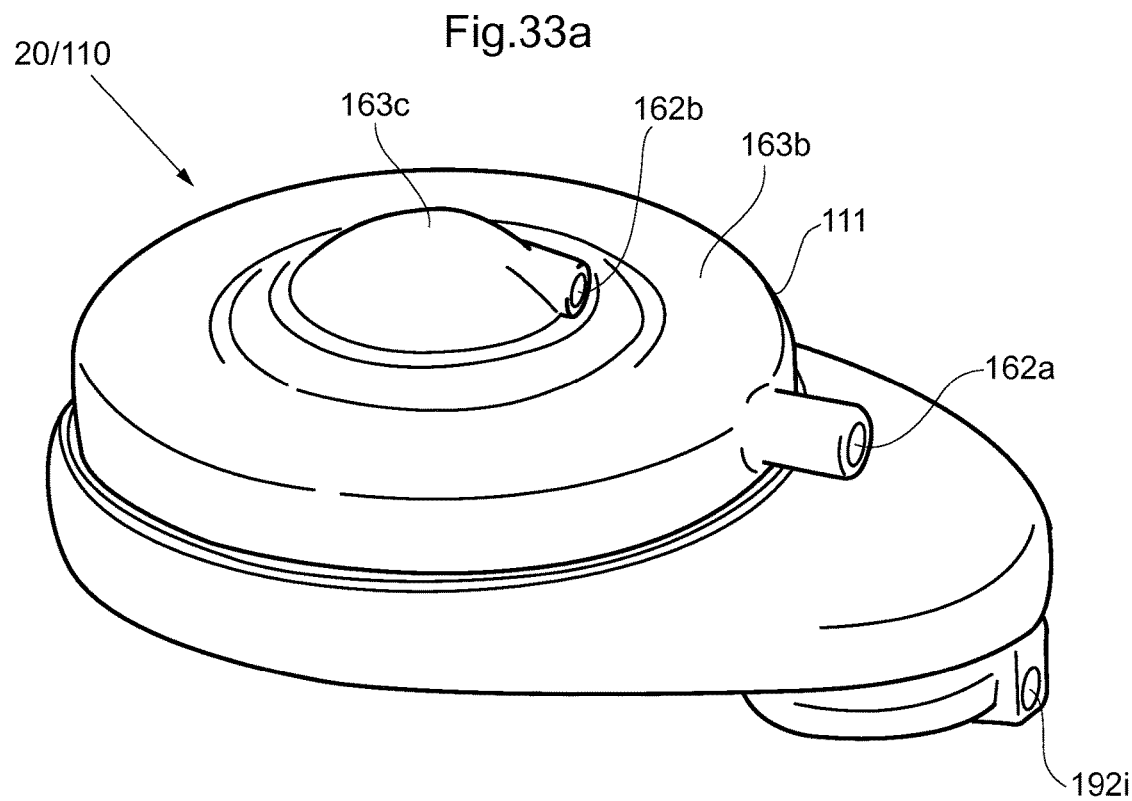
FIG. 33a shows an elevated side-view of the control unit of FIG. 32, in a first state.

FIG. 33a shows the control unit 20 shown in FIG. 32 in an external view, when the reservoirs (160a, 160b in FIG. 32) are fully expanded i.e. the movable walls 163b, 163c are not compressed. The enclosure 111 is made from a resilient polymer material, such as Parylene® coated silicone. In addition to the first and second fluid conduits 162a, 162b penetrating the enclosure 111, the enclosure 111 further comprises a lead inlet 192i for allowing an electrical lead to penetrate the enclosure 111 for powering the electrical motor (130 of FIG. 32). The electrical lead may be connected to a battery located outside of the enclosure 111, or a receiving unit for receiving wireless energy (further disclosed in other embodiments herein) located outside of the enclosure 111.

Figure 33B:
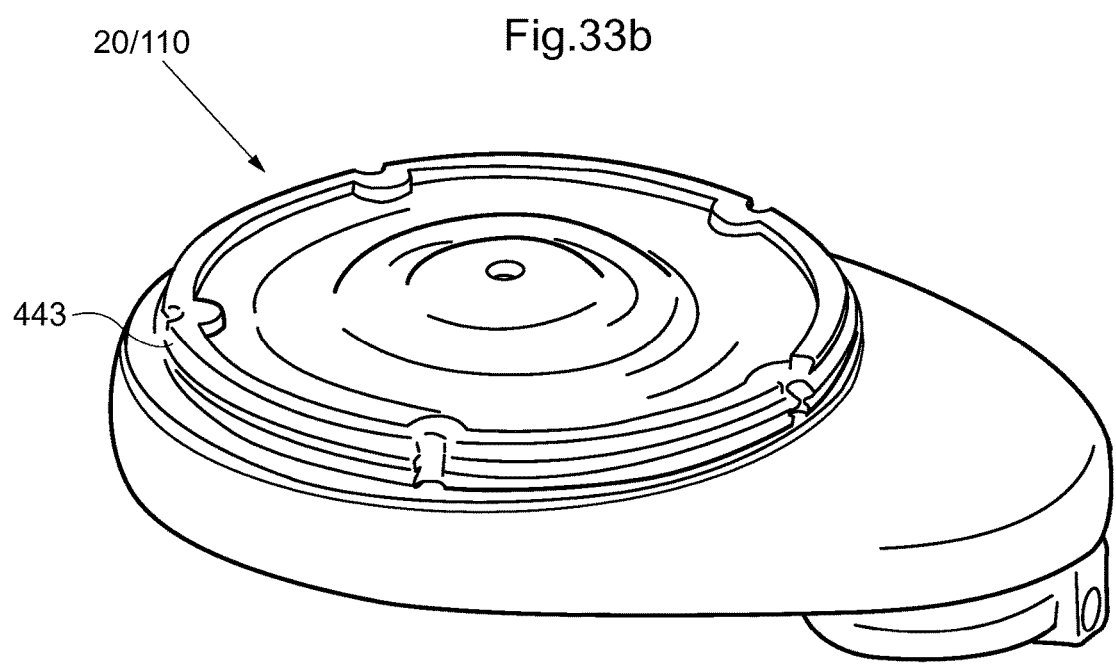
FIG. 33b shows an elevated side-view of the control unit of FIG. 32, in a second state.

FIG. 33b shows the hydraulic operation device 110 in its fully compressed state, when the volumes of both the first and second reservoirs are compressed to a minimum. In the embodiment shown, the peripheral side wall of the first reservoir (160a of FIG. 32) comprises a pleated portion 443 adapted to enable the compression of the first reservoir.

The different aspects or any part of an aspect or different embodiments or any part of an embodiment may all be combined in any possible way. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way. All examples herein should be seen as part of the general description and therefore possible to combine in any way in general terms.

NUMBERED EMBODIMENTS

In the following, exemplifying numbered embodiments are provided in groups A and B and numbered within that group. The numbered embodiments are not to be seen as limiting the scope of the invention, which is defined by the appended claims. The reference numerals in the different numbered embodiments are to be seen only as examples of elements in the appended drawings which correspond to elements described in the numbered embodiments.

Numbered Embodiment A 1-32

1. A hydraulic implantable restriction device for restricting a luminary organ of a patient, the hydraulic implantable restriction device comprising:
   a first hydraulic restriction element adapted to restrict a first portion of the luminary organ, and
   a second hydraulic restriction element adapted to restrict a second portion of the luminary organ, and
   a control unit adapted to control the first and second restriction elements for automatically switching between restricting the first and second portion of the luminary organ, for creating a less damaging restriction, wherein the control unit is adapted to automatically switch between restricting the first and second portion of the luminary organ on the basis of at least one of:
      a lapsed time being between 10 minutes and 6 months, and
      the patient using the function of the restricted luminary organ.
2. The implantable hydraulic restriction device according to embodiment 1, wherein the implantable restriction device is adapted to restrict a luminary organ of the patient selected from a list consisting of:
   an intestine of the patient,
   a blood vessel of the patient,
   the urethra of the patient,
   the vas deference of the patient,
   the stomach of the patient,
   the esophagus of the patient,
   the anal sphincter,
   the cardia sphincter,
   the urinary sphincter,
   and
   the oviducts of the patient.
3. The implantable hydraulic restriction device according to any one of embodiments 1-2, wherein the receipt of a control signal is the receipt of a control signal generated on the basis of a sensor input.
4. The implantable hydraulic restriction device according to any one of embodiments 1-3, wherein the control signal is transmitted from outside of the body of the patient.
5. The implantable hydraulic restriction device according to any one of the preceding embodiments, further comprising an implantable fluid reservoir and a first fluid conduit connecting the fluid reservoir to the first restriction element, and a second fluid conduit connecting the fluid reservoir to the second restriction element.

6. The implantable hydraulic restriction device according to embodiment 5, wherein the implantable fluid reservoir comprises at least one moveable wall portion for changing the volume of the implantable fluid reservoir and thereby moving fluid from the implantable fluid reservoir to the first and second restriction elements.
7. The implantable hydraulic restriction device according to embodiment 5, further comprising a hydraulic pump, for pumping fluid from the implantable reservoir to at least one of the first and second restriction element.
8. The implantable hydraulic restriction device according to embodiment 7, wherein the hydraulic pump is a hydraulic pump selected from:
   at least one reservoir acting as a pump by a wall of the reservoir moving,
   at least one reservoir acting as a pump by changing volume,
   at least one non-valve pump,
   at least one valve pump,
   at least one peristaltic pump,
   at least one membrane pump,
   at least one gear pump, and
   at least one bellows pump.
9. The implantable hydraulic restriction device according to any one of embodiments 5-8, further comprising an implantable valve member for directing fluid from the implantable reservoir to the first or second restriction element.
10. The implantable hydraulic restriction device according to any one of embodiments 7 and 8, further comprising at least one motor for operating at least one of:
   the movable wall portion according to embodiment 6,
   the implantable pump according to embodiment 7, and
   the implantable valve member according to embodiment 8.
11. The implantable hydraulic restriction device according to embodiment 10, wherein the motor comprises an electrical motor selected from:
   an alternating current (AC) electrical motor,
   a direct current (DC) electrical motor,
   a linear electrical motor,
   an axial electrical motor,
   a piezo-electric motor,
   a three-phase motor
   a more than one-phase motor
   a bimetal motor, and
   a memory metal motor.
12. The implantable hydraulic restriction device according to any one of embodiments 10-11, further comprising a gear system placed between the motor and at least one of:
   the movable wall portion according to embodiment 6,
   the implantable pump according to embodiment 7, and
   the implantable valve member according to embodiment 9.
13. The implantable hydraulic restriction device according to embodiment 12, wherein the gear system comprises:
   an operable element,
   a first gear having the shape of a hollow cylinder, comprising a first number of teeth, on the peripheral outside thereof, and
   a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.
14. The implantable hydraulic restriction device according to embodiment 13, wherein the operable element comprises at least one of; a planetary gear and a structure or wheel at least partly using friction to interconnect with the first gear.
15. The implantable hydraulic restriction device according to any one of embodiments 5-14, further comprising a threaded member arranged to move the wall portion of the reservoir, and wherein the threaded member is connected to at least one of:
   the motor of any of embodiment 10 and 11,
   the gear system of any of embodiment 12-14,
   for transferring a rotating force to a reciprocating force for moving the wall portion.
16. The implantable hydraulic restriction device according to any one of embodiments 7-15, further comprising an injection port for supplying fluid to the reservoir.
17. The implantable hydraulic restriction device according to any one of embodiments 10-16, further comprising a servo connected between the motor and at least one of the:
   the movable wall portion of embodiment 6,
   the implantable pump of any of embodiments 7 and 8, and
   the implantable valve member of embodiment 9.
18. The implantable hydraulic restriction device according to any one of the preceding embodiments, wherein at least one of the first and second restriction elements is elongated and adapted to form a closed loop around the portion of the luminary organ.
19. The implantable hydraulic restriction device according to any one of embodiments 7-18, wherein the hydraulic pump is a peristaltic hydraulic pump, and wherein the hydraulic peristaltic pump comprises a hollow member for fluid transportation, and an operable compression member adapted to engage and compress the hollow member, and wherein the compression member is in direct or indirect connection with the motor such that motor operates the compression member such that fluid is transported in the hollow member.
20. The implantable hydraulic restriction device of embodiment 19, wherein the hollow member of the peristaltic pump forms a loop or part of a loop adapted to at least partially encircle at least one of the gear system and the motor in at least partially the same axial plane, and wherein the motor is adapted to propel the compressing member such that the compression member compresses the hollow member towards the outer periphery of the loop or part of loop.
21. The implantable hydraulic restriction device according to any one of embodiments 15-20, wherein the movement of the movable wall portion of the fluid reservoir by the threaded member in a first direction moves fluid from the fluid reservoir to the first hydraulic restriction element, and wherein movement of the movable wall portion of the fluid reservoir by the threaded member in a second direction moves fluid from the fluid reservoir to the second hydraulic restriction element.

22. The implantable hydraulic restriction device according to any one of the preceding embodiments, further comprising an implantable energizing unit for providing energy to any energy consuming components of the device to be implanted in the patient.
23. The implantable hydraulic restriction device according to any one of preceding embodiments, further comprising a wireless energy receiver, adapted to receive wireless energy from a wireless energy transmission device transmitting wireless energy from outside the patient's body to any energy consuming implantable component of the device including the implantable energizing unit of embodiment 22.
24. The implantable hydraulic restriction device according to any one of preceding embodiments, comprising a wireless energy transmission for wireless transfer of energy from outside the patient's body to any energy consuming implantable component of the device or to the implantable energizing unit of embodiment 22.
25. The implantable hydraulic restriction device according to any one of the preceding embodiments, further comprising a first implantable fluid reservoir and a first fluid conduit connecting the fluid reservoir to the first restriction element, and a second implantable fluid reservoir, a second fluid conduit connecting the second fluid reservoir to the second restriction element.
26. The implantable hydraulic restriction device according to any one of the preceding embodiments, wherein the second fluid reservoir comprising a dividing part of the first reservoir.
27. The implantable hydraulic restriction device according to embodiment 25, wherein at least one of;
the implantable first reservoir comprises at least one moveable wall portion for changing the volume of the implantable first fluid reservoir and thereby moving fluid from the implantable first fluid reservoir to the first elements, and
the implantable second reservoir comprises at least one moveable wall portion for changing the volume of the implantable second fluid reservoir and thereby moving fluid from the implantable second fluid reservoir to the second elements.
28. The implantable hydraulic restriction device according to embodiment 25, wherein the at least one moveable wall portion is adapted to change the volume of both the first and second fluid reservoirs for changing the volume to; increase the volume of the implantable first fluid reservoir, when the volume of the implantable second fluid reservoir is decreasing, and decrease the volume of the implantable first fluid reservoir, when the volume of the implantable second fluid reservoir is increasing.
29. The implantable hydraulic restriction device according to embodiment 25, further comprising at least one of;
a hydraulic pump, for pumping fluid from the first implantable reservoir to the first restriction element,
a hydraulic pump, for pumping fluid from the second implantable reservoir to the second restriction element, and
a hydraulic pump, for pumping fluid between the first and second implantable reservoir.
30. The implantable hydraulic restriction device according to embodiment 25, wherein the implantable first and second fluid reservoirs is divided by at least one moveable piston for changing the volume of the implantable fluid reservoirs and thereby increasing fluid in the first fluid reservoir simultaneously with decreasing fluid in the second fluid reservoir and vice versa.
31. The implantable hydraulic restriction device according to any one of preceding embodiments, comprising a control signal coming from outside the body to control the device, consisting of at least one of; a signal that overrides the automatic switching, an automatic executed signal, or a programming signal to program the terms for the automatic switching.
32. The implantable hydraulic restriction device according to any one of preceding embodiments, comprising a control signal consisting of a signal generated inside the body, to control the device, comprising at least one of; a signal that overrides the automatic switching, an automatic executed signal, a measured parameter, a calculated parameter, a functional parameter of the device, a physiological or physical parameter of the patient, and an input from any sensor.

Numbered Embodiment B 1-32

1. A hydraulic implantable restriction device for restricting a luminary organ of a patient, the hydraulic implantable restriction device comprising:
a first hydraulic restriction element adapted to restrict a first portion of the luminary organ, and
a second hydraulic restriction element adapted to restrict a second portion of the luminary organ, and
a control unit adapted to control the first and second restriction elements for automatically switching between restricting the first and second portion of the luminary organ, for creating a less damaging restriction, wherein the control unit is adapted to automatically switch between restricting the first and second portion of the luminary organ on the basis of the receipt of a control signal.
2. The implantable hydraulic restriction device according to any one of preceding embodiments, wherein any control signal coming from outside the body consists of at least one of; a signal that overrides the automatic switching, an automatic executed signal, or a programming signal to program the terms for the automatic switching.
3. The implantable hydraulic restriction device according to any one of preceding embodiments, wherein the control signal consists of a signal generated inside the body, comprising at least one of; a signal that overrides the automatic switching, an automatic executed signal, a measured parameter, a calculated parameter, a functional parameter of the device, a physiological or physical parameter of the patient, and an input from any sensor.
4. The implantable hydraulic restriction device according to any one of embodiments 1-3, wherein the implantable restriction device is adapted to restrict a luminary organ of the patient selected from a list consisting of:
an intestine of the patient,
a blood vessel of the patient,
the urethra of the patient,
the vas deference of the patient,
the stomach of the patient,
the esophagus of the patient,
the anal sphincter,
the cardia sphincter,
the urinary sphincter,
and the oviducts of the patient.
5. The implantable hydraulic restriction device according to any one of embodiments 1-4, wherein the receipt of a control signal is the receipt of a control signal generated on the basis of a sensor input.
6. The implantable hydraulic restriction device according to any one of embodiments 1-5, wherein the control signal is transmitted from outside of the body of the patient.
7. The implantable hydraulic restriction device according to any one of the preceding embodiments, further comprising an implantable fluid reservoir and a first fluid conduit connecting the fluid reservoir to the first restriction element, and a second fluid conduit connecting the fluid reservoir to the second restriction element.
8. The implantable hydraulic restriction device according to embodiment 7, wherein the implantable fluid reservoir comprises at least one moveable wall portion for changing the volume of the implantable fluid reservoir and thereby moving fluid from the implantable fluid reservoir to the first and second restriction elements.
9. The implantable hydraulic restriction device according to embodiment 7, further comprising a hydraulic pump, for pumping fluid from the implantable reservoir to at least one of the first and second restriction element.
10. The implantable hydraulic restriction device according to embodiment 9, wherein the hydraulic pump is a hydraulic pump selected from:
at least one reservoir acting as a pump by a wall of the reservoir moving,
at least one reservoir acting as a pump by changing volume,
at least one non-valve pump,
at least one valve pump,
at least one peristaltic pump,
at least one membrane pump,
at least one gear pump, and
at least one bellows pump.
11. The implantable hydraulic restriction device according to any one of embodiments 7-10, further comprising an implantable valve member for directing fluid from the implantable reservoir to the first or second restriction element.
12. The implantable hydraulic restriction device according to any one of embodiments 9 and 10, further comprising at least one motor for operating at least one of:
the movable wall portion according to embodiment 8,
the implantable pump according to embodiment 9, and
the implantable valve member according to embodiment 10.
13. The implantable hydraulic restriction device according to embodiment 12, wherein the motor comprises an electrical motor selected from:
an alternating current (AC) electrical motor,
a direct current (DC) electrical motor,
a linear electrical motor,
an axial electrical motor,
a piezo-electric motor,
a three-phase motor
a more than one-phase motor
a bimetal motor, and
a memory metal motor.
14. The implantable hydraulic restriction device according to any one of embodiments 12-13, further comprising a gear system placed between the motor and at least one of:
the movable wall portion according to embodiment 8,
the implantable pump according to embodiment 9, and
the implantable valve member according to embodiment 11.
15. The implantable hydraulic restriction device according to embodiment 14, wherein the gear system comprises:
an operable element,
a first gear having the shape of a hollow cylinder, comprising a first number of teeth, on the peripheral outside thereof, and
a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.
16. The implantable hydraulic restriction device according to embodiment 15, wherein the operable element comprises at least one of; a planetary gear and a structure or wheel at least partly using friction to interconnect with the first gear.
17. The implantable hydraulic restriction device according to any one of embodiments 7-16, further comprising a threaded member arranged to move the wall portion of the reservoir, and wherein the threaded member is connected to at least one of:
the motor of any of embodiment 12 and 13,
the gear system of any of embodiment 14-16, for transferring a rotating force to a reciprocating force for moving the wall portion.
18. The implantable hydraulic restriction device according to any one of embodiments 9-17, further comprising an injection port for supplying fluid to the reservoir.
19. The implantable hydraulic restriction device according to any one of embodiments 12-18, further comprising a servo connected between the motor and at least one of the:
the movable wall portion of embodiment 8,
the implantable pump of any of embodiments 9 and 10, and
the implantable valve member of embodiment 11.
20. The implantable hydraulic restriction device according to any one of the preceding embodiments, wherein at least one of the first and second restriction elements is elongated and adapted to form a closed loop around the portion of the luminary organ.
21. The implantable hydraulic restriction device according to any one of embodiments 9-20, wherein the hydraulic pump is a peristaltic hydraulic pump, and wherein the hydraulic peristaltic pump comprises a hollow member for fluid transportation, and an operable compression member adapted to engage and compress the hollow member, and wherein the compression member is in direct or indirect connection with the motor such that motor operates the compression member such that fluid is transported in the hollow member.
22. The implantable hydraulic restriction device of embodiment 21, wherein the hollow member of the peristaltic pump forms a loop or part of a loop adapted to at least partially encircle at least one of the gear system and the motor in at least partially the same axial plane, and wherein the motor is adapted to propel the compressing member such that the compression member compresses the hollow member towards the outer periphery of the loop or part of loop.

23. The implantable hydraulic restriction device according to any one of embodiments 17-22, wherein the movement of the movable wall portion of the fluid reservoir by the threaded member in a first direction moves fluid from the fluid reservoir to the first hydraulic restriction element, and wherein movement of the movable wall portion of the fluid reservoir by the threaded member in a second direction moves fluid from the fluid reservoir to the second hydraulic restriction element.

24. The implantable hydraulic restriction device according to any one of the preceding embodiments, further comprising an implantable energizing unit for providing energy to any energy consuming components of the device to be implanted in the patient.

25. The implantable hydraulic restriction device according to any one of preceding embodiments, further comprising a wireless energy receiver, adapted to receive wireless energy from a wireless energy transmission device transmitting wireless energy from outside the patient's body to any energy consuming implantable component of the device including the implantable energizing unit of embodiment 24.

26. The implantable hydraulic restriction device according to any one of preceding embodiments, comprising a wireless energy transmission for wireless transfer of energy from outside the patient's body to any energy consuming implantable component of the device or to the implantable energizing unit of embodiment 24.

27. The implantable hydraulic restriction device according to any one of the preceding embodiments, further comprising a first implantable fluid reservoir and a first fluid conduit connecting the fluid reservoir to the first restriction element, and a second implantable fluid reservoir, a second fluid conduit connecting the second fluid reservoir to the second restriction element.

28. The implantable hydraulic restriction device according to any one of the preceding embodiments, wherein the second fluid reservoir comprising a dividing part of the first reservoir.

29. The implantable hydraulic restriction device according to embodiment 27, wherein at least one of;
the implantable first reservoir comprises at least one moveable wall portion for changing the volume of the implantable first fluid reservoir and thereby moving fluid from the implantable first fluid reservoir to the first elements, and
the implantable second reservoir comprises at least one moveable wall portion for changing the volume of the implantable second fluid reservoir and thereby moving fluid from the implantable second fluid reservoir to the second elements.

30. The implantable hydraulic restriction device according to embodiment 27, wherein the at least one moveable wall portion is adapted to change the volume of both the first and second fluid reservoirs for changing the volume to; increase the volume of the implantable first fluid reservoir, when the volume of the implantable second fluid reservoir is decreasing, and decrease the volume of the implantable first fluid reservoir, when the volume of the implantable second fluid reservoir is increasing.

31. The implantable hydraulic restriction device according to embodiment 27, further comprising at least one of;
a hydraulic pump, for pumping fluid from the first implantable reservoir to the first restriction element,
a hydraulic pump, for pumping fluid from the second implantable reservoir to the second restriction element, and
a hydraulic pump, for pumping fluid between the first and second implantable reservoir.

32. The implantable hydraulic restriction device according to embodiment 27, wherein the implantable first and second fluid reservoirs is divided by at least one moveable piston for changing the volume of the implantable fluid reservoirs and thereby increasing fluid in the first fluid reservoir simultaneously with decreasing fluid in the second fluid reservoir and vice versa.

The different aspects or any part of an aspect of the different numbered embodiments or any part of an embodiment may all be combined in any possible way. Any method embodiment or any step of any method embodiment may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description.

The invention claimed is:

1. A hydraulic implantable restriction device for restricting a luminary organ of a patient, the hydraulic implantable restriction device comprising:
a first hydraulic elongated restriction element and forming means for forming the elongated restriction member into at least a substantially closed loop around a first portion of the luminary organ, the first elongated restriction element being adapted to restrict the first portion of the luminary organ, and
a second hydraulic elongated restriction element and forming means for forming the elongated restriction member into at least a substantially closed loop around a second portion of the luminary organ, the second elongated restriction element adapted to restrict the second portion of the luminary organ, and
a hydraulic pump, for pumping fluid from an implantable reservoir to at least one of the first and second restriction elements, the hydraulic pump comprising a hollow member for fluid transportation, and an operable compression member adapted to engage and compress the hollow member, the hydraulic pump being arranged for, upon compression of the hollow member, pumping fluid from one of the first and second restriction elements, via the hollow member, to the other one of the first and second restriction elements, such that operation of the hydraulic pump in a first operational state simultaneously causes the first hydraulic restriction element to restrict the first portion of the luminary organ and the second hydraulic restriction element to release the restriction of the second portion of the luminary organ, and in a second operational state simultaneously causes the first hydraulic restriction element to release the restriction of tile first portion of the luminary organ and the second hydraulic restriction element to restrict the second portion of the luminary organ, and a control unit adapted to control the hydraulic pump and to control the first and second restriction elements for automatically switching between restricting the first and second portion of the luminary organ, for creating a less damaging restriction, wherein the control unit is adapted to automatically switch between restricting the first and second portion of the luminary organ on a basis of at least one of:

a lapsed time being between 10 minutes and 6 months, and the patient using a function of the restricted luminary organ.

2. The implantable hydraulic restriction device according to claim 1, wherein the implantable restriction device is adapted to restrict a luminary organ of the patient selected from a list consisting of:

an intestine of the patient,
a blood vessel of the patient,
the urethra of the patient,
a vas deferens of the patient,
the stomach of the patient,
the esophagus of the patient,
the anal sphincter,
the cardia sphincter,
the urinary sphincter,
and
oviducts of the patient.

3. The implantable hydraulic restriction device according to claim 1, wherein the control unit is adapted to automatically switch between restricting the first and second portion of the luminary organ on the basis of the receipt of a control signal, wherein the control signal is generated on a basis of a sensor input.

4. The implantable hydraulic restriction device according to claim 1, wherein the control unit is adapted to automatically switch between restricting the first and second portion of the luminary organ on the basis of the receipt of a control signal, wherein the control signal is transmitted from outside of the body of the patient.

5. The implantable hydraulic restriction device according to claim 1, wherein the implantable fluid reservoir comprises at least one moveable wall portion for changing the volume of the implantable fluid reservoir and thereby moving fluid from the implantable fluid reservoir to the first and second restriction elements.

6. The implantable hydraulic restriction device according to claim 1, wherein the hydraulic pump is a hydraulic pump selected from:

at least one reservoir acting as a pump by a wall of the reservoir moving,
at least one reservoir acting as a pump by changing volume,
at least one non-valve pump,
at least one valve pump,
at least one peristaltic pump,
at least one membrane pump,
at least one gear pump, and
at least one bellows pump.

7. The implantable hydraulic restriction device according to claim 1, further comprising an implantable valve member for directing fluid from the implantable reservoir to the first or second restriction element.

8. The implantable hydraulic restriction device according to claim 1, further comprising at least one motor for operating at least one of:

a moveable wall portion comprised in the implantable fluid reservoir, the movable wall portion being for changing the volume of the implantable fluid reservoir and thereby moving fluid from the implantable fluid reservoir to the first and second restriction elements, the hydraulic pump, and an implantable valve member for directing fluid from the implantable reservoir to the first or second restriction element.

9. The implantable hydraulic restriction device according to claim 8, wherein the motor comprises an electrical motor selected from:

an alternating current (AC) electrical motor,
a direct current (DC) electrical motor,
a linear electrical motor,
an axial electrical motor,
a piezo-electric motor,
a three-phase motor
a more than one-phase motor
a bimetal motor, and
a memory metal motor.

10. The implantable hydraulic restriction device according to claim 8, further comprising a gear system placed between the motor and at least one of:

the movable wall portion,
the implantable pump, and
the implantable valve member.

11. The implantable hydraulic restriction device according to claim 10, wherein the gear system comprises:

an operable element,
a first gear having the shape of a hollow cylinder, comprising a first number of teeth, on a peripheral outside thereof, and
a second gear having the shape of a hollow cylinder, comprising a greater number of teeth than the first gear, on an inside surface thereof, wherein the operable element is adapted to engage an inside of the first gear, such that an outside of the first gear is pressed against an inside of the second gear such that the teeth of the first gear are interengaged with the teeth of the second gear in at least one position interspaced by positions at which the teeth are not interengaged, and wherein an operation of the operable element advances positions and thereby causes relative rotation between the first gear and the second gear.

12. The implantable hydraulic restriction device according to claim 11, wherein the operable element comprises at least one of: a planetary gear and a structure or wheel at least partly using friction to interconnect with the first gear.

13. The implantable hydraulic restriction device according to claim 8, further comprising a servo connected between the motor and at least one of the:

the movable wall portion,
the implantable pump, and
the implantable valve member.

14. The implantable hydraulic restriction device according to claim 1, further comprising a threaded member arranged to move a wall portion of the reservoir, and wherein the threaded member is connected to at least one of:

a motor for operating a movable wall portion, an implantable pump, or an implantable valve member,
a gear system placed between the motor and at least one of a movable wall portion, an implantable pump, and an implantable valve member, for transferring a rotating force to a reciprocating force for moving the wall portion.

15. The implantable hydraulic restriction device according to claim 14 wherein the movement of the movable wall portion of the fluid reservoir by the threaded member in a first direction moves fluid from the fluid reservoir to the first hydraulic restriction element, and wherein movement of the movable wall portion of the fluid reservoir by the threaded member in a second direction moves fluid from the fluid reservoir to the second hydraulic restriction element.

16. The implantable hydraulic restriction device according to claim 1, further comprising an injection port for supplying fluid to the reservoir.

17. The implantable hydraulic restriction device according to claim 1, wherein the hydraulic pump is a peristaltic hydraulic pump, and wherein the hydraulic peristaltic pump comprises a hollow member for fluid transportation, and an operable compression member adapted to engage and compress the hollow member, and wherein the compression member is in direct or indirect connection with a motor such that the motor operates the compression member such that fluid is transported in the hollow member.

18. The implantable hydraulic restriction device of claim 17, wherein the hollow member of the peristaltic pump forms a loop or part of a loop adapted to at least partially encircle at least one of a gear system and the motor in at least partially a same axial plane, and wherein the motor is adapted to propel a compression member such that the compression member compresses the hollow member towards the outer periphery of the loop or part of loop.

19. The implantable hydraulic restriction device according to claim 1, further comprising an implantable energizing unit for providing energy to any energy consuming components of the device to be implanted in the patient.

20. The implantable hydraulic restriction device according to claim 1, further comprising a wireless energy receiver, adapted to receive wireless energy from a wireless energy transmission device transmitting wireless energy from outside the patient's body to any energy consuming implantable component of the device including the implantable energizing unit of claim 19.

21. The implantable hydraulic restriction device according to claim 1, comprising a wireless energy transmission device for wireless transfer of energy from outside the patient's body to any energy consuming implantable component of the device or to the implantable energizing unit of claim 19.

22. The implantable hydraulic restriction device according to claim 1, further comprising a first implantable fluid reservoir and a first fluid conduit connecting the fluid reservoir to the first restriction element, and a second implantable fluid reservoir, a second fluid conduit connecting the second fluid reservoir to the second restriction element.

23. The implantable hydraulic restriction device according to claim 22, wherein at least one of:

the implantable first reservoir comprises at least one moveable wall portion for changing the volume of the implantable first fluid reservoir and thereby moving fluid from the implantable first fluid reservoir to the first restriction element, and the implantable second reservoir comprises at least one moveable wall portion for changing the volume of the implantable second fluid reservoir and thereby moving fluid from the implantable second fluid reservoir to the second restriction element.

24. The implantable hydraulic restriction device according to claim 23, wherein the at least one moveable wall portion is adapted to change the volume of both the first and second fluid reservoirs for changing the volume to increase the volume of the implantable first fluid reservoir, when the volume of the implantable second fluid reservoir is decreasing, and decrease the volume of the implantable first fluid reservoir, when the volume of the implantable second fluid reservoir is increasing.

25. The implantable hydraulic restriction device according to claim 22, further comprising at least one of:
   a hydraulic pump, for pumping fluid from the first implantable reservoir to the first restriction element,
      a hydraulic pump, for pumping fluid from the second implantable reservoir to the second restriction element, and
   a hydraulic pump, for pumping fluid between the first and second implantable reservoir.

26. The implantable hydraulic restriction device according to claim 22, wherein the implantable first and second fluid reservoirs are divided by at least one moveable piston for changing the volume of the implantable fluid reservoirs and thereby increasing fluid in the first fluid reservoir simultaneously with decreasing fluid in the second fluid reservoir and vice versa.

27. The implantable hydraulic restriction device according to claim 1, wherein a second fluid reservoir comprises a dividing part of a first reservoir.

28. The implantable hydraulic restriction device according to claim 1, wherein the control unit is adapted to respond to a control signal coming from outside the body of the patient to control the device, consisting of at least one of: a signal that overrides the automatic switching, an automatic executed signal, or a programming signal to program terms for the automatic switching.

29. The implantable hydraulic restriction device according to claim 1, wherein the control unit is adapted to respond to a control signal consisting of a signal generated inside the body of the patient, to control the device, comprising at least one of: a signal that overrides the automatic switching, an automatic executed signal, a measured parameter, a calculated parameter, a functional parameter of the device, a physiological or physical parameter of the patient, and an input from any sensor.

\* \* \* \* \*